United States Patent [19]

Kahne

[11] Patent Number: 5,780,444
[45] Date of Patent: Jul. 14, 1998

[54] COMPOSITIONS AND METHODS FOR CELL TRANSFORMATION

[75] Inventor: Suzanne Walker Kahne, Princeton, N.J.

[73] Assignee: Trustees of Princeton University, Princeton, N.J.

[21] Appl. No.: 425,118

[22] Filed: Apr. 20, 1995

Related U.S. Application Data

[63] Continuation-in-part of Ser. No. 336,675, Nov. 7, 1994, which is a continuation-in-part of Ser. No. 264,488, Jun. 23, 1994, Pat. No. 5,627,270, which is a continuation-in-part of Ser. No. 230,685, Apr. 20, 1994, which is a continuation-in-part of Ser. No. 989,667, Dec. 14, 1992, Pat. No. 5,571,795, which is a continuation-in-part of Ser. No. 806,985, Dec. 13, 1991, Pat. No. 5,338,837.

[51] Int. Cl.$^6$ .................. A61K 31/705; A61K 31/56; C07J 1/00
[52] U.S. Cl. .............. 514/26; 514/169; 514/170; 514/178; 514/182; 536/5; 930/10
[58] Field of Search ............... 514/26, 169, 170, 514/178, 182; 536/5; 930/10

[56] References Cited

U.S. PATENT DOCUMENTS

| | | | |
|---|---|---|---|
| 4,994,439 | 2/1991 | Longnecker et al. | 514/3 |
| 5,122,520 | 6/1992 | Azria et al. | 514/171 |
| 5,192,756 | 3/1993 | Zasloff et al. | 514/182 |
| 5,273,965 | 12/1993 | Kensil et al. | 514/3 |
| 5,338,837 | 8/1994 | Kahne et al. | 536/5 |
| 5,455,335 | 10/1995 | Kahne et al. | 536/5 |
| 5,571,795 | 11/1996 | Kahne et al. | 514/26 |
| 5,627,270 | 5/1997 | Kahne et al. | 536/5 |

FOREIGN PATENT DOCUMENTS

| | | |
|---|---|---|
| WO A 91/14696 | 10/1991 | WIPO . |

OTHER PUBLICATIONS

The Merck Index. (Eleventh Edition), pp. 868–869, (1989).
Cantor & Schimmel. *Biophysical Chemistry: Part I The Conformation of Biological Macromolecules* (W.H. Freeman & Co. : New York), pp. 227–234, (1980).
Friedman, T., *Science* (1989) 244:1275–1281.
Felgner, P.L., *Adv. Drug Deliv. Rev.* (1990) 5:163–187.
Nicolau, C., *Proc. Natl. Acad. Sci. USA* (1983) 80:1068–1072.
Felgner, P.L., *Proc. Natl. Acad. Sci. USA* (1987) 84:7413–7417.
Felgner, P.L. and Ringold, G.M., *Nature* (1989) 337:387–388.
Brunette, E., et al., *Nucl. Acids Res.* (1992) 20(5):1151.
Jarnagin, W.R. et al., *Nucl. Acids Res.* (1992) 20(16):4205–4211.
Malone, R.W., *Proc. Natl. Acad. Sci. USA* (1989) 86:6077–6081.
Mannino, R.J. and Gould-Fogerite, S., *Biotechniques* (1988) 6(7):682–670.
Behr, J.P. et al., *Proc. Natl. Acad. Sci. USA* (1989) 86:6982–6986.
Leonetti, J.P. et al., *Proc. Natl. Acad. Sci. USA* (1990) 87:2448–2451.
Juliano, R.L. and Akhtar, S., *Antisense Research and Development* (1992) 2:165–176.

(List continued on next page.)

*Primary Examiner*—John Kight
*Assistant Examiner*—Howard C. Lee
*Attorney, Agent, or Firm*—Lowe, Price, LeBlanc & Becker

[57] ABSTRACT

The present invention relates to methods and compositions for the transformation of cells. In particular, compositions and methods are disclosed which include combinations of the nucleic acid of interest and polyhydroxylated or polyglycosylated steroid molecules. Most preferably, exogenous or endogenous nucleic acid is contacted with the cell in the presence of a bile acid (e.g., cholic acid) derivatized with an amine-containing side chain.

66 Claims, 21 Drawing Sheets

OTHER PUBLICATIONS

Legendere, J.Y. and Szoka, Jr., F.C., *Proc. Natl. Acad. Sci. USA* (1993) 90:893–897.

Clark, P.O. and Leach, F.R., *Molec. Gen. Genet.* (1980) 178:21–25.

Gilboa, E. et al., *Biotechniques* (1986) 4(6):504–511.

Rosenfield, M.A. et al., *Science* (1991) 252:431–434.

Kaneda, Y. et al., *Science* (1989) 243:375–378.

Bellini, A.M. et al., *Arch. Pharm. (Weinheim)* (1990) 323:201–205.

Bellini, A.M. et al., *Eur. J. Med. Chem* (1983) 18(2):185–190.

Bellini, A.M. et al., *Eur. J. Med. Chem* (1983) 18(2):191–195.

Sambrook, J.; Fritsch, E.F.; and Maniatis, T., *Molecular Cloning*, Cold Spring Harbor University Press: Cold Spring Harbor, 1989.

Aubin, R., Weinfeld, M., Paterson, M.C., Chap. 1, *Methods and Molecular Biology*, vol. 7.

Perrine, T.D. et al., *J. Org. Chem.* (1967) 32:664.

Ferrier, R.J. et al., *Carbohyd. Res* (1973) 27:55.

*Gene Transfer and Expression Protocols*, Murray, E.J., ed., Human Press: Clifton, NJ 1991.

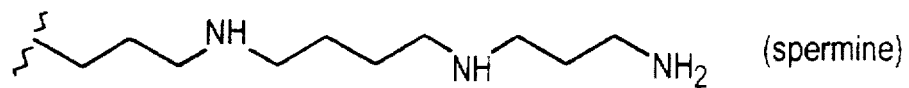 (spermine)
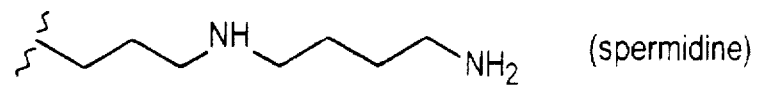 (spermidine)
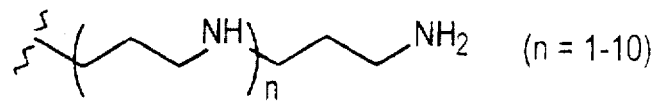 (n = 1-10)
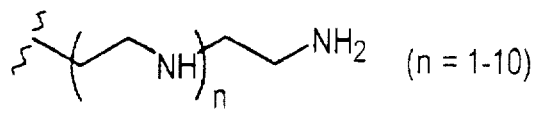 (n = 1-10)
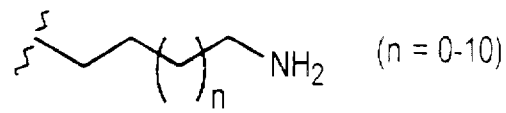 (n = 0-10)
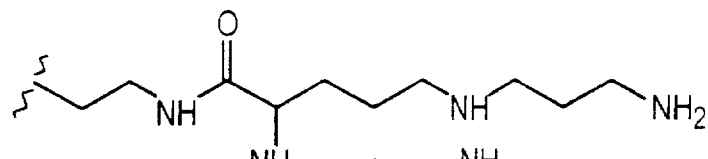
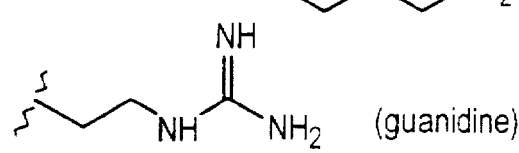 (guanidine)
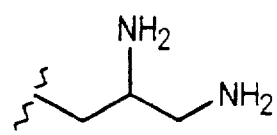
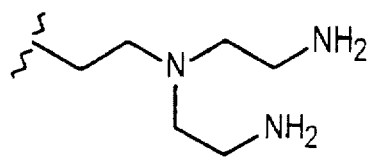
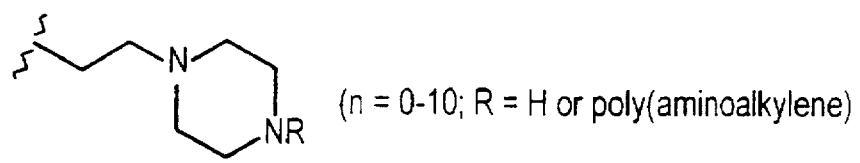 (n = 0-10; R = H or poly(aminoalkylene))
FIG. 3

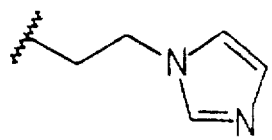
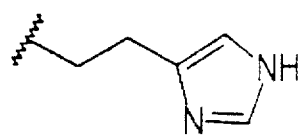
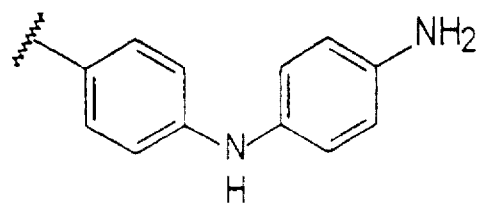
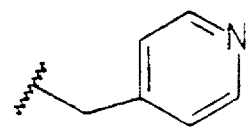
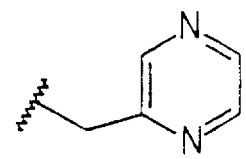
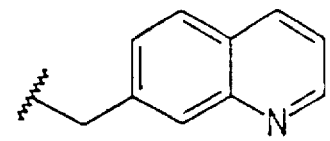
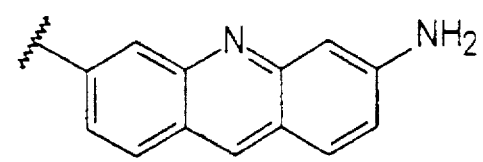
FIG. 4

R = -CH(CH₃) CH₂CH₂CO₂N-succinyl

| Compound | R' | R'' | RX |
|---|---|---|---|
| 1 | -OH | -H | -CH(CH₃)CH₂CH₂CONH(CH₂CH₂NH)₃CH₂CH₂NH₂ |
| 2 | -OH | -H | -CH(CH₃)CH₂CH₂CONH(CH₂CH₂NH)₄CH₂CH₂NH₂ |
| 3 | -H | -OH | -CH(CH₃)CH₂CH₂CONH(CH₂)₃NH(CH₂)₄NH(CH₂)₃NH₂ |

FIG. 12

COMPOUNDS USED IN THE TRANSPORTATION STUDY OF
pSVβPLASMID FOR EXPRESSING β-GALACTOSIDASE GENE
IN COS-7 CELLS

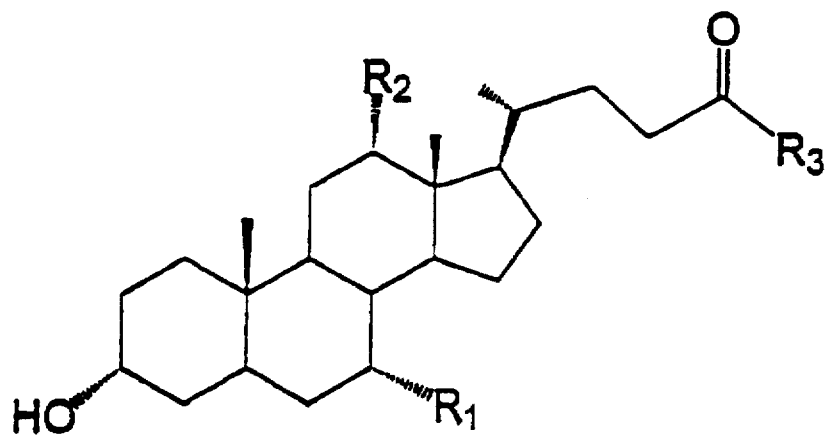

1    $R_1 = R_2 =$   O-α-D-glucopyranose; $R_3 =$ OCH$_3$ (F)   2    $R_1 = R_2 =$   OH; $R_3 =$ *Spermine (O)   3    $R_1 =$ H; $R_2 =$ O-α-D-glucopyranose; $R_3 =$ *Spermine (P)   4    $R_1 =$ O-α-D-glucopyranose; $R_2 =$ H; $R_3 =$ *Spermine (E)   5    $R_1 = R_2 =$ O-α-D-glucopyranose; $R_3 =$ *Spermine (N)   6    $R_1 = R_2 =$ O-α-D-glucopyranose;

$$R_3 = \text{-NH-(CH}_2\text{-CH}_2\text{-NH)}_3\text{-(CH}_2\text{)}_2\text{-NH}_2$$

(M)   7    $R_1 = R_2 =$ O-α-D-glucopyranose;

$$R_3 = \text{-NH-(CH}_2\text{-CH}_2\text{-NH)}_4\text{-(CH}_2\text{)}_2\text{-NH}_2$$

*Spermine = -NH-(CH$_2$)$_3$-NH-(CH$_2$)$_4$-NH-(CH$_2$)$_3$-NH$_2$

Synthesis of Glycosylated-Steroid Polymine conjugates
Scheme 1
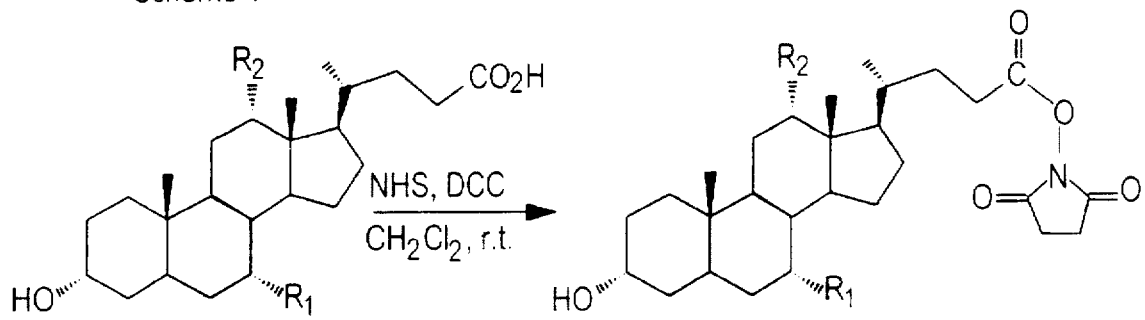
8 $R_1 = R_2 = OH$
*9 $R_1 = R_2 = O\text{-}\alpha\text{-tetra-}O\text{-benzyl-}D\text{-glucose}$
*For synthesis see Reference 10 and 11
10 $R_1 = R_2 = OH$
11 $R_1 = R_2 = O\text{-}\alpha\text{-tetra-}O\text{-benzyl-}D\text{-glucose}$
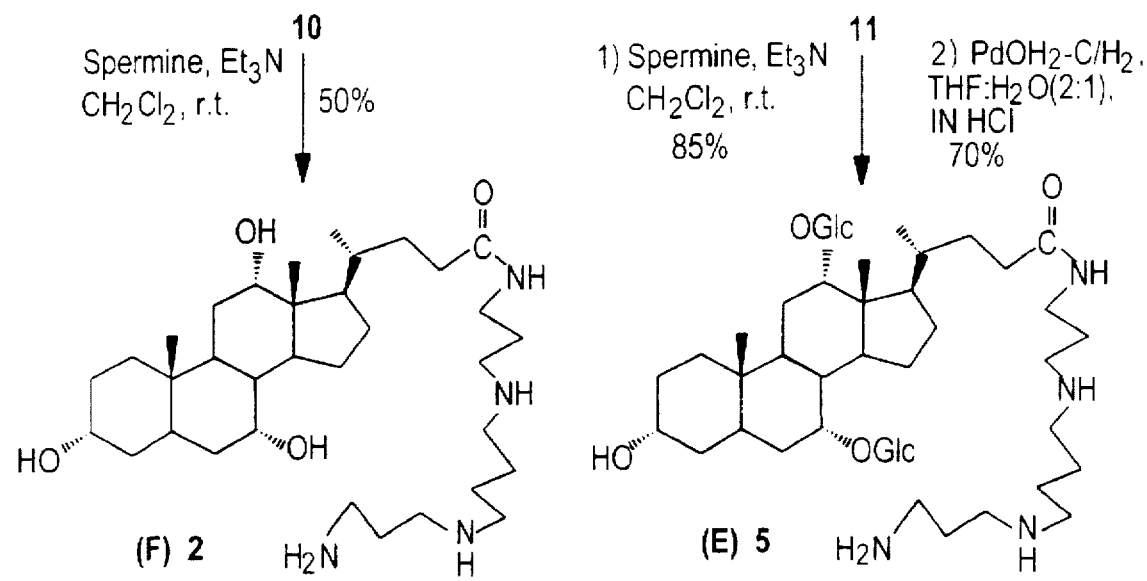
Glc= α-D-glucopyranose
FIG. 13 pSVβ PLASMID FOR EXPRESSING β-GALACTOSIDASE GENE

I REGION OF SEQUENCE DATA
★ SPLICE DONOR/SPLICE ACCEPTOR
◆ SV40 POLYADENYLATION
■ ENHANCER
▲ PEARLY

FIG. 16

RESULTS OF TRANSFECTIONS WITH TRANSCELL COMPOUNDS

| Compound No. | Polyamine Side Chain | Ratio Cmpd/DNA Charge | Ratio Cmpd/DNA Mole | %Transfection Relative to Lipofection |
|---|---|---|---|---|
| 2 (F) | -NH-(CH$_2$)$_3$-NH-(CH$_2$)$_4$-NH-(CH$_2$)$_3$-NH$_2$ | 25 | 17 | 27 |
| 3 (O) | -NH-(CH$_2$)$_3$-NH-(CH$_2$)$_4$-NH-(CH$_2$)$_3$-NH$_2$ | 24 | 16 | 20 |
| 4 (P) | -NH-(CH$_2$)$_3$-NH-(CH$_2$)$_4$-NH-(CH$_2$)$_3$-NH$_2$ | 24 | 16 | 207 |
| 5 (E) | -NH-(CH$_2$)$_3$-NH-(CH$_2$)$_4$-NH-(CH$_2$)$_3$-NH$_2$ | 96 | 64 | 380 |
| 6 (N) | -NH-(CH$_2$-CH$_2$-NH)$_3$-CH$_2$-CH$_2$-NH$_2$ | 96 | 64 | 127 |
| 7 (M) | -NH-(CH$_2$-CH$_2$-NH)$_4$-CH$_2$-CH$_2$-NH$_2$ | 58 | 24 | 1300 |

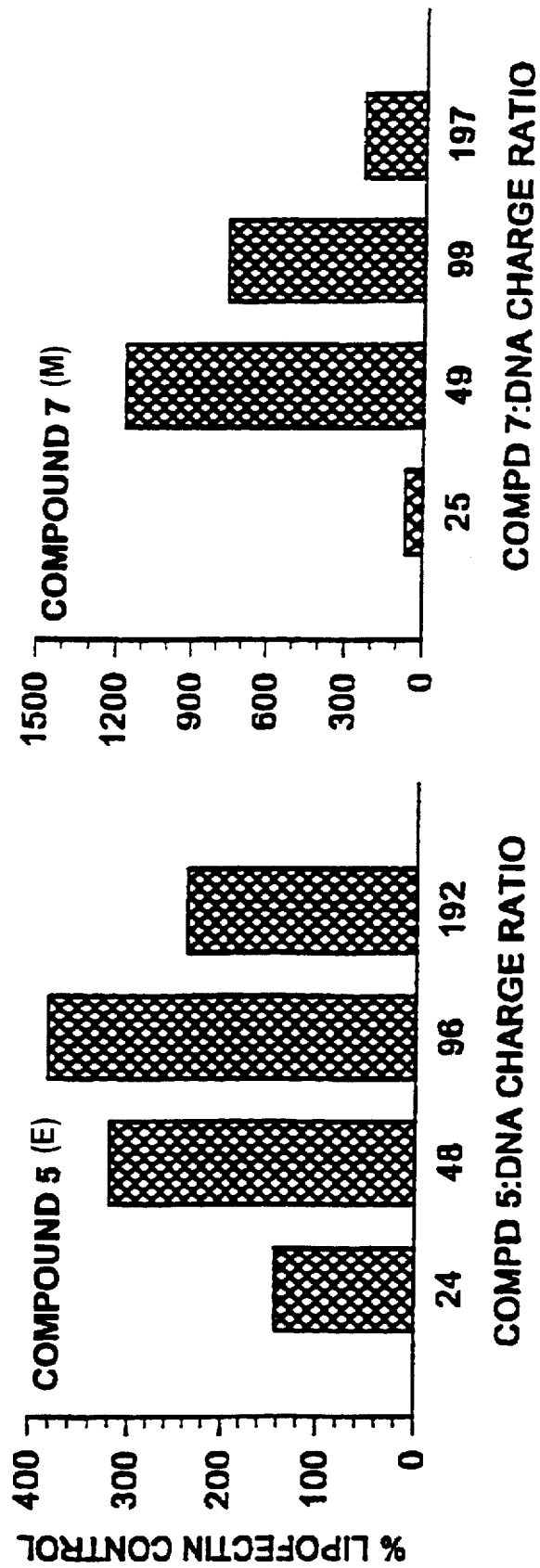

FIG. 18

COMPARISON OF ONPG AND X-GAL ASSAYS FOR COMPOUND M:DOPE COMPLEX

| CHARGE RATIO (COMPOUND:DNA) | % LIPOFECTIN CONTROL | |
|---|---|---|
| | ONPG | X-GAL |
| 3 | 11 | 7.8 |
| 6 | 23 | 7.8 |
| 12 | 14 | 10.5 |
| 25 | 88 | 63.1 |
| 49 | 1215 | 1241 |
| 99 | 811 | 350 |
| 197 | 318 | 68.4 |
| 394 | 84 | 52 |

THE LEVEL OF β-GALACTOSIDASE EXPRESSION INCREASES CONCURRENTLY WITH TRANSFECTION FREQUENCY.

COMPOSITIONS AND METHODS FOR CELL TRANSFORMATION

CROSS-REFERENCE TO RELATED APPLICATIONS

The present application is a continuation-in-part (CIP) of U.S. application Ser. No. 08/336,675, filed Nov. 7, 1994, which, in turn, is a CIP of U.S. application Ser. No. 08/264,488, filed Jun. 23, 1994, now Pat. No. 5,627,270 which, in turn, is a CIP of U.S. application Ser. No. 08/230,685, filed Apr. 20, 1994, which, in turn, is a CIP of U.S. application Ser. No. 07/989,667, filed Dec. 14, 1992, now Pat. No. 5,571,795, which, in turn, is a CIP of U.S. application Ser. No. 07/806,985, filed Dec. 13, 1991, now U.S. Pat. No. 5,338,837, the disclosures of which are incorporated herein by reference.

FIELD OF THE INVENTION

The present invention relates to methods and compositions for the transformation of cells, which transformation involves the introduction of nucleic acid into eucaryotic and procaryotic cells. In particular, compositions and methods are disclosed which include combinations of the endogenous or exogenous nucleic acid of interest and polyhydroxylated or polyglycosylated steroid molecules, which include amine-containing groups that allow these molecules to be positively charged. The disclosed combinations include, preferably, at least one neutral lipid component, including, but not limited to, fatty acid esters, triglycerides, phospholipids, glycolipids, other steroid derivatives, such as cholesterol and cholesteryl esters, and lipoprotein complexes. The neutral lipid component is, preferably, a fusogenic lipid. As an example, the nucleic acid (e.g., exogenous nucleic acid) is contacted with the cell in the presence of a 1:1 mixture of dioleoyl phosphatidylethanolamine and a polyglycosylated cholic acid derivatized with a biogenic polyamine side chain.

BACKGROUND OF THE INVENTION

With the development of DNA recombinant methods and the advent of the biotechnology industry, methods for introducing nucleic acids into cells have been an ongoing focus of biologists and others in the field, partly because the efficiency of this process has remained quite low. For example, Friedmann, T. states in a review article, discussing progress toward human gene therapy and which appeared in *Science* (1989) 244:1275–1281, that efficiency of physical transfection methods in vitro can approach or exceed 1% in suitable recipient cells.

Research workers seeking to effect the transformation of cells, whether the cells are used in culture for the production of selected gene products or the cells form part of the organs or tissues of a living subject (i.e., in gene therapy), have resorted to a number of general strategies, including coprecipitation of the nucleic acid with inorganic salts, electroporation, direct injection of the oligonucleotide or use of cationic lipid/ nucleic acid mixtures.

Hence, Felgner, P. L., in *Adv. Drug Deliv. Rev.* (1990) 5:163–187, surveys the various methods for delivery of functional polynucleotides in vitro and in vivo, including the use of cationic polypeptides, diethylaminoethyldextran (DEAE dextran), calcium phosphate and other insoluble inorganic salts, liposomes, proteo-liposomes, and cationic lipids (e.g., N-|1-(2,3-dioleoyloxy)propyl|-N,N,N-trimethyl ammonium chloride or DOTMA).

Liposomes have been a popular vehicle for introducing DNA into cells. For instance, Nicolau, C. et al., in *Proc. Natl. Acad. Sci. USA* (1983) 80:1068–1072, disclose the apparent in vivo expression of rat insulin in rat after i.v. administration of liposome-entrapped plasmid containing a sequence encoding rat preproinsulin I. Liposomes were made from a mixture of egg yolk phosphatidylcholine/ox brain phosphatidylserine/cholesterol, 8:2:10 (mol/mol/mol). These workers observed significant but transitory expression of insulin by liver and spleen cells.

Cationic liposome-mediated transfection (dubbed "lipofection") has been made popular by the work of Feigner and co-workers. The use of DOTMA in a DNA-transfection protocol has been described by Felgner, P. L. et al. *Proc. Natl. Acad. Sci. USA* (1987) 84:7417. The DOTMA is incorporated in dioleoyl phosphatidylethanolamine-based liposomes. DNA-total lipid complex is then prepared in HBS, which are then added to just-confluent cells. These authors claim to obtain 5- to >100-fold increased transfection over that shown for calcium phosphate on DEAE-dextran. In *Focus* (1989) 11(2):21–25, Felgner, P. L. and Holm, M. discuss the use of DOTMA, which is capable of forming liposomes and, importantly, capable of interacting spontaneously with DNA or RNA, to form a liposome/polynucleotide complex. A transfection reagent is described which can be used with a "wide variety of tissue culture cells and with different classes of polynucleotides including DNA, MRNA, dsRNA." Cells are incubated for 24–48 h at 37° C. In *Nature* (1989) 337:387–388, Felgner, P. L. and Ringold, G. M. further discuss cationic liposome-mediated transfection using DOTMA. A schematic on p. 387 of this article shows the proposed structure of a liposome/nucleic acid complex. The authors note that one wants a net positive charge for the complex.

Mixtures of cationic lipid (DOTMA) and dioleoyl phosphatidy-lethanolamine (DOPE), commercially available as LIPOFECTIN™, and other cationic lipid-containing transfection-mediating compositions are described in articles by Brunette, E. et al. in *Nucl. Acids Res.* (1992) 20(5):1151 and Jarnagin, W. R. et al. in *Ibid.* (1992) 20(16):4205. Use of a mixture of lysinylphophatidylethanolamine (L-PE) and the cholesterol ester of beta-alanine (CEBA) is also disclosed in the latter article.

Malone, R. W. et al. in *Proc. Natl. Acad. Sci. USA* (1989) 86:6077–6081, describe the use of lipofection for cationic liposome-mediated RNA transfection. In this work, DOTMA was incorporated into liposomes with dioleoyl phosphatidylethanolamine (DOPE) in a 1:1 (mol/mol) ratio.

In an article appearing in *Biotechniques* (1988) 6(7): 682–670, Mannino, R. J. and Gould-Fogerite, S. discuss liposomes for use as "custom-designed cell-type specific gene transfer vehicles." These workers use large unilamellar vesicles (LUV) for high molecular weight molecules such as RNA and DNA (0.2–4.0 mm). The authors enumerate four characteristics that an efficient gene transfer vehicle should possess: (i) encapsulation of DNA; (ii) targeting and binding to target cells; (iii) fusion and delivery of liposome contents; (iv) nuclear targeting and expression. The liposomes were prepared from phosphatidylcholine and cholesterol.

Behr, J. P. et al., in *Proc. Natl. Acad. Sci. USA* (1989) 86:6982–6986, describe gene transfer experiments into mammalian primary endocrine cells using lipopolyamine-coated DNA. Certain lipocarboxyspermine derivatives are described which the authors contend mediate the successful transfection of a variety of eukaryotic cell cultures. The bacterial chloramphenicol acetyl-transferase (CAT) gene is used as the marker for gene transfer. The disclosure of this reference, and all others cited in the present application, is incorporated by reference herein.

In addition, Leonetti, J. P. et al., in *Proc. Natl. Acad. Sci. USA* (1990) 87:2448–2451, discuss the use of antibody-targeted liposomes bearing oligonucleotides complementary to viral RNA. Encapsulated oligomers resist DNAse and are active in amounts 1–2 orders of magnitude lower than those reported for unencapsulated oligomer sequences. Liposomes are prepared from mixtures of dipalmitoyl phosphatidylcholine (65%), cholesterol (34% mol), and N-succinimidyl-3-(2-pyridyldithio)propionate-modified phosphatidylethanolamine (1% mol). The liposomes were conjugated to protein A and used in conjunction with protein A-binding monoclonal antibodies. Virus production was allegedly inhibited in vitro.

Juliano, R. L. and Akhtar, S., in *Antisense Research and Development* (1992) 2:165–176, focus on the use of liposomes as drug delivery systems for antisense oligonucleotides. The different types of liposomes of potential use are discussed, including small unilamellar vesicles (SUVs), large unilamellar vesicles (LUVs), multilamellar vesicles (MLVs), and long circulation lifetime liposomes (LC-Lipos). So called fusogenic liposomes and antibody-conjugated liposomes are also described.

Complex mixtures involving DNA/protein and lipid/peptide complexes have very recently been utilized in DNA transfection protocols. In particular, Legendre, J. Y. and Szoka, Jr., F. C., in *Proc. Natl. Acad. Sci. USA* (1993) 90:893–897, discuss the use of "cyclic cationic amphipathic peptide gramicidin S and dioleoyl phosphatidylethanolamine." Certain combinations of DNA/peptide at 1:1 "charge ratio" and lipid/peptide at 5:1 "molar ratio" are disclosed. These workers boast transfection levels up to 20-fold higher than cationic liposomes in adherent mammalian cells and cite evidence that supports DNA entry into the cell via the plasma membrane. This work purports to address the need for improving transfection efficiency in non-viral systems. The article further suggests that the hydrophobic face of gramicidin S is important for transfection activity, diminishing, somewhat, the importance of charge neutralization. The authors allege that the phospholipids have two functions: to decrease the cytotoxicity of the gramicidin S; to enhance the transfection level.

Clark, P. O. and Leach F. R., in *Molec. Gen. Genet.* (1980) 178:21–25, have described the effect of millimolar concentrations of spermidine on the transformability of *Bacillus subtilis* cells. Maximum stimulation of the cells is observed when spermidine is added 30 minutes before DNA.

On the other hand, Gilbon, E. et al., in *Biotechniques* (1986) 4(6):504–511, discuss the utility of retroviral-mediated gene transfer for delivering a particular gene into a large fraction of a given cell population. Rosenfield, M. A. et al., in an article that appeared in *Science* (1991) 252:431–434, disclose the use of the Adenovirus genome, containing a cDNA expression cassette, for transfection of rat lung epithelium in vivo.

Lastly, Kaneda, Y. et al., in *Science* (1989) 243:375–378, observe increased expression of DNA cointroduced with nuclear proteins upon injection into the portal veins of adult rats. Expression was allegedly observed upon addition to cultural cells. The DNA and nuclear proteins were incorporated into Sendai virus-fused lipid vesicles.

In the general area of polyamine-steroid nucleus conjugates, a naturally-occurring spermidine-cholestanyl compound having antibiotic activity is described in U.S. Pat. No. 5,192,756, granted to Zasloff et al. Mar. 9, 1993. This compound was isolated from the stomach of the common dogfish shark, *Squalus acanthias*. However, the specification contains no disclosure of any uses of this compound other than for its alleged antibiotic activity.

Bellini, A. M. and co-workers, in *Arch. Pharm.* (Weinheim) (1990) 323:201–205, have described the antimicrobial activity of basic cholane derivatives. These research workers found that hydrophobic amine derivatives possessed the highest antimicrobial activity. The mechanism of action was attributed to membrane crossing rather than receptor contact. This article states on page 205 that the unionized species is the active species. Moreover, this article contains no disclosure, teaching or suggestion regarding nucleic acid transformation processes. Two earlier articles by Bellini and co-workers, in *Eur. J. Med. Chem.* (1983) 18(2):185–190 and *Ibid.* (1983) 18(2):191–195, described similar compounds and their antimicrobial activity. It is further noted that none of the derivatives disclosed included a polyamine chain that possessed at least one unsubstituted (i.e., —$NH_2$) amine group.

Burrows and co-workers have synthesized certain sterol dimers and trimers using amine spacers, as described in Abstract Nos. 193 and 304 from the 208th ACS National Meeting, Division of Organic Chemistry. These dimers and trimers are alleged to form cavities that bind to DNA.

Thus, there remains a need in the art for more effective ways of achieving transfection and, more generally, of introducing endogenous or exogenous nucleic acids into cells and, thus, affecting their genetic makeup.

SUMMARY OF THE INVENTION

Accordingly, it is an object of the present invention to provide a method of introducing nucleic acid into cells by transformation. Broadly, the present invention comprises contacting the cells with the nucleic acid (exogenous or endogenous) in the presence of a compound, which comprises a bile acid-based molecule and at least one amine-containing moiety, preferably a polyamine. In one embodiment of the invention, a lipid, most preferably a neutral lipid, is also present in the contacting step. Optionally, the transfection medium also contains cationic lipids.

It has been discovered that the efficiency of transformation is increased in the presence of the compounds described herein compared with the transformation efficiency in the absence of same. Thus, the present invention can be used in a variety of applications, including, but not limited to, the is facilitation of gene expression, protein engineering, protein production by a transformed host cell, cloning and subcloning procedures, antisense, gene therapies, and the like.

The present invention also seeks to provide the compounds which are of particular interest in achieving the above-noted objectives, as well as compositions comprising same. Thus, a further object of the present invention relates to the enhancement of the transformability of a host cell which includes contacting the host cell to be transformed with an effective amount of a compound of the invention or a composition containing same.

By using the compounds, compositions, and methods disclosed, it has been found that the introduction of nucleic acids into cells can be greatly facilitated. More importantly, the ability to deliver the nucleic acid can be extended potentially to those cells that comprise the tissues and organs of living organisms, with the consequent diagnostic, prophylactic, and therapeutic benefits associated therewith.

Other objects of the present invention will become apparent to those of ordinary skill in the art upon further consid-

BRIEF DESCRIPTION OF THE FIGURES

FIG. 3 shows additional examples of the types of aliphatic amine moieties suitable for conjugation to the bile acid compounds described herein.

FIG. 4 shows further examples of the types of aromatic amine moieties suitable for conjugation to the bile acid compounds described herein.

FIG. 12 lists some of the compounds that were used for the transformation of COS-7 cells.

FIG. 13 illustrates the synthetic scheme for selected compounds 2 and 5 of FIG. 12.

FIG. 16 is a table listing some of the results of the transformation experiments.

FIGS. 17A and 17B are graphical representations of the transformation efficacy relative to compound:DNA charge ratio.

FIG. 18 is a table comparing results for the ONPG and X-GAL assays for various compound M/DOPE complex to DNA charge ratios.

DETAILED DESCRIPTION OF THE INVENTION

Figure 1:
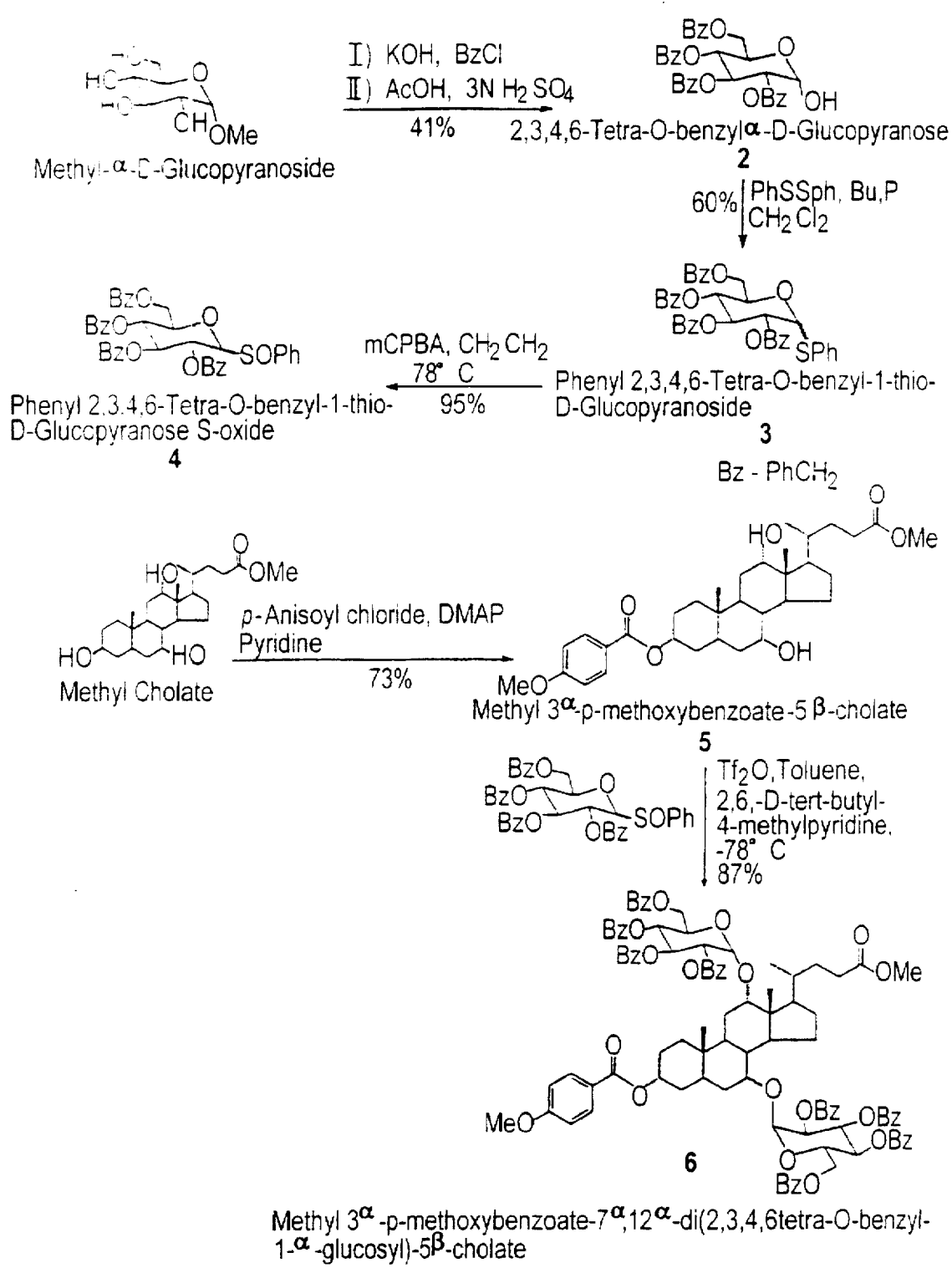
FIG. 1 illustrates the synthetic scheme for the preparation of 3α-p-methoxybenzoate-7α,12α-di(2,3,4,6-tetra-O-benzyl-1'α-glucosyl)-5β-cholan-24-oic acid, methyl ester.

The compounds, compositions, and methods of the present invention may be applied for the advantageous introduction of nucleic acid, particularly exogenous nucleic acid, to a cell. In particular, the present method for the introduction of exogenous nucleic acid to a cell comprises: (a) contacting a cell with nucleic acid in the presence of a compound of the formula (I):

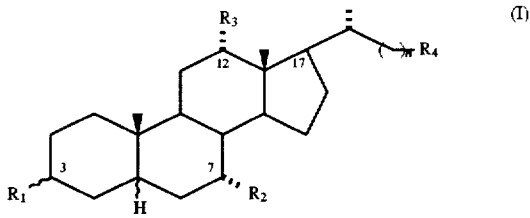

in which $R_1$ can be an H, OH, $OR_5$, $NH_2$, $NHR_6$ or $NR_6R_7$; $R_2$ and $R_3$ may be the same or different and can be an H, OH or $OR_5$; $R_4$ can be $CONH_2$, $CONHR_6$, $CONR_6R_7$, $CH_2NH_2$, $CH_2NHR_6$, $CH_2NR_6R_7$, $CO_2$—Y—$NH_2$, $CO_2$—Y—$NHR_6$, or $CO_2$—Y—$NR_6R_7$; $R_5$ is a protected or unprotected glycosyl moiety comprising 1–10 monosaccharide units in which the glycosidic linkage at the anomeric carbon atom of each monosaccharide unit is independently alpha or beta; $NH_2$, $NHR_6$, and $NR_6R_7$ represent an unsubstituted amino group, monosubstituted amino groups, and a disubstituted amino group, respectively, in which $R_6$ and $R_7$ may be the same or different and represent a linear, branched or cyclic hydrocarbon group (e.g., an aliphatic group, a cyclic aliphatic group, an aromatic group or combinations of same) comprising 1–15 carbon atoms optionally substituted with one or more unsubstituted, monosubstituted or disubstituted amino groups; Y represents a linear or branched alkylene group comprising 1–10 carbon atoms; n is an integer from 0–10, preferably 0–3; or its acid addition or quaternary ammonium salt; and (b) allowing the nucleic acid to remain in contact with the cell in the presence of the compound for a period of time sufficient to effect the introduction of the nucleic acid to the cell.

The degree of substitution of the amino group is determined by the number of bonds to hydrogen emanating from the amino group. Thus, an unsubstituted amino group has two N—H bonds (e.g., —$CH_2$—$CH_2$—$NH_2$). A monosubstituted amino group has one N—H bond (e.g., —$CH_2$—NH—$CH_2$— or —CH=NH). A disubstituted amino group has none (e.g., =CH—NR—$CH_2$— or —CH=N—CH=). By "substituted with one or more unsubstituted, monosubstituted or disubstituted amino groups" is meant that the hydrocarbon group comprising 1–15 carbon atoms contains at least one amino group either within the hydrocarbon backbone (e.g., —$CH_2$—NH—$CH_2$—, —$CH_2$—NR—

$CH_2$—, —CH=N—$CH_2$, —CH=N—CH=, and the like) or coming off the backbone (e.g., a primary amine, a secondary amine, a tertiary amine, an imine or the like, such as —$CH_2$—$CH_2$—$NH_2$, —$CH_2$—CH(-$NH_2$)—$CH_2$—, —$CH_2$—CR($NH_2$)—$CH_2$—, —CH=NH or —CR=NH).

Accordingly, such amino groups are capable of accommodating a charge, for example, in protic media (e.g., —$CH_2$—$NH_2\oplus$—$CH_2$— or —$CH_2$—$CH_2$—$NH_3\oplus$) or on formation of a quaternary ammonium salt (e.g., —$CH_2$—$CH_2$—$NMe_3\oplus$, wherein Me stands for methyl). The preferred compounds of the present invention include those that are able to accommodate two or more positive charges. Yet others can accommodate three, four or even more positive charges.

Additional examples of selected amino group-containing moieties, that may be used as R6 and/or R7, can be found in FIGS. 3 and 4.

As stated above, the group $R_5$ can be a protected or unprotected glycosyl moiety, which, in turn, may comprise 1–10 monosaccharide units (e.g., a monosaccharide, a disaccharide, a trisaccharide, etc.). In the present case, the term "monosaccharide" is any sugar residue or derivative thereof. The monosaccharide may, for example, be a hexose (e.g., D-allose, L-allose, D-altrose, L-altrose, D-fucose, L-fucose, D-glucose, L-glucose, D-mannose, L-mannose, D-gulose, L-gulose, D-idose, L-idose, D-galactose, L-galactose, D-rhamnose, L-rhamnose, D-talose, L-talose, and the like, or any deoxy form thereof, e.g., a 2-deoxyhexose, or any amino-substituted derivative thereof, e.g., an aminosugar, such as D-glucosamine, L-glucosamine, D-galactosamine, L-galactosamine, etc.). Furanoses, deoxyfuranoses, amino-substituted furanoses, and the like are also suitable, such as D-ribose, L-ribose, D-arabinose, L-arabinose, D-xylose, L-xylose, D-lyxose, L-lyxose, etc.

Furthermore, the protecting groups for the hydroxyl groups (or amino groups, as the case may be) can be chosen from a wide variety of protecting groups appropriate for a given set of conditions. These protecting groups, the choice of which will be apparent to one skilled in the art, may include, but are not limited to, benzyl, pentenyl, pivaloyl, trimethylsilyl, tert-butyldimethylsilyl, tert-butyldiphenylsilyl, triisopropylsilyl, acetyl, tetrahydropyranyl, benzoyl, $C_1$–$C_3$ alkyl, isopropylidene, benzylidene, trifluoroacetyl, (2-methoxyethoxy)methyl, succinyl, orthoester, paramethoxybenzyl, allyl, and the like.

The acid addition or quaternary ammonium salt of the conjugates of interest are preferably pharmaceutically acceptable. Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

In the present method it is contemplated that the nucleic acid introduced, or at least a portion thereof, leads to its incorporation within the genetic make-up of the cell. Such incorporation may, for example, result in the integration of the nucleic acid, or at least a portion thereof, within a chromosome of the cell. In particular, the segment of nucleic acid may become inserted into a region of a chromosome or may even displace selected endogenous sections thereof. Also, the added nucleic acid, or at least a portion thereof, may be retained by the cell as extrachromosomal material.

In a specific embodiment of the present invention, the method includes contacting the cell with the exogenous or endogenous nucleic acid in the presence of a compound of the formula (I) and, further, in the presence of a lipid or lipids. Preferably, the lipid is polar and, most preferably, is a fusogenic lipid. In the present invention, the term "fusogenic" refers to a property or characteristic that allows the fusogenic material, e.g., a lipid, to promote the fusion of the nucleic acid/bile acid-poly (aminoalkylene)/lipid complex with the cell membrane, such that substances initially located in the exterior of the membrane may eventually penetrate and proceed through to the interior of the membrane. Examples of fusogenic lipids include certain phosphatidylethanolamine head group-containing phospholipid, e.g., DOPE, DMPE. In particular phospholipid compounds, their fusogenic behavior has been correlated with their ability to undergo a bilayer-to-hexagonal phase transition.

The present invention is not limited to the use of such compounds, however, and any lipid that displays fusogenic behavior may be used herein. For example, lysophospholipids, such as lysinyl phosphatidylethanolamine may also promote the fusion of DNA-bile acid amine-lipid complexes. Other general classes of lipids, in addition to phospholipids, lysophospholipids, and fatty acid esters or ethers of sugars, include glycosyl diacylglycerols (e.g., monogalactosyl-diglyceride), plasmalogens (e.g., ethanolamine plasmalogen), glycosphingolipids, including cerebrosides, gangliosides, sterols, and diphosphatidylglycerols (e.g., cardiolipin-$Ca^{2+}$). Several of these classes of lipids contain members known to form either hexagonal phases or micellar structures.

In still other embodiments, a cationic lipid may also be present in the composition. Hence, lipids bearing quaternary ammonium groups are also contemplated for use in the present invention. Accordingly, examples of cationic lipids include, but are not limited to, N-[1-(2,3-dioleoyloxy) propyl]-N,N,N-trimethyl ammonium chloride (DOTMA), 1,2-dimyristoyl-3-trimethylammonium propane (DOTAP), and 1,2-dimyristoyl-3-dimethylammonium propane (DODAP).

General groups of neutral lipids suitable for use in the present invention include, but are not limited to, phospholipids such as DOPE, lysophospholipids such as L-PE, and fatty acid esters such as sucrose monooleate and sucrose monolaurate. Other general groups of potential use in the present invention are glycosyl diacylglycerols, plasmalogens, aphingomyelins, gangliosides, glycerolipids, sphingolipids or cardiolipins.

In a particular embodiment, a fusogenic lipid with a net neutral charge (e.g., DOPE) is optionally combined with a net positive charge (e.g., DOTMA) and subsequently added to a mixture of a compound of the present invention and the nucleic acid or acids of interest. In specific embodiments of the invention, the contacting step is carried out further in the presence of diethylaminoethyldextran (DEAE) or the like.

Further, it may be desirable in some instances to pre-mix the neutral lipid and the compound of the formula (I) with the nucleic acid to allow for the formation of a complex between the nucleic acid and the compound. The resulting mixture is then allowed to contact the cell into which the nucleic acid is to be transformed or introduced.

Thus, the present invention is also directed to a particular group of compounds. Indeed compounds of the formula (I) are disclosed in which $R_1$ can be an H, OH, $OR_5$, $NH_2$, $NHR_6$ or $NR_6R_7$; $R_2$ and $R_3$ may be the same or different and can be an H, OH or $OR_5$; $R_4$ can be $CONHR_6$, $CONR_6R_7$; $CH_2NHR_6$, $CH_2NR_6R_7$, $CO_2$—Y—$NH_2$, $CO_2$—Y—$NHR_6$, or $CO_2$—Y—$NR_6R_7$; $R_5$ is a protected or unprotected glycosyl moiety comprising 1–10 monosaccharide units in which the glycosidic linkage at the anomeric carbon atom of each monosaccharide unit is independently alpha or beta; $NH_2$, $NHR_6$, and $NR_6R_7$ represent an unsubstituted amino group, a monosubstituted amino group, and a disubstituted amino group, respectively, in which $R_6$ and $R_7$ may be the same or different and represent a linear, branched or cyclic hydrocarbon group comprising 1–15 carbon atoms substituted with one or more unsubstituted, monosubstituted or disubstituted amino groups, provided that one of which $R_6$ or $R_7$ must include at least one unsubstituted (preferably, primary) amino group; Y represents a linear or branched alkylene group comprising 1–10 carbon atoms; n is an integer from 0–10, preferably 0–3; or its acid addition or quaternary ammonium salt.

In a specific embodiment, the group $R_1$ has the configuration beta. In another, the group $R_1$ has the configuration alpha. In a particular embodiment, at least one of $R_1$, $R_2$, and $R_3$ represents OH. In another embodiment, at least two of $R_1$, $R_2$, and $R_3$ represent OH, and in still another embodiment, all three of $R_1$, $R_2$, and $R_3$ represent OH.

The present invention contemplates all other combinations of the various groups, including, but not limited to, embodiments in which $R_1$ and $R_2$ represent $OR_5$, and $R_3$ represents OH; $R_1$ and $R_3$ represent $OR_5$, and $R_2$ represents OH; or $R_2$ and $R_3$ represent $OR_5$, and $R_1$ represents OH.

Furthermore, a compound is disclosed in which the group $R_6$ together with the nitrogen atom to which it is attached derives from a polyamine. Suitable polyamines include, but are not limited to, alkylene diamines, such as 1,3-diaminopropane, and biogenic polyamines, such as 1,4-diaminobutane (putrescine), 1,5-diaminopentane (cadaverine), N-(4-aminobutyl)-1,3-diaminopropane (spermidine, an alkylene triamine), and N-[N-(3-aminopropyl)-4-aminobutyl]-1,3-diaminopropane (spermine, an alkylene tetra-amine), and the like, including branched aliphatic polyamines. With unsymmetrical polyamines, the present invention contemplates all other possible points of attachment of the polyamine to the steroid nucleus. For example, in spermidine, any of the three amino groups may be attached to the side chain or at the C-3 position of the steroid nucleus. In selected embodiments of the present invention, the group $R_1$ or $R_4$ is neither an amino acid nor a peptide.

The nucleic acid to be introduced to the cell can comprise DNA or RNA and can take many forms. For example, the nucleic acid may be single-stranded, double stranded (or contain both single-stranded and double-stranded regions, as in a ribozyme), may comprise chromosomes, fragments thereof, plasmids, phage-derived or may be contained in vectors, such as cloning vectors, expression vectors, and yeast artificial chromosomes. Preferably, the nucleic acid encodes a gene and, most preferably, a gene of mammalian or plant origin. In a specific embodiment, the nucleic acid is an oligo- or polynucleotide, preferably an antisense sequence. For example, the antisense sequence may correspond to a splice acceptor site or its complement, e.g., the sequence 5' ACA CCC AAT TCT GAA AAT GG 3' or its complement. Alternatively, the oligonucleotide has a sequence corresponding to a primer binding site or its complement. Such a sequence may include, for example, the sequence 5' AAG TCC CTG TTC GGG CGC CA 3' or its complement.

The preferred steroidal nucleus includes, but is not limited to, bile acids, cholic acid, allocholic acid, 3β- and 3α-amino-5β-cholic acid, lithocholic acid, deoxycholic acid, chenodeoxy cholic acid or 3-deoxycholic acid. Cholestanyl derivatives may also be used but are less desirable, particularly those that may contain negatively charged groups.

Accordingly, the present invention has tremendous promise not only in the areas of gene expression, protein manufacturing, and the like, but also in the diagnostic, prophylactic, and therapeutic areas, particularly in antisense and gene therapies. By enhancing the uptake of transforming nucleic acid, the efficiency of transformation is increased. Consequently, the dosing levels may also benefit from the instant invention.

5.1 Description of Typical Results

Various assays have been performed which confirm the formation of a tight complex between DNA and the compounds of the present invention, the successful transfection of cells, and the expression of the DNA-encoded protein in the transfected cells. Among these assays, the staining assay and the onpg assay both rely on the reporter gene β-galactosidase (β-gal), which is present in the plasmid DNA used for the transformation experiments. The agarose gel assay provides an indication of the efficiency of complex formation.

5.2. Agarose Gel Assay to Evaluate Complex Formation

Typically, it has been found that preferred compounds or mixtures for facilitating uptake of DNA into cells form complexes with DNA. To evaluate the ability of various compounds to complex DNA, an agarose gel assay is used. Compounds that form tight complexes with DNA cause the DNA to be retained in or near the well at relatively low (i.e., less than 10) charge ratios (the charge ratio is the ratio of positive charges in the bile acid conjugates to negative charges in the DNA, assuming complete ionization of all the amine groups of the bile acid conjugates).

In a typical assay, 250–500 ng of pBR322 plasmid DNA are mixed with varying amounts of the bile acid conjugates or mixtures of the bile acid conjugates with other lipids in a total volume of 10 µL and incubated for 30 minutes. To each sample is then added 2 µL of 6× ficoll loading buffer and the samples are loaded on a 1% horizontal agarose gel prepared with 0.5× TBE. Horizontal gel electrophoresis in 0.5× TBE is then carried out for 2–3 hours at 100–125 volts.

The gel is then removed from the electrophoresis chamber and stained with ethidium bromide (5 µg/mL). The gel is placed on a transilluminator and photographed. The composition of the 6× ficoll loading buffer and the TBE running buffer can be found in Sambrook, J.; Fritsch, E. F.; and Maniatis, T., *Molecular Cloning*, Cold Spring Harbor University Press: Cold Spring Harbor, 1989.

A number of compounds and compositions can be tested in this manner, including those listed in Table 1, below.

TABLE 1

Gel Retardation Assay Results

| Compound | 1:1 | Charge ratio DNA:compound 1:2.5 | 1:5 |
| --- | --- | --- | --- |
| A:B 1:1 | partially retarded | partially retarded | fully retarded |
| B alone | partially retarded | partially retarded | fully retarded |
| A:B 1:3 | partially retarded | partially retarded | fully retarded |

TABLE 1-continued

Gel Retardation Assay Results

| Compound | 1:1 | Charge ratio DNA:compound 1:2.5 | 1:5 |
|---|---|---|---|
| A:C 1:1 | no retardation | partially retarded | partially retarded |
| C alone | no retardation | no retardation | no retardation |
| A:D 1:1 | no retardation | no retardation | no retardation |
| D alone | no retardation | no retardation | no retardation |
| A:E 1.25:1 | no retardation | partially retarded | fully retarded |

Key to abbreviations:
Compound A = DOPE (dileoyl phosphtidylethanolamine)
Compound B = Deoxycholic acid-spermine conjugate
Compound C = Deoxycholic acid conjugated, via amide side chain, to: —NHCH$_2$CH$_2$N(CH$_3$)$_3$
Compound D = 3β-amino-7α,12α-di(1'α-glycosyl)-5β-cholic acid, methyl ester
Compound E = Bis(glycosylated)cholic acid-spermine conjugate, via amide side chain

5.3. Materials

Cos-7 and (10)3 cells are cultured in D-MEM with 10% Fetal Bovine Serum (FBS) containing 100 units/mL penicillin G sodium and 100 μg/mL streptomycin sulfate. All cell culture media and components can be purchased from Gibco-BRL. Plasmid pSV40-βGal, obtained from Promega, is amplified in NovaBlue cells (Novagen) and isolated and purified by the alkaline lysis method followed by acidified phenol extraction. Aubin, R.; Weinfeld, M.; Paterson, M. C., Chapter 1 in *Methods in Molecular Biology*, Volume 7: *Gene Transfer and Expression Protocols*, Murray, E. J., ed., Humana Press: Clifton, N.J. 1991.

5.4. Transient Transfection of Cells

Cells are plated the day before transfection in 35 mm wells. The number of cells plated/well is approximately 3×10$^5$. Prior to transfection, the cells are washed three times with phosphate-buffered saline, pH 7.2 (Gibco-BRL). The cells are then overlaid with 1 mL of an Opti-MEM solution (Gibco-BRL) containing 2 μg of pSV40-β-Gal plasmid and varying amounts of the test compounds or compositions (e.g., bile acid-conjugates or a mixture of the bile acid-conjugates and lipid, DOPE). The cells are incubated for 3 hours at 37° C. in a humidified atmosphere containing 5% CO$_2$ and then 1 mL of 20% FBS/D-MEM without added antibiotics is added to each well. The cells are incubated for another 25 hours and then assayed for expression of β-galactosidase.

In experiments summarized in Tables 3 and 4, transfection mixtures contain 1 μg/mL of DNA in a volume of 204 μL. DNA:enhancer mixtures are initially formulated as 5-fold concentrates, incubated for 15 minutes, diluted to their final concentration in Opti-MEM without serum, and then applied to cells. Assays are performed in 11.3 mm wells of a 24-well plate containing 2×10$^4$ cells/well. Cells are exposed to transfection mixtures for 6 hours, after which the transfection mixture is removed. The plates are re-fed with D-MEM containing 10% fetal bovine serum. β-galactosidase expression is examined after 48 hours incubation.

5.5. In Situ Staining of Transfected Cells

Cells are rinsed with PBS and fixed for 10 minutes in 0.5% glutaraldehyde. They are then rinsed twice with PBS and stained overnight in 1 mL of a solution containing: 5 mM K$^+$ferricyanide (Sigma); 5 mM K$^+$ ferrocyanide (Sigma); 1 mM MgCl$_2$, 1 mg/mL X-gal (Boehringer-Mannheim).

Cos-7 cells are treated as described with a 2 μg of pSV40-β-gal DNA in the presence of 6 μL of a 5 mg/mL solution of a 1:1 (w:w) deoxycholate-spermine conjugate:DOPE. The results of the staining assay are summarized in Table 2, below.

TABLE 2

Summary of Qualitative Transfection Efficiency

| COMPOUND | ORIGINAL CONCENTRATION | VOLUME[a] | TRANSFECTION EFFICIENCY |
|---|---|---|---|
| LIPOFECTIN | 1 mg/mL | 4–8 μL | +++++++ |
| A:B 1:1 | 5 mg/mL | 4–8 μL | +++++++ |
| B alone | 2.5 mg/mL | 8 μL | + |
| A alone | 2.5 mg/mL | [b] | – |
| A:E 1.25:1 | 5 mg/mL | 16 μL | +++ |
| A:C 1:1 | 5 mg/mL | [b] | + |
| A:D 1:1 | 5 mg/mL | [b] | – |
| A:B 1:3 | 5 mg/mL | 4–8 μL | ++ |
| A:B 3:1 | 5 mg/mL | 4–8 μL | ++ |
| A:spermine | 5 mg/mL | 12 μL | ++ |

[a]Range in the volume of the solution containing the original concentration found to provide optimal transfection efficiency under the conditions reported above.
[b]The results indicate no obvious difference at all volumes tested.

A separate set of experiments using slightly different conditions is further carried out. The data are presented in Table 3. The data are calculated based on the counted number of transfected cells within either the total complete well, or the average of five 100× fields across the well. Transfections are performed with 1 μg/mL of DNA, and the cells are stained 48 hours following the incubation with DNA. In all cases, the ratio of enhancer to lipid is held at 1:1 (w:w).

TABLE 3

Cell Staining by X-GAL

| Compound | Concentration[a] | % Transfection[b] |
|---|---|---|
| LIPOFECTIN | 8 μg/mL | 100 |
| A | 8 μg/mL | 0 |
| DISTAP:A (1:1) | 8 μg/mL | 32.4 (10.5–59.2) |
| F alone | 16.5 μg/mL | 0.7 (0.09–1.3) |
| F:A (1:1) | 16.5–33 μg/mL | 36.8 (15.0–59.1) |
| G alone | 12.5 μg/mL | 1.0 (0.5–1.4) |
| G:A (1:1) | 12.5 μg/mL | 10.7 (4.8–16.6) |
| E | 36 μg/mL | 0.6 (0.3–0.9) |
| E:A (1:1) | 36 μg/mL | 216 (93–339) |
| B alone | 16.5 μg/mL | 0 |
| B:A (1:1) | 16.5–33 μg/mL | 393.5 (188–599) |

[a]Concentration of each component in transfection mixture to produce highest observed transfection efficiency.
[b]Average of experiments (range) as a percentage of LIPOFECTIN control.
Key to Abbreviations (See, Table 1 for others):
DISTAP = 1,2-Distearoyl-3-trimethylammoniumpropane
E = 3α-Hydroxy-7α,12α-di(1'α-glucosyl)-5β-cholan-24-oic acid, N'-(4,9-diaza-12 aminodecane)amide (same as in Table 1)
F = Cholic acid-spermine conjugate
G = 3α,12α-Dihydroxy-7-deoxy-5β-cholan-24-oic acid, N'-(12-amino-n-dodecyl)amide The data in Tables 2 and 3 demonstrate that the compounds with the spermine side chain (e.g., B, E, and F), when mixed with DOPE and DNA, transfect cells at frequencies that approach, and in some cases, exceed that observed for LIPOFECTIN and cationic:neutral (DISTAP:DOPE) lipid mixtures.

5.6. Assay For Expression Levels, ONPG Assay

Table 4, below, provides the results of this quantitative measure of transfection efficiencies. In this assay, the cells are grown as described for the staining assay (see, Sections 5.3 and 5.4, above) and then treated as follows:

Preparation of cell lysate: The growth medium is removed from the cells to be assayed. The cells are washed twice with PBS buffer. The PBS buffer is removed. To the cells is added enough 1X Reporter Lysis Buffer (Promega) to just cover the cells (~250 µL for a 35 mM culture well). The dish is then incubated at room temperature for 15 minutes. The cell lysate is then transferred to a microfuge tube (a cell scraper is required to loosen all cell debris) with a pipet, and the tube is placed on ice. The tubes from the various wells are then vortexed for 15 seconds and centrifuged at top speed in a microcentrifuge (~14 K rpm) for 2 minutes at 4° C. The supernatant is transferred to a fresh tube and either frozen at −70° C. or used immediately.

Assay of β-gal activity: 150 µL of cell extract is placed in a microfuge tube (as a control, the same amount of cell extract from cells that have not been transfected with the β-gal gene is placed in another tube). 150 µL of Assay 2× Buffer (Promega) is added to the tube. The Assay 2× Buffer contains ONPG, which is a substrate for β-gal. The sample is vortexed and incubated at 37° C. for 30 minutes. The reaction is stopped by adding 500 µL of 1M sodium carbonate and vortexing. The absorbance is then read at 420 nm against the cell extract. In order to determine the β-gal activity, the absorbance is multiplied by 380 and divided by the incubation time (in minutes). 1 U=1 nmol of ONPG hydrolyzed/min at 37° C. (One can also make a calibration curve using a pure preparation of β-galactosidase.)

TABLE 4

| | | Units of β-Galactosidase | | |
|---|---|---|---|---|
| Composition (µL)* | | Exp. 1 | Exp. 2 | Exp. 3 |
| LIPOFECTIN | (4) | 7.06 | 3.04 | 3.08 |
| LIPOFECTIN | (7) | 6.25 | 7.8 | 5.39 |
| A:B 1:1 | (4) | 27.217 | 9.67 | — |
| A:B 1:1 | (8) | 4.638 | 4.2 | 7.47 |
| A:B 1:3 | (2) | 1.71 | | |
| A:B 1:3 | (4) | 0.953 | | |
| A:B 3:1 | (8) | 0.684 | | |
| A:B 3:1 | (16) | 0.98 | | |

*The original concentrations used are the same as those shown in Table 2, above

Table 4 shows that A:B 1:1 is better than LIPOFECTIN (which is a 1:1 mixture of DOTMA and DOPE) in effecting transformation of cells. There is variability between assays but the general trends hold up and are consistent with the staining results.

Under slightly different conditions, the ONPG assay is again used to determine relative β-galactosidase activity as a measure of transfection efficiency. The data presented in Table 5 are determined by in situ analysis of the wells of the 24-well transfection plates. Cells are rinsed three times with PBS and freeze-thawed three times in distilled water. The β-galactosidase activity of the lysates is determined by the addition of an equal volume of substrate mixture that gives a final concentration of 0.88 mg/mL ONPG, 1 mM $MgCl_2$, 45 µM β-mercaptoethanol, in 100 mM sodium phosphate buffer pH 7.5. The assay plate is incubated at 37° C. for 30–60 minutes. A 100 µL aliquot of the reaction mixture is transferred to a 96-well plate. The 96-well plate is read in a microplate reader at 420 nm. A calibration curve of β-galactosidase, incubated with the 24-well plates, is included on the 96-well plate. The β-galactosidase activity is determined from the equation derived by linear regression of the calibration curve.

TABLE 5

| Relative Activity of β-galactosidase | | |
|---|---|---|
| Compound | Concentration[a] | Rel. Enzyme Activity (%)[b] |
| LIPOFECTIN | 8 µg/mL | 100 |
| DISTAP:A (1:1) | 8 µg/mL | 37.5 (16.4–84.2) |
| F alone | 2.2 µg/mL | 12.9 (10.4–15.4) |
| F:A (1:1) | 11–22 µg/mL | 36.4 (26.5–46.3) |
| G alone | 16.7 µg/mL | 3.1 (2.9–3.4) |
| G:A (1:1) | 8.3–16.7 µg/mL | 12.5 (11.4–13.6) |
| E | 6–12 µg/mL | 6.9 (3.3–10.6) |
| E:A (1:1) | 24 µg/mL | 126.6 (77.9–175.4) |
| B alone | 11 µg/mL | 17.9 |
| A:B (1:1) | 11–22 µg/mL | 430.4 |

[a]Concentration of each component in transfection mixture to produce highest observed transfection efficiency.
[b]Average of experiments (range) as a percentage of lipofectin control.
The compound abbreviations are identical to those used above.

The data in Tables 4 and 5 demonstrate that the compounds with the spermine side chain (e.g., A, E, and F), when mixed with DOPE and DNA, promote transfection at frequencies that approach, and in some cases, exceed that observed for lipofectin and cationic/neutral (DISTAP:DOPE) lipid mixtures. The relative efficacy found for the various compounds based on the enzyme assay closely parallels those found using the X-gal staining assay. These results suggest that the compounds of the invention primarily increase the number of cells that become transfected. It should be emphasized, however, that the data presented in Tables 4 and 5 have not been optimized and results approaching those observed for the A:B (1:1) experiments are anticipated for the closely related analogs of B, such as E or F, for example.

Thus, the compounds and compositions described herein provide expression levels (and, hence, transfection levels) that meet or exceed those observed for currently available commercial transfection agents. Moreover, it should be pointed out that the compounds and compositions disclosed herein may prove less toxic to the host cells (or to individuals, organs, tissues, etc.) relative to currently available agents.

As a further illustration of the present invention, examples of preferred embodiments are presented below.

6. EXAMPLES

6.1. 2,3,4,6-Tetra-O-benzyl-α-D-glucopyranose (2)

Methyl-α-D-glucopyranose (100 g, 0.516 mol) is suspended in benzyl chloride (400 mL, 3.5 mol) with KOH pellets (336 g, 6 mol), and the mixture is stirred using a mechanical stirrer at 120°–130° C. for 3 h, as shown in FIG. 1. The reaction mixture is cooled and water (800 mL) is added to dissolve the crystalline mass, which is extracted with ether (2×200 mL). The combined organic layer is washed with water (2×500 mL) and dried ($Na_2SO_4$). The solvents are removed by vacuum distillation to give the crude methyl 2,3,4,6-tetra-O-benzyl-α-D-glucopyrano-side for the next reaction.

To a stirred solution of above crude compound in glacial acetic acid (700 mL) at 110° C. is added 3N sulfuric acid (120 mL) dropwise during 15 min. After 3 h the reaction mixture is cooled to room temperature and left over night for crystallization of product. The crystals are filtered, washed consecutively with water (4×500 mL) and methanol (2×250 mL), and air dried to afford 2 (115 g, 41% overall two steps) as a white powder (mp 150°–51° C., Lit. 151°–152° C.; See, Perrine, T. D. et al. *J. Org. Chem.* (1967) 32:664). TLC (EtOAC:Hexane 3:7) Rf 0.2. IR (KBr): 3362, 3030, 2911, 2863, 1454, 1357, 1146, 1088 cm$^{-1}$. $^1$H NMR (300 MHz, CDCl$_3$): δ 7.38–7.10 (m, 20H), 5.21 (d, J=3.3 Hz, 1H), 4.98–4.44 (m, 9H), 4.25 (m, 1H), 3.72–3.50 (m, 4H). Anal. Calc. for C$_{34}$H$_{36}$O$_6$: C, 75.53; H, 6.71. Found: C, 75.68; H, 6.80.

6.2. Phenyl 2,3,4,6-Tetra-O-benzyl-1-thio-D-glucopyranoside (3)

To a stirred solution of 2 (108 g, 0.2 mol) and phenyl disulfide (53 g, 0.24 mol) in dichloromethane (500 mL) is added tri-n-butylphosphine (60 mL, 90%, 0.22 mol). After allowing the reaction mixture to stir at room temperature for 15 h, it is poured into a solution of saturated aqueous sodium bicarbonate (600 mL) and stirred for 10 min. The organic layer is separated, washed with water (2×500 mL), dried (Na$_2$SO$_4$) and concentrated. The oily residue is dissolved in hexane (500 mL) and chilled to 0° C. to give compound 3 (75 g, 60%) as a white solid (mp 85°–86° C., Lit. 84°–85° C. for β-thio compound; See, Ferrier, R. J. et al. *Carbohyd. Res.* (1973) 27:55). TLC (EtOAC:Hexane 1:3) Rf 0.6. IR (KBr): 3061, 3030, 2900, 2865, 1584, 1494, 1453, 1358, 1125, 1085, 1070, 1029 cm$^{-1}$. $^1$H NMR (300 MHz, CDCl$_3$): δ 7.70–7.00 (m, 25H), 4.90–4.40 (m, 9H), 3.80–3.40 (m, 6H). Anal. Calc. for C$_{40}$H$_{40}$O$_5$S: C, 75.92; H, 6.38, S, 5.06. Found: C, 75.99; H, 6.39; S, 5.12.

6.3 Phenyl 2,3,4,6-Tetra-O-benzyl-1-thio-D-glucopyranoside S-Oxide (4)

To a stirred cooled (−78° C.) solution of 3 (130 g, 0.2 mol) in dichloromethane (400 mL) is added dropwise over a period of 20 min a solution of mCPBA (74%, 58.31 g, 0.25 mol) in dichloromethane (300 mL). The mixture is stirred and allowed to warm up to −30° C. The mixture is then filtered. The filtrate is washed with saturated aqueous sodium bisulfite (2×300 mL), sodium bicarbonate (2×400 mL), brine (400 mL) and water (2×400 mL). The organic layer is dried (Na$_2$SO$_4$) and concentrated. Flash chromatography (CH$_2$Cl$_2$:EtOAC 9:1) of the residue furnishes sulfoxide mixture 4 (127 g, 95%) as a white solid (mp 120°–122° C.). TLC (EtOH:CH$_2$Cl$_2$ 1:9) Rf 0.3. IR (KBr): 3060, 3030, 2910, 2867, 1495, 1450, 1360, 1210, 1136, 1092, 1049 cm$^1$. $^1$H NMR (CDCl$_3$): δ 7.72–7.14 (m, 25H), 5.12–4.42 (m, 9H), 4.40–3.30 (m, 6H). Anal. Calc. for C$_{40}$H$_{40}$O$_6$S: C, 74.04; H, 6.22; S, 4.93. Found: C, 74.10; H, 6.26; S, 4.99.

6.4. Methyl 3α-p-Methoxybenzoate-5β-cholan-24-oic Acid Ester(5)

A solution of methyl cholate (42.2 g, 0.1 mol), panisoyl chloride (20 mL, 0.133 mol) and DMAP (1 g) in pyridine (500 mL) is stirred and refluxed for 8 h. Additional p-anisoyl chloride (10 mL, 0.67 mol) is added and stirred 12 h. The reaction mixture is concentrated, and the residue is dissolved in dichloromethane (600 mL). The solution is washed consecutively with 1N HCl (2×500 mL) and water (3×500 mL), dried (Na$_2$SO$_4$) and the solvent allowed to evaporate. Crystallization of the residue from EtOAC/hexane (1:1) furnishes 5 (40 g, 72%) as a white solid (mp 179°–180° C.). TLC (EtOAC:Hexane 7:3) Rf 0.7.

6.5. Methyl 3α-p-Methoxybenzoate-7α,12α-di(2',3',4',6'-tetra-O-benzyl-1'α-glucosyl)-5β-cholan-24-oic Acid Ester (6)

Triflic anhydride (30 mL, 0.178 mol) is added to cooled toluene (300 mL, −78° C.) and stirred for 5 min. To this solution, a dried (by azeotropic distillation from toluene) sulfoxide 4 (97 g, 0.1495 mol) dissolved in toluene (300 mL) is added dropwise. After 15 min of stirring, a solution of dried (by azeotropic distillation with toluene) 2,6-di-ter-butyl-4-methyl-pyridine (30.8 g, 0.150 mol) in toluene (100 mL) is added to the reaction mixture and stirred for 10 min at −78° C. To this reaction mixture, dried (by azeotropic distillation with toluene) methyl cholate derivative 5 (33.36 g, 0.06 mol) in CH$_2$Cl$_2$ and toluene (1:1, 200 mL) is added dropwise. The reaction progress is monitored by TLC. The temperature of the reaction mixture is slowly brought to −50° C. (during 45 min) and during this time the spot of 5 on the TLC disappears completely. The reaction mixture is poured into a saturated aqueous solution of sodium bicarbonate (1000 mL) and stirred for 10 min. The organic layer is separated, and the aqueous layer is extracted with dichloromethane (2×100 mL). The combined organic layers is washed with water (3×500 mL), dried (Na$_2$SO$_4$) and concentrated. The residue purified by flash chromatography (EtOAC:Hexane=1:9 to 1:4) to furnish 6 (84 g, 87%) as a white foam (mp 46°–48° C.). TLC (EtOAC:Hexane 1:3) Rf 0.3. IR (KBr): 3084, 3062, 3028, 2936, 2867, 1735, 1707, 1605, 1496, 1453, 1360, 1321, 1275, 1254, 1210, 1165, 1097, 1073, 1030 cm$^{-1}$. $^1$H NMR (CDCl$_3$): δ 7.60–6.70 (m, 43H), 5.95 (d, 1H, J=9 Hz), 4.99 (d, 1H, J=3.6 Hz), 4.93 (d, 1H, J=6 Hz), 4.88–3.29 (m, 31H), 2.68–0.65 (m, 37H). Fab MS: 1624 (M+Na)$^+$. Anal. Calc. for Cl$_{101}$H$_{116}$O$_{17}$: C, 75.71; H, 7.30. Found, C, 75.59; H, 7.31.

6.6. 7α,12α-Di(2',3',4',6'-tetra-O-benzyl-1'α-glucosyl)5β-cholan-24-oic Acid (7)

Figure 2:
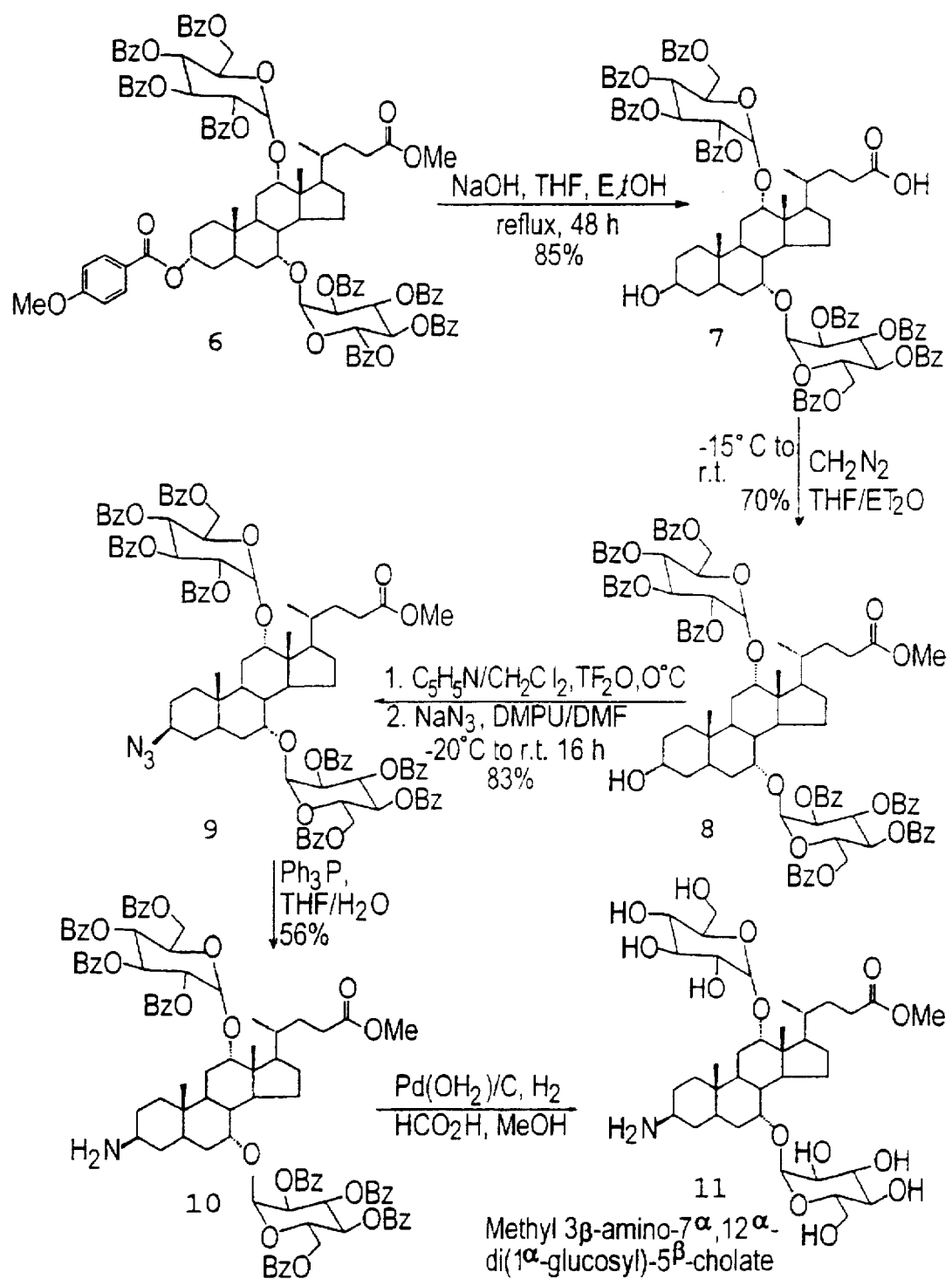
FIG. 2 illustrates the synthetic scheme for the preparation of 3β-amino-7α,12α-di(1'α-glucosyl)-5β-cholan-24-oic acid, methyl ester.

To a stirred solution of 6 (24 g, 15 mmol) in THF (150 mL), NaOH (10 g, 250 mmol) in 95% Ethanol (200 mL) is added and refluxed for 48 h, as shown in FIG. 2. The reaction mixture is then concentrated, and the residue is dissolved in ethyl acetate (300 mL), washed with water (2×250 mL), saturated aqueous sodium bicarbonate (2×300 mL), brine (300 mL) and dried (Na$_2$SO$_4$). Solvent is evaporated and the resulting compound 7 (18.5 g, 85%) is used for the next step without further purification. TLC (EtOAC:Hexane 1:3) Rf 0.4.

6.7. Methyl 7α,12α-Di(2',3',4',6'-tetra-O-benzyl-1'α-glucosyl)-5β-cholan-24-oic Acid Ester (8)

A cooled (−10° C.) solution of diazomethane in ether (100 mL, generated from 5.35 g of diazalid, 25 mmol) is added to a cooled (−10° C.) solution of 7 (18.5 g, 12.74 mmol) in ether (100 mL). After 1 h, excess diazomethane is destroyed by adding glacial acetic acid (2 mL). The reaction mixture is washed consecutively with saturated aqueous sodium bicarbonate (2×400 mL), brine (300 mL), and water (300 mL), dried (Na$_2$SO$_4$), and concentrated. The residue is purified by flash chromatography (EtOAC:Hexane 3:17) to furnish 8 (13 g, 70%) as a gum. TLC (EtOAC:Hexane 1:3) Rf 0.6. IR (Neat): 3450, 2925, 2866, 1736, 1453, 1362, 1158, 1071, 1030 cm$^{-1}$. $^1$H NMR (CDCl$_3$): 7.40–6.50 (m, 40H), 5.10–3.40 (m, 33H), 2.40–0.71 (m, 38H). Anal. Calc. for C$_{93}$H$_{110}$O$_{15}$: C, 76.08; H, 7.56. Found : C, 74.79; H, 7.50.

6.8. Methyl 3β-Azido-7α,12α-di(2',3',4',6'-tetra-O-benzyl-1'α-glucosyl)-5β-cholan-24-oic Acid Ester (9)

To a cooled (0° C.) solution of methyl cholate derivative 8 (13 g, 8.87 mmol) and pyridine (2.5 mL, 31 mmol) in dichloromethane (50 mL), triflic anhydride is added and allowed to stir for 20 min. To this mixture, a solution of sodium azide (2.6 g, 40 mmol) in DMF/DMPU (1:1, 250 mL) is then added at −20° C. The reaction mixture is allowed to warm up to room temperature, where it is stirred overnight. The solvents are evaporated, and the residue is dissolved in dichloromethane (200 mL), washed with water (3×200 mL), dried (Na$_2$SO$_4$), and concentrated. Flash Chromatography of the residue on silica (EtOAC:Hexane 3:17) furnishes 10 g (75% ) of 9 as a white solid (mp 112°–114° C.). TLC (EtOAC:Hexane 1:4) Rf 0.6. IR (KBr) : 3085, 3061, 3029, 2921, 2867, 2097, 1735, 1603, 1495, 1452, 1360, 1256, 1207, 1160, 1091, 1071, 1031 cm$^{-1}$. $^1$H NMR (CDCl$_3$): δ 7.37–6.84 (m, 40H), 5.15 (d, 1, J=4 Hz), 4.95 (d, 1H, J=4 Hz ), 4.86–4.26 (m, 15H), 4.08–3.40 (m, 16H), 2.60–0.71 (m, 37H). Fab MS: 1515 (M+Na)$^+$. Anal. Calc. for C$_{93}$H$_{110}$O$_{14}$N$_3$: C, 74.76; H, 7.43; N, 2.81. Found: C, 74.84; H, 7.40; N, 2.79.

6.9. Methyl 3β-Amino-7α,12α-di(2',3',4',6'-tetra-O-benzyl-1'α-glucosyl)-5β-cholan-24-oic Acid Ester (10)

A solution of compound 9 (11 g, 7.38 mmol) and Ph$_3$P (5.76 g, 22 mmol) in 90° C. aqueous THF (100 mL) is stirred and refluxed for 48 h. The reaction mixture is concentrated, and the residue is purified by flash chromatograph (CH$_2$Cl$_2$ and then CH$_2$Cl$_2$:EtOH=98:2 to 9:1) to give the 3-amino compound 10 (6 g, 56%) as a white solid (mp 43°–45° C.). TLC (EtOH:CH$_2$Cl$_2$ 1:19) Rf 0.15. IR (KBr): 3418, 2922, 2868, 1736, 1496, 1453, 1362, 1161, 1071, 1032 cm$^{-1}$. $^1$H NMR (CDCl$_3$) δ 7.38–6.84 (m, 40H) , 5.10–3.48 (m, 33H), 2.62–0.70 (m, 37H). Anal. Calc. for C$_{93}$H$_{112}$O$_{14}$N: C, 76.08; H, 7.70; N, 0.95. Found: C, 75.82; H, 7.71; N, 0.89.

6.10. Methyl 3β-Amino-7α,12α-di(1'α-glucosyl)-5β-cholan-24-oic Acid Ester (11)

To a solution of 10 (14.65 g, 10 mmol) in toluene (50 mL) and ethanol (200 mL) is added formic acid (15 mL) and palladium hydroxide (20%) on carbon (15 g). The resulting mixture is stirred for 24 h under a hydrogen atmosphere at 40 psi. TLC indicated incomplete hydrogenolysis. Additional formic acid (4 mL) and catalyst (4 g) is then added, and the hydrogenation reaction allowed to proceed for another 24 h. The reaction mixture is then filtered through sand over a membrane filter and concentrated. The filtrate is then mixed with ethyl acetate to form a precipitate. (Some of the methanol solvent from the hydrogenation reaction may need to be removed.) The filtered precipitate is then dissolved in 25 mL deionized water and freeze-dried. Flash Chromatography gives 2.82 g (38%) of 11 as white foam (mp 170°–172° C., decomp.). TLC (MeOH:CH$_2$Cl$_2$:Isopropylamine 2:2:1) Rf 0.15. IR (KBr): 3450, 2932, 1736, 1595, 1451, 1381, 1151, 1023 cm$^{-1}$. $^1$H NMR (CDCl$_3$): δ 5.05 (d, 1H), 4.80 (d, 1H), 3.91–3.10 (m, 15H), 2.50–0.58 (m, 37H). MS (Fab): 746 (M+H)$^+$. Anal. Calc. for C$_{37}$H$_{63}$O$_{14}$N: C, 59.56; H, 8.52; N, 1.88. Found: C, 54.60; H, 8.47; N, 2.49.

The corresponding 3α-amino compound can be obtained from the 3β-hydroxy starting material similarly. The 3β-hydroxy starting material can be obtained, for example, by treatment of methyl cholate with diethyl azidodicarboxylate in the presence of formic acid and triphenyl phosphine with inversion of stereochemistry to provide the methyl 3β-O-formylcholate, which, subsequently, can be hydrolyzed or manipulated, as needed.

6.11. Methyl 3α-p-Methoxybenzoate-7α,12α-di(1'α-glucosyl)-5β-cholan-24-oic Acid Ester To a solution of 6 (10 mmol; see, above) in toluene (50 mL) and ethanol (200 mL) is added formic acid (15 mL) and palladium hydroxide (20%) on carbon (15 g). The resulting mixture is stirred for 24 h under a hydrogen atmosphere at 40 psi. (Additional formic acid and catalyst can be added, if desired, if TLC analysis reveals that the reaction is incomplete after the initial 24 h reaction period. A second 24 h reaction period can then be initiated.) The reaction mixture is then filtered through sand over a membrane filter and concentrated. The filtrate is then mixed with ethyl acetate to form a precipitate. (Some of the methanol solvent from the hydrogenation reaction may need to be removed.) The filtered precipitate is then dissolved in 25 mL deionized water and freeze-dried. Subjecting the residue to flash column chromatography gives the title compound in ca. 38% yield.

$^1$H NMR (CD$_3$OD): δ 0.71 (s, 3H, 18-H), 0.90 (d, 3H, 21H, J=6.6 Hz), 0.93 (s, 3H, 19-H), 1.0–2.6 (m), 3.2–3.4 (m, 2H), 3.55 (s, 3H, CO$_2$CH$_3$), 365 (m), 376 (s, 3H, anisoyl-4-methyl), 4.83 (d, 1H, anomeric H), 5.02 (d, 1H, anomeric H), 6.87 (d, 2H, anisoyl aromatic, J=9 Hz), 7.92 (d, 2H, anisoyl aromatic, J=9 Hz).

6.12. Synthesis of the Activated Ester of Deoxycholate

Triethylamine (10 mL, 71.2 mmol) is added to a stirred solution of the sodium salt of deoxycholic acid (15 g, 34.7 mmol), N-hydroxysuccinimide (7.5 g, 65.2 mmol), 1-hydroxybenzotriazole hydrate (9.3 g, 68.8 mmol, HOBT) and 1-(3-dimethylaminopropyl)-3-ethylcarbodiimide (13.2 g, 69.3 mmol, EDC) in dichloromethane. The mixture is stirred for 12 h. The reaction mixture is then diluted with water (150 mL) and extracted twice with dichloromethane. The organic layers are combined, dried over MgSO$_4$, filtered, and concentrated under reduced pressure to provide a solid residue. The residue is recrystallized from ethyl acetate-petroleum ether to give 5.5 g (30%) of product. Selected $^1$H resonances: (270 MHz, CDCl$_3$): δ 4.00 (br s, 1H, C12), 3.6 (m, 1H, C3), 1.03 (d, 3H, C17), 0.9 and 0.68 (s, 3H each, angular methyls of steroid).

6.13. Synthesis of the Deoxycholic Acid-Spermine Conjugate

Spermine (0.3 g, 1.18 mmol) is added to a stirred solution of the activated ester of deoxycholate (0.15 g, 0.28 mmol) and triethylamine (0.1 mL, 0.71 mmol) in dichloromethane. The mixture is stirred for 0.5 h and a precipitate is observed. The solids are filtered through a buchner funnel. The filtrate is washed with water (10 mL). The organic layer is concentrated to give a residue (0.18 g). The residue is acidified with methanolic trifluoroacetic acid. The resulting solution is purified by reverse phase chromatography to give 0.14 g (80%) of the steroid-polyamine conjugate. Selected $^1$H resonances: (270 MHz, CD$_3$OD): δ 3.98 (br s, 1H, C12), 3.55 (m, 1H, C3), 3.4 (br t, 2H, spermine methylenes next to amide linkage), 3.0 (br s, 10H, spermine methylenes except those next to amide), 1.03 (d, 3H, C17), 0.9 and 0.68 (s, 3H each, angular methyls of steroid). High resolution mass spectrometry has confirmed the proper molecular weight.

In the same fashion, other non-glycosylated amphiphatic steroidal compounds, including but not limited to cholic acid or chenodeoxycholic acid, may be conjugated to a polyamine molecule, including but not limited to ethylene diamine, diethylene triamine, spermidine, other polyalkylenepolyamines, and the like.

6.14. 3α-Hydroxy-7α,12α-di(1'α-glucosyl)-5β-cholan-24-oic Acid

To a stirred solution of the methylcholate product of Example 6.11, above, (15 mmol) in THF (150 mL) is added NaOH (10 g, 250 mmol) in 95% ethanol (200 mL). The reaction mixture is refluxed for 48 h. The reaction mixture is then concentrated, and the residue is dissolved in ethyl acetate (300 mL), washed with water (2×250 mL), saturated aqueous sodium bicarbonate (2×300 mL), brine (300 mL) and dried (Na$_2$SO$_4$). Solvent is evaporated to provide the glycosteroid acid product in 80% yield. Activation of the carboxylic acid group is carried out as follows.

6.15. Synthesis of the Glycosteroid-Spermine Conjugate via the Activated Acid

Triethylamine (120 μL, 0.8 mmol) is added to a stirred solution of the glycosteroid acid product of Example 6.14 (0.3 g, 0.2 mmol), N-hydroxysuccinimide (72 mg, 0.6 mmol), 1-hydroxybenzotriazole hydrate (112 mg, 0.8 mmol) and 1-(3-dimethylaminopropyl)-3-ethylcarbodiimide (160 mg, 0.8 mmol) in dichloromethane. The mixture is stirred for 12 h. After this time, the reaction mixture is diluted with water (50 mL) and extracted twice with dichloromethane. The organic layers are combined, dried over MgSO$_4$, filtered, and concentrated under reduced pressure to provide a solid residue 0.33 g (96%) of the activated ester.

To a stirred solution of the activated ester (0.15 g, 0.089 mmol) and triethylamine (50 mL, 0.35 mmol) in dichloromethane is added spermine (0.3 g, 0.61 mmol). The mixture is stirred for 0.5 h and a precipitate is observed. The solids are filtered over a buchner funnel. The filtrate is washed with water (10 mL). The organic layer is concentrated to give a residue (0.18 g). The residue is acidified with methanolic trifluoroacetic acid. The resulting solution is purified by reverse phase chromatography to give 0.14 g (85%) of the glycosteroid-polyamine conjugate.

In the same fashion, other glycosylated amphiphatic steroidal compounds, including but not limited to the mono-, di-, or triglycosylated forms (as appropriate) of cholic acid, 7-deoxycholic acid, or chenodeoxycholic acid, may be conjugated to a polyamine molecule, including but not limited to ethylene diamine, diethylene triamine, spermine, spermidine, other polyalkylenepolyamines, and the like.

6.16. Deprotection of the Protected Glycosteroid-Polyamine Conjugate

A hydrogenation flask is charged with a solution of the protected glycosteroid-spermine conjugate (0.11 g, 0.06 mmol; See, above) in a mixture of methanol (20 mL) and benzene (4 mL) or THF, followed by Pd(OH)$_2$ catalyst and formic acid (1 mL) or hydrochloric acid. The reaction mixture is shaken under a hydrogen atmosphere at 50 psi for 40 h. The catalyst is filtered off with Celite®, and the solvent is removed by evaporation under reduced pressure. The product is purified over Sephadex-LH-20 gel, eluting with MeOH, to give the desired glycosteroid-spermine conjugate.

Figure 5:
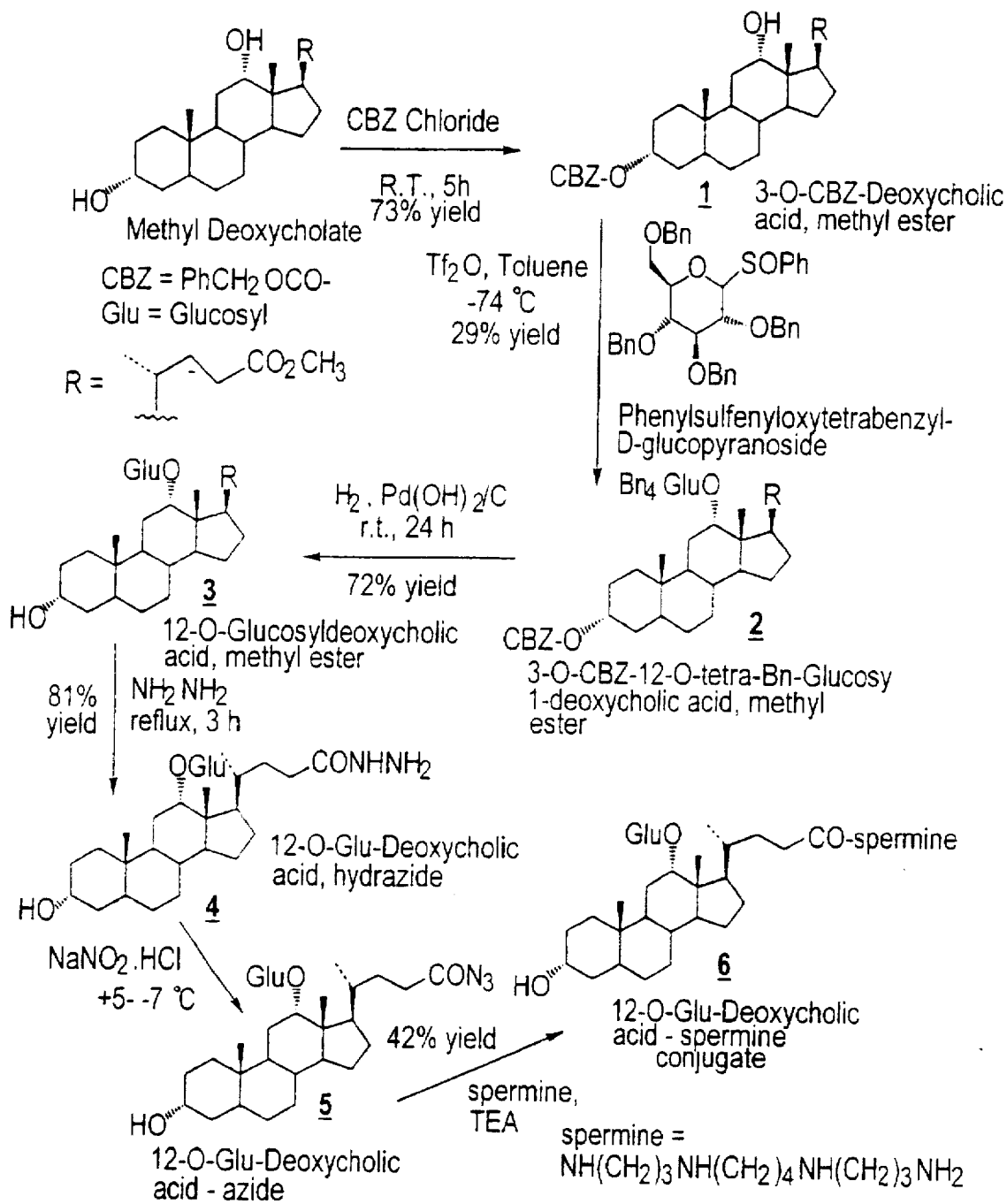
FIG. 5 illustrates the synthetic scheme for the preparation of 3α-hydroxy-7-deoxy-12α-(1'α-glucosyl)-5β-cholan-24-oic acid, N-(4,9-diaza-12-aminododecyl) amide (may also be referred to as the 12-(glycosylated)deoxycholic acid-spermine conjugate).

6.17. Synthesis of the 12α-(O-Glucosyl)deoxycholic Acid-Spermine Conjugate (6, See. FIG. 5)

6.17.1. 3α-O-CBZ-Deoxycholic Acid, Methyl Ester (1)

A mixture of methyldeoxycholate (25 g, 61 mmol), benzylchloroformate (17.0 g, 14 mL, 100 mmol), dimethylaminopyridine (1.22 g, 10 mmol), pyridine (30 mL) and dioxane (150 mL) are stirred at room temperature 3h, the additional amounts of the benzylchloroformate (12.0 g, 10 mL) are added two times in 2 h to complete reaction. Total amount of the benzylchloroformate is 41.0 g (34 mL). The reaction mixture is poured into a separatory funnel, water (500 mL) and ethyl acetate (300 mL) are added. The organic layer is washed with water (500 mL×2), dried over sodium sulfate, concentrated to give an oil. The product is purified on flash chromatography over silica gel (EA-Hexane 1:1 ) providing 24.0 g (73% yield) of compound 1 as a thick oil. TLC (EA:Hexane 2:5) Rf 0.65. IR(near): 3553 (OH), 2943, 2869 (CH), 1742 (C=O), 1453, 1389, 1263 (arom.), 944, 911, 789, 747, 696 cm$^{-1}$. $^1$H NMR (CDCl$_3$): δ 7.38 (s, 5H), 5.15 (s, 2H), 3.6 (s, 3H), 2.0–1.0 (m, 24H), 0.96 (d, 3H, J=6 Hz), 0.86 (s, 3H), 0.65 (s, 3H).

6.17.2. 3α-O-CBZ-12α-(Tetra-O-benzyl-O-glucosyl) deoxycholic Acid, Methyl Ester (2)

Triflic anhydride (2.08 g, 1.26 mL, 7.4 mmol) is added to dry toluene (100 mL), chilled to −75° C. with acetone-dry ice bath, then phenylsulphenyl tetra-O-benzyl-glucopyranoside (glucosulfoxide) (5.06 g, 7.4 mmol) is added dropwise, and in 10 minutes the 2,5-tertbutyl-4-methyl-pyridine, and then 3-O-CBZ-Deoxymethyl cholate 1 is added dropwise. When TLC shows the reaction is finished, it is quenched by sodium bicarbonate (saturated solution, 200 mL) at −25°0 to −30° C. The organic layer is dried over sodium sulfate, concentrated in vacuum at +50°to +60° C. The residue on flash chromatography (EA-Hexane, 20% of EA) affords 2 (1.8 g, 29%), as thick colorless oil. TLC (EA-Hexane 2:5) Rf 0.70. $^1$H NMR(CDCl$_3$): δ 7.3 (m, 24H), 4.4–5.0 (m, 10H), 3.6 (s, 3H), 3.4–4.0 (m, 7H), 1.0–1.95 (m, 40H), 0.92 (d, 3H), 0.82 (s, 3H), 0.56 (s, 3H).

6.17.3. 12α-(O-Glucosyl)deoxycholic Acid, Methyl Ester (3)

The compound 2 (1.6 g, 1.47 mmol) is dissolved in ethyl acetate (15 mL) and ethanol (50 mL) together with catalyst Pd(OH)$_2$/C (500 mg). Using a Parr shaker, the reaction mixture is pressurized under hydrogen at 50 psi for 24 h. The catalyst is filtered off, and the filtrate is evaporated to give a crystalline residue. The residue is purified by flash chromatography (EtOH-DCM 2:8) to afford compound 3 (0.65 g, yield 72%) as white crystals, m.p. 186°–188° C. TLC (EtOH-DCM 2:8) Rf 0.5. IR (neat): 3510, 2943, 2585, 1690, 1452, 1376, 1148, 1090, 1050 cm$^{-1}$. $^1$H NMR: δ 5.05 (d, 1H, J=3 Hz), 3.9 (s, 1H), 3.7–3.8 (m, 3H), 3.6 (s, 3H), 2.2–1.4 (m, 40H), 0.95 (d, 3H), 0.90 (s, 3H), 0.72 (s, 3H).

6.17.4. 12α-(O-Glucosyl)deoxycholic Acid, Hydrazide (4)

The methyl ester 3 (0.6 g, 1.1 mmol) is refluxed in 5 mL of EtOH-hydrazine hydrate (10:1) for 3 h. The solvent is evaporated, water (50 mL) added, then distilled off to remove excess of hydrazine hydrate. The residue is azeotroped with toluene to afford a colorless crystalline hydrazide 4 (0.50 g, yield 81%, m.p. 180°–182° C.). TLC (EtOH-DCM 2:5) Rf 0.15. Anal. Calc. for C$_{30}$H$_{52}$N$_2$)$_8$ N 5.0. Found N 4.81. IR (KBr) 3393, 2907, 2863, 1633, 1543, 1452, 1372, 1144, 1016, 704 cm$^{-1}$.

6.17.5. 12α-(O-Glucosyl)deoxycholic Acid, Azide (5)

Hydrazide 4 (0.5 g, 0.88 mmol) is dissolved in 5 mL of 10% HCl at +1° to +3° C. to give a clear solution. Then NaNO$_2$ (0.14 g, 2.0 mmol) in 5 mL of water is added dropwise at +1° to +5° C. to the reaction mixture to afford a precipitate of the azide 5. This azide is unstable and cannot be isolated in pure form. IR (KBr): 3485–3290, 2928, 2866, 2270, and 2134 (CON$_3$), 1690, 1651, 1451, 1376, 1147, 1031 cm$^{-1}$. TLC (EtOH-DCM 2:5) Rf 0.35.

6.17.6. 12α-(O-Glucosyl)deoxycholic Acid-Spermine Conjugate (6)

The precipitate of azide 5 is fast filtered off through a glass filter with porosity 40–60 μm and washed with ice water (10 mL). While still wet, the precipitate of azide 5 is immediately transferred into a solution of spermine (0.5 g, 2.5 mmol) and triethylamine (0.5 mL) in 10 mL of water. The resulting mixture is stirred for 30 min, then heated up to 60° C. for 10 min, chilled to room temperature, and treated with acetic acid to a pH 4.5–5.0. The clear solution of spermine derivative 6 is purified by flash chromatography using a reverse-phase column CHP 20 in MeOH-Water. The spermine derivative 6 is eluted with a solvent gradient ranging from 50–100% of MeOH. The water-methanol fractions are combined and concentrated. The pH is adjusted to 3.5–3.0 with HCl. The clear solution is lyophilized to afford white, highly hygroscopic, crystalline spermine derivative 6 (0.37 g, yield 42% based on hydrazide 4, 180° C. sinks, 200° C. decomposition). TLC (MeOH-DCM 2:8) Rf 0.1; (MeOH-isopropylamine-DCM 2:2:6) Rf 0.55. IR (KBr): 3450, 2943, 1690, 1452, 1376, 1148, 1091, 950 cm$^{-1}$. $^1$H NMR (D$_2$O): δ 4.95 (d, 1H, J=3 Hz), 3.9 (s, 1H), 3.65 (m, 3H), 3.4 (m, 3H), 3.0 (m, 3H), 1.0–2.4 (m, 60H), 0.95 (d, 3H), 0.90 (s, 3H), 0.62 (s, 3H). Anal. Calc. for C$_{40}$H$_{74}$N$_4$O$_8$·3HCl.10H$_2$O; C 46.7, H 8.91, N 5.45, Cl 10.2. Found: C 56.02, H 8.91, N 5.66, C 9.47. F.W. 739.5. Found: M+Na$^+$ =763.

Figure 6:
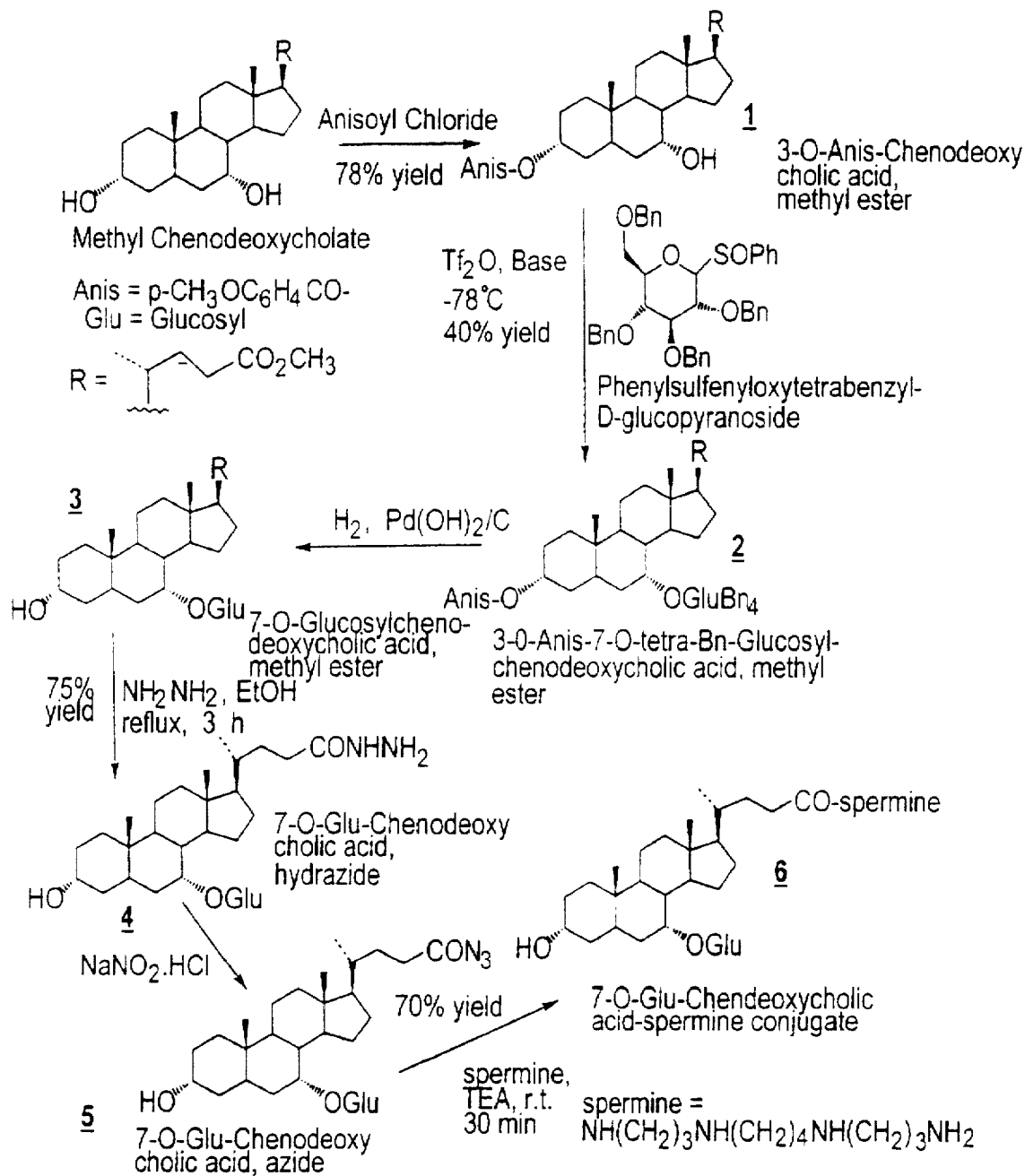
FIG. 6 illustrates the synthetic scheme for the preparation of 3α-hydroxy-12-deoxy-7α-(1'α-glucosyl)-5β-cholan-24-oic acid, N-(4,9-diaza-12-aminododecyl)amide (may also be referred to as the 7-(glycosylated)chenodeoxycholic acid-spermine conjugate).

6.18. Synthesis of the 7α-(O-Glucosyl)chenodeoxy-cholic Acid-Spermine Conjugate (6) (See. FIG. 6)

6.18.1. 3α-(O-Anisoyl)chenodeoxycholic Acid, Methyl Ester (1)

A mixture of methyl chenodeoxycholate (5.0 g, 12.3 mmol), anisoyl chloride (2.3 g, 2.0 mL, 13.5 mmol), dimethylaminopyridine (0.8 g, 6.5 mmol) in pyridine (15 mL) is heated at 100° C. for 3 h. Reaction mixture is poured into a separatory funnel, water (200 mL) and ethyl acetate (300 mL) is added . The organic layer is washed with 5% HCl (100 mL), water (200 mL), sodium bicarbonate, and dried over sodium sulfate. Sometimes a precipitate of the product appears between layers. This precipitate may be filtered off and combined with the product that is obtained after evaporation of ethyl acetate. Total amount is 5.2 g (yield 78%, m.p. 188°–90° C. from EtOH). TLC (EA-Hexane 2:5) Rf 0.6. IR (KBr) : 3513 (OH), 2938, 2851, 1730 ($COOCH_3$), 1712 (Anis-CO), 1607, 1579, 1509, 1451, 1279, 1165, 1100, 963, 770 $cm^{-1}$. $^1$-H NMR ($CDCl_3$): δ 8.03 (d, 2H), 7.96 (d, 2H), 4.85 (s, 1H), 3.85 (s, 3H), 3.65 (s, 3H), 2.0–1.0 (m, 24H), 0.96 (d, 3H), 0.90 (s, 3H), 0.66 (s, 3H).

6.18.2. 3α-(O-Anisoyl)-7α-(tetra-O-benzyl-O-glucosyl) chenodeoxycholic Acid, Methyl Ester (2)

Triflic anhydride (2.1 g, 1.27 mL, 7.4 mmol) is added to dry toluene (100 mL) , chilled up to −72° to −75° C. with acetone-dry ice bath. Phenylsulphenyl glucoside (5.1 g, 7.4 mmol) in 20 mL of dry toluene is added dropwise, then in 10 mins the 2,6-di-tert-butyl-4-methyl-pyridine (1.52 g, 7.4 mmol) in toluene (15 mL) is added, and in 5 min the anisoyl derivate 1 (3.2 g, 5.9 mmol in 30 mL of dry toluene) is added dropwise. When TLC shows the starting material has disappeared, saturated solution of the sodium bicarbonate (150 mL) is poured, and the mixture is transferred into a separatory funnel. The organic layer is washed with water (20 mL), brine (50 mL), dried over sodium sulfate, and concentrated to give a thick oil. It is purified by flash chromatography (EA-Hexane); the product is eluted with 20% ethyl acetate. The product (4.0 g, yield 62%) is obtained as a thick colorless oil. TLC (EA-Hexane 2:5) Rf 0.65. IR (neat): 2950, 2870, 1690, 1745, 1610, 1450, 1275, 1160, 1050, 970, 775 $cm^{-1}$.

6.18.3. 3α-(Anisoyl)-7α-(O-glucosyl)chenodeoxycholic Acid, Methyl Ester (3)

The above obtained oil (4.0 g, 3.7 mmol) is dissolved in ethyl acetate (15 mL) and ethanol (75 mL), together with catalyst (Pd(OH)$_2$/C, 2.0 g). Formic acid (2.0 mL) is added to the mixture. The mixture is set up for hydrogenation in an 0.5 L Parr's apparatus at 50 psi for 24 h. The catalyst is filtered off, and the filtrate is evaporated to give a crystalline residue of 3 (1.8 g, yield 69%), m.p. 258–260° C. (from EtOH), no decomposition. TLC (MeOH-DCM 1:9) Rf 0.35. IR (KBr): 3439 (OH), 2863, 1742 ($COOCH_3$), 1684 (anis. CO), 1606, 1284, 1260, 1022, 967, 773 $cm^{-1}$. $^1$H NMR ($CDCl_3$) : δ 7.9 (d, 2H, J=6 Hz), 6.8 (d, 2H, J=6 Hz), 4.95 (d, 1H, J=3 Hz), 4.75 (s, 1H), 3.80 (s, 3H), 3.58 (s, 3H), 3.3–3.5 (m, 4H), 2.0–1.1 (m, 30H), 0.92 (s, 3H), 0.88 (d, 3H), 0.62 (s, 3H).

6.18.4. 7α-(O-Glucosyl)chenodeoxycholic Acid, Hydrazide (4)

The methyl ester 3 (1.7 g, 3.0 mmol) is refluxed in mixture EtOH-hydrazide hydrate (20 mL+6 mL) for 2 h. The crystals of hydrazide 4 (0.45 g, m.p. 238°–240° C.) that form are separated from solution at room temperature and filtered off. The mother liquid is concentrated, affording an additional amount of hydrazide 4 (0.65 g). Total yield 1.1 g (70%). TLC (MeOH-DCM, 2:8) Rf 0.05. IR(KBr): 3378 (NH, OH), 2927, 1697 (CONH), 1601, 1260, 1020, 980, 770 $cm^{-1}$.

6.18.5. 7α-(O-Glucosyl)Chenodeoxycholic Acid, Azide (5)

Hydrazide 4 (0.8 g, 1.4 mmol) is dissolved in 10 mL 10% HCl, chilled to +3° to +5° C., then $NaNO_2$ (0.21 g, 3 mmol) in 5.0 mL of water is added dropwise affording a precipitate of azide 5. This compound is unstable and cannot be isolated as a pure substance. TLC (EtOH-DCM 2:8) Rf 0.45. IR (KBr): 3490–3300, 2930, 2850, 2260 and 2133 ($CON_3$), 1700, 1640, 1450, 1366, 1147, 1050 $cm^{-1}$.

6.18.6. 7α-(O-Glucosyl)chenodeoxycholic Acid-Spermine Conjugate (6)

The precipitate of azide 5 is fast filtered through a glass filter (porosity 40–60 µm), washed with ice water (5 mL), and while wet is immediately transferred into a solution of spermine (0.5 g, 2.5 mmol) and triethylamine (0.5 mL) in 10 mL of water. The mixture is stirred for 30 min, then is heated up to 60° C. for 10 min, then is chilled to room temperature. The pH is adjusted to 4.5–5.0 using acetic acid. The insoluble impurities are filtered off, and the clear filtrate of spermide 6 is purified by flash chromatography using a reverse-phase column CHP-20. The spermide 6 is eluted with a solvent gradient ranging from 40–100% of MeOH. The water-methanol fractions are combined, evaporated to dryness. Water (10 mL) and conc HCl (0.2 mL) is added, and the clear solution is lyophilized to afford white, highly hygroscopic, crystalline spermide 6 (0.50 g, yield 42% based on hydrazide, m.p. 162–164° C. with decomp.). TLC (MeOH-i-PrOH-DCM 2:2:6) Rf 0.6. IR (KBr): 3447, 2934, 2865, 1652 (CONH), 1457, 1379, 1256, 1026, 772 $cm^{-1}$. $^1$H NMR ($D_2O$) δ 4.85 (d, 1H, J=3 Hz), 3.5–3.8 (m, 8H), 3.5 (m, 6H), 3.1 (m, 2H), 2.9–3.0 (m, 10H), 2.1–1.0 (m, 40H), 0.796 (m, 6H), 0.551 (s, 3H). Anal. Calc. for $C_{40}H_{74}N_4O_8$·3HCl·10$H_2O$. C 46.7, H 9.44, N 5.45, Cl 10.37. Found C 60.8, H 8.97, N 4.60, Cl 6.09. F.W. 847.5. Massspectrum Fab.M-HCl+H$^+$=815. Found: 815.

Figure 7:
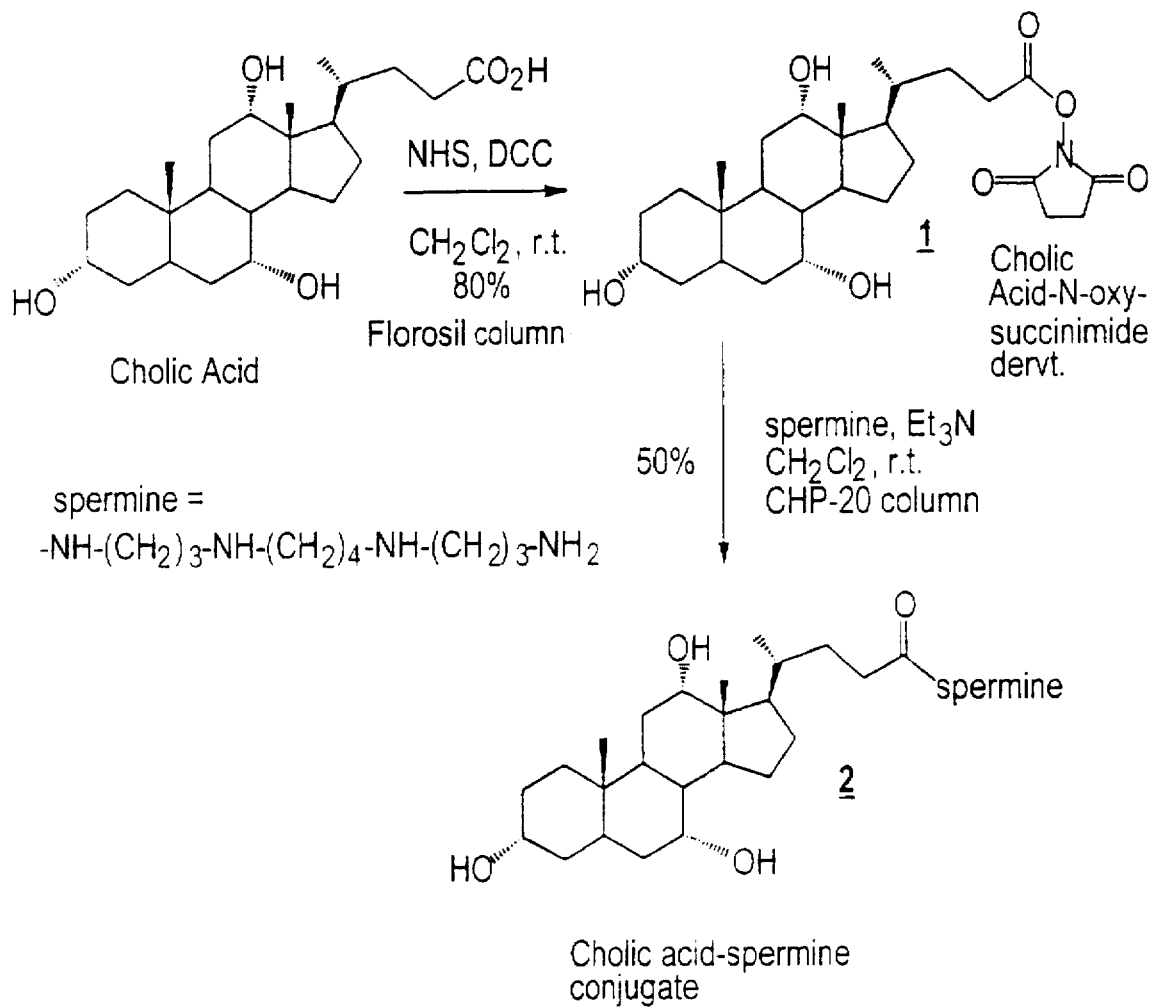
FIG. 7 illustrates the synthetic scheme for the preparation of 3α,7α,12α-trihydroxy-5β-cholan-24-oic acid, N-(4,9-diaza-12-aminododecyl)amide (may also be referred to as the cholic acid-spermine conjugate, Compound F).

6.19. 3α,7α,12α-Trihydroxy-5β-cholan-24-oic Acid, N-Oxysuccinimide (1) (See, FIG. 7)

A mixture of dry cholic acid (8.16 g, 20 mmol), dicyclohexylcarbodimide (4.33 g, 21 mmol) and N-hydroxysuccinimide (2.417 g, 21 mmol) is stirred in dry methylene chloride (200 mL) at room temperature for 6 h. The reaction mixture is filtered, and the filtrate concentrated. The residue is purified by flash chromatography through florosil (EtOH : $CH_2Cl_2$=1:19) giving 8 g (79% yield) of compound 1 as white a foam (mp 92°–95° C.). TLC (EtOH:$CH_2Cl_2$ 1:19) Rf 0.6. IR (KBr): 3385 (br), 2933, 2861, 2118, 1814, 1783, 1738, 1376, 1208, 1073 $cm^{-1}$. $^1$H NMR ($CDCl_3$): δ 3.94 (s, 1H), 3.81 (s, 1H), 3.42 (m, 1H), 2.82 (br, 4H), 2.30–1.00 (m, 24H), 0.99 (d, 1H, J=5.7 Hz), 0.862 (s, 3H), 0.67 (s, 3H). Fab MS: 528 (M+Na)$^+$.

6.19.1. 3α,7α,12α-Trihydroxy-5β-cholan-24-oic Acid, N-(4,9-Diaza-12-amino-dodecyl) amide (2)

To a stirred solution of spermine (303 mg, 1.5 mmol) and triethylamine (1 mL) in anhydrous methylene chloride (20 mL), N-oxysuccinimidocholate 1 (505 mg, 1 mmol) in anhydrous methylene chloride (20 mL) is added dropwise during a 10 min period. The solution is then stirred for 3 h at room temperature. The reaction mixture is filtered and filtrate concentrated.

The residue is purified by flash chromatography using CHP-20 reverse-phase resin (water and then 75% aqueous MeOH), affording 2 (360 mg, 52% yield) as white a foam (mp 140°–145° C.). TLC (MeOH:$CH_2Cl_2$:isopropylamine 4.5:4.5:1) Rf 0.4. IR (KBr): 3350 (br), 2934, 2859, 1685, 1644, 1547, 1449, 1377, 1234, 1207, 1078, 1046 $cm^{-1}$. $^1$H NMR (DMSO-$d_6$ and 2 drops of $D_2O$): δ 3.78 (s, 1H), 3.61 (s, 1H), 3.40–2.80 (m, 9H), 2.42–0.77 (m, 42H), 0.55 (s, 3H). Fab MS: 615 (M+Na)$^+$.

Figure 8:
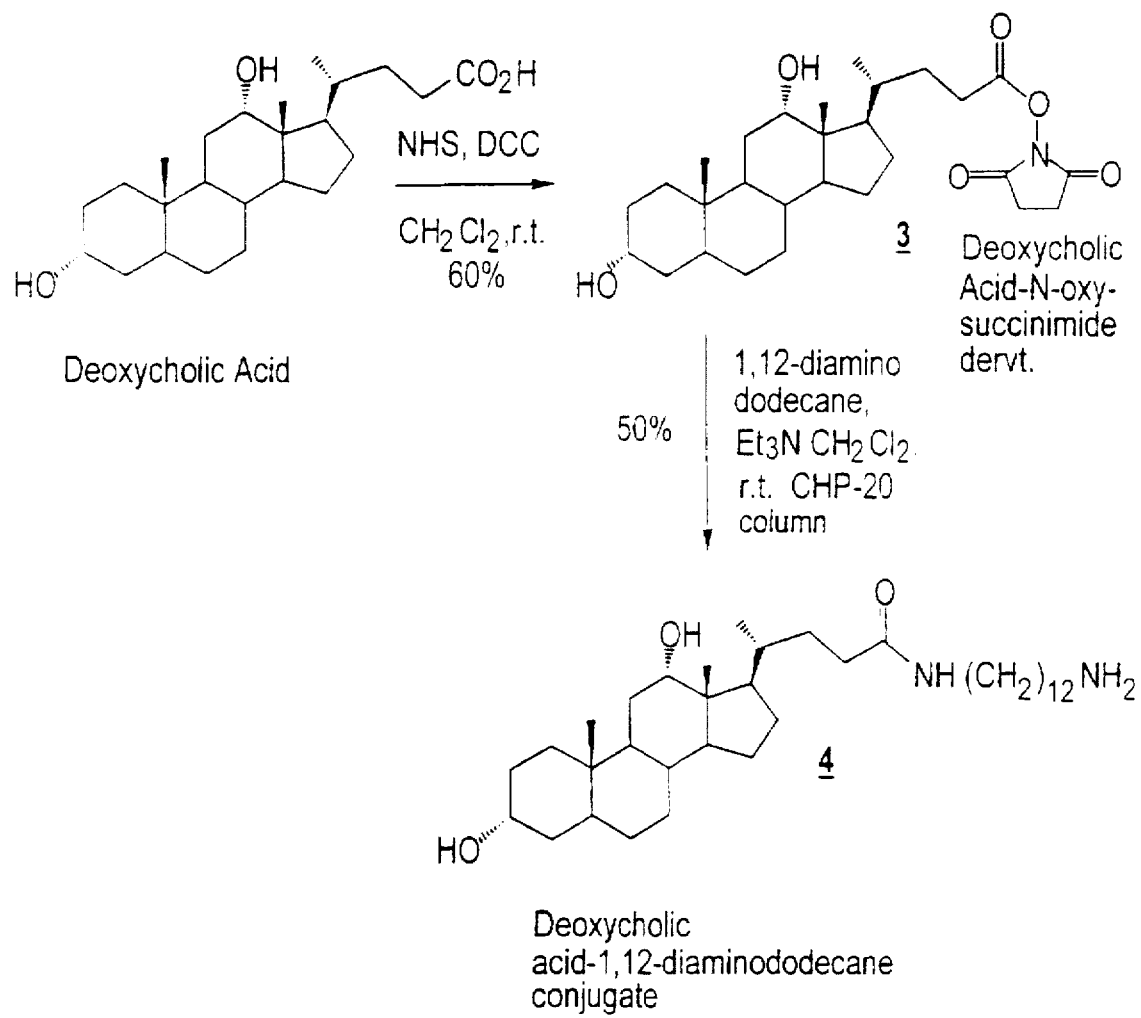
FIG. 8 illustrates the synthetic scheme for the preparation of 3α,12α-dihydroxy-7α-deoxy-5β-cholan-24-oic acid, N-(12-aminododecyl)amide (may also be referred to as the deoxycholic acid-1,12-diaminododecane conjugate, Compound G).

6.20. 3α,12α-Dihydroxy-7-deoxy-5β-cholan-24-oic Acid, N-Oxysuccinimide (3) (See, FIG. 8)

A mixture of dry deoxycholic acid (2.356 g, 6 mmol), dicyclohexeylcarbodimide (1.444 g, 7 mmol) and N-hydroxy-succinimide (0.806 g, 7 mmol) are stirred in dry methylene chloride (200 mL) at room temperature for 6 h. The reaction mixture is filtered, and the filtrate concentrated. The residue is purified by flash chromatography through florosil (EtOH:CH$_2$Cl$_2$ 1:19), affording 1.764 g (60% yield) of compound 3 as white a foam (mp 75°–80° C.). TLC (EtOH:CH$_2$Cl$_2$ 1:9) Rf 0.5. IR (KBr): 3364 (br), 2934, 2862, 1814, 1783, 1738, 1655, 1627, 1449, 1376, 1208, 1068 cm$^{-1}$. $^1$H NMR (CDCl$_3$): δ 3.97 (s, 1H), 3.62 (m, 1H), 2.82 (br, 4H), 2.70–0.83 (m, 30H ), 0.67 (s, 3H). Fab MS: 512 (M+Na)$^+$.

6.20.1. 3α,12α-Dihydroxy-7-deoxy-5β-cholan-24-oic Acid, N-(12-Aminododecane)amide (4)

To a stirred solution of dodecan-1,12-diamine (600 mg, 3 mmol) and triethylamine (1 mL) in anhydrous methylene chloride (25 mL), N-oxysuccinimido-deoxycholate (3) (980 mg, 2 mmol) in anhydrous methylene chloride (25 mL) is added dropwise during 10 minute period. The contents are stirred for 14 h at room temperature. The reaction mixture is filtered, and the filtrate concentrated. The residue is purified by flash chromatography using CHP-20 reverse-phase resin (20%, 40%, 60%, 80% aqueous MeOH and then MeOH) to give 7 (575 mg, 50% yield) as white a foam (mp 118°–120° C.). TLC (MeOH:CH$_2$Cl$_2$:isopropylamine 4.5:4.5:1) Rf 0.8. IR (KBr): 3365 (br), 2928, 2857, 1654, 1647, 1534, 1449, 1376, 1044 cm$^1$. $^1$H NMR (CDCl$_3$): δ 3.97 (s, 1H), 3.62 (m, 1H), 3.21 (q, 1H, J=6.6 Hz), 2.70–1.00 (m, 48H), 0.98 (d, 1H, J=6.0 Hz), 0.90 (d, 1H), 0.67 (s, 3H). Fab MS: 622 (M+2Na)$^+$.

Figure 9:
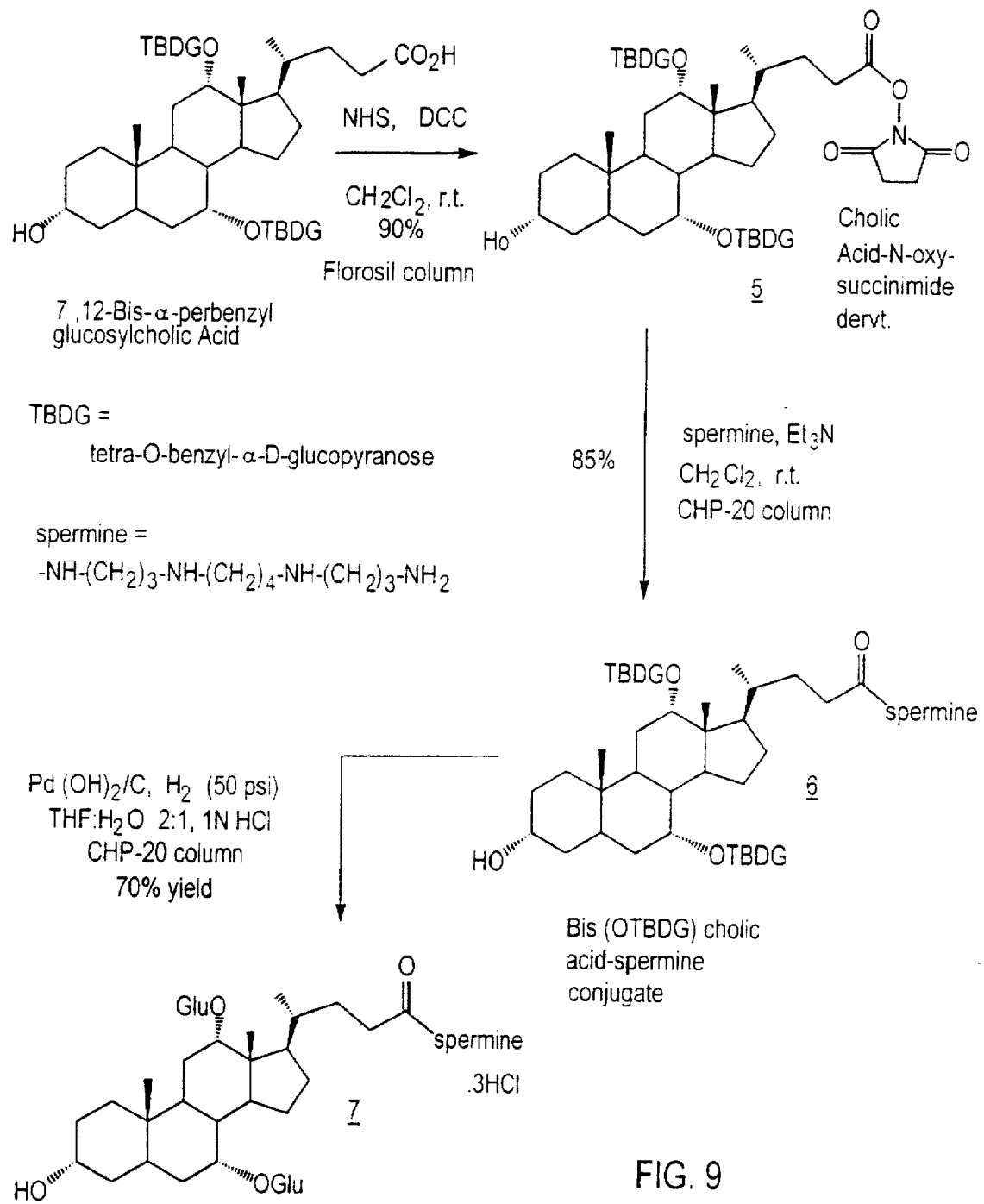
FIG. 9 illustrates the synthetic scheme for the preparation of 3α-hydroxy-7α,12α-di(1'α-glucosyl)-5β-cholan-24-oic acid, N-(4,9-diaza-12-aminododecyl)amide (may also be referred to as the bis(glycosylated)cholic acid-spermine conjugate, Compound E).

6.21. 3α-Hydroxy-7α,12α-Di(2',3',4',6'-tetra-O-benzyl-1'α-glucosyl)-5β-cholan-24-oic Acid, N-Oxysuccinimide (5) (See, FIG. 9)

A solution of dry 7α,12α-di-(2',3',4',6'-tetra-O-benzyl-1'α-glucosyl)-5β-cholan-24-oic acid (1.452 g, 1 mmol), N-hydroxysuccinimide (126 mg, 1.1 mmol) and DCC (226 mg, 1.1 mmol) in dry methylene chloride is stirred at room temperature for 3 h. The reaction mixture is filtered, and the filtrate concentrated. The residue is purified by flash chromatography through a column of florosil (EtOH:CH$_2$Cl$_2$ 1:19) to give 1.40 g (90% yield) of compound 5 as white a foam (mp 63°–65° C.). TLC (EtOH:CH$_2$Cl$_2$ 1:19) Rf 0.5. IR (KBr): 3062, 3030, 2928, 2863, 2117, 1813, 1784, 1740, 1685, 1496, 1453, 1363, 1206, 1070 cm$^{-1}$. $^1$H NMR (CDCl$_3$): δ 7.40–6.90 (m, 40H), 5.10–3.10 (m, 33H), 2.80 (br s, 4H), 2.62–0.84 (m, 30H ), 0.73 (s, 3H). Fab MS: 1572 (M+Na)$^+$.

6.21.1. 3α-Hydroxy-7α,12α-Di(2',3',4',6'-tetra-O-benzyl-1'α-glucosyl)-5β-cholan-24-oic Acid, N-(4,9-Diaza-12-aminododecane) amide (6)

To a stirred solution spermine (0.808 g, 4 mmol) and triethylamine (3 mL) in dry methylene chloride (50 mL), compound 5 (5.16 g, 3.33 mmol) in methylene chloride (50 mL) is added and stirred for 4 h.

The reaction mixture is filtered, and the filtrate is washed with water (2×50 mL), dried (Na$_2$SO$_4$), and concentrated. The residue is purified by flash chromatography through a column of CHP-20 reverse-phase resin (water, then methanol) to afford compound 6 (4.9 g, 85% yield) as white a foam (mp 58°–60° C. ). TLC (MeOH:CH$_2$Cl$_2$:isopropylamine 4.5:4.5:1) Rf 0.2. IR (KBr): 3063, 3030, 2928, 2863, 1655, 1628, 1496, 1452, 1362, 1208, 1147, 1070, 1028 cm$^{-1}$. $^1$H NMR (CDCl$_3$): δ 7.40–6.90 (m, 40H), 6.62 (br s, 1H), 5.03–3.20 (m, 33H), 3.00–0.86 (m, 55H), 0.72 (s, 3H). Fab MS: 1659 (M+Na)$^+$. Anal. Calc. for C$_{102}$H$_{132}$O$_{14}$N$_4$. H$_2$O: C, 74.16; H, 8.19; N, 3.35. Found: C, 73.53; H, 8.24; N, 3.72.

6.21.2. 3α-Hydroxy-7α,12α-di(1'α-glucosyl)-5β-cholan-24-oic Acid, N-(4,9-Diaza-12-aminododecyl)amide (7)

To a solution of compound 6 (2.455 g, 1.5 mmol) and 1N aqueous HCl (25 mL) in THF (50 mL), 20% palladium hydroxide on carbon (2 g, Perlman's catalyst) is added. The mixture is subjected to hydrogenalysis at 50 psi for 6 h. The reaction mixture is filtered through sand and membrane filter and concentrated. The residue is dissolved in water (5 mL) and filtered. The filtrate is purified by flash chromatography through a column of CHP-20 reverse-phase column (water, followed by MeOH:Water 1:9) to give 1.078 g (70% yield) of 7 as a white foam (mp 83°–85° C.). TLC (trifluoroacetic acid:water 1:9) Rf 0.35. IR (Ker): 3365 (br), 2938, 2867, 1638, 1629, 1561, 1545, 1459, 1150, 1075, 1048, 1025 cm$^1$. $^1$H NMR (D$_2$O): δ 5.06 (d, 1H, J=3.6 Hz), 4.85 (d, 1, J=3.6 Hz), 3.95 (br s, 1H), 3.78–2.88 (m, 21H), 2.28–0.76 (m, 46H), 0.64 (s, 3H). Fab MS: 940 (M+Na)$^+$. Anal. Calc. for C$_{36}$H$_{84}$O$_{14}$N$_4$.3HCl.5H$_2$O: C, 49.66; H, 8.52; N, 5.04; Cl, 9.44. Found: C, 49.68; H, 8.60; N, 5.06; Cl, 9.65.

Figure 10:
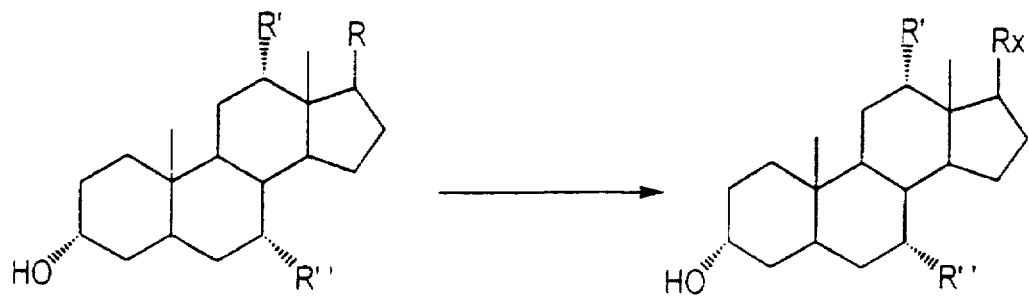
FIG. 10 illustrates additional deoxycholic acid- and chenodeoxycholic acid-poly(aminoalkylene) conjugates of the present invention.

6.22. Preparation of Various Poly (aminoalkylene) Amides of Deoxycholic and Chenodeoxycholic Acids (See, FIG. 10)

6.22.1. 3α,12α-Dihydroxy-7-deoxy-5β-cholan-24-oic Acid, N- (3,6,9-Triaza-11-aminoundecyl)amide (1)

To a solution of tetraethylenepentamine (0.378 g, 2.5 mmol) and triethylamine (0.3 mL) in DMF (5 mL) is added dropwise over 10 min the N-oxysuccinimidodeoxycholate (1.0 g, 2 mmol) in 5 mL of DMF. The solution is stirred overnight at room is temperature, poured into water (20 mL) . The precipitate obtained is washed with cold water (50 mL), dissolved in 10 mL of 2% HCl, and filtered. The solution is poured over a CHP-20 reverse phase column and eluted using a 40–80% MEOH in water solvent gradient system to afford 1.1 g (72% yield) of the trihydrochloride, pentahydrate form of the title compound, as a white powder after lyophilization (m.p. 130°–132° C.) . TLC (MeOH:i-PrNH$_2$:DCM 2:2:6) Rf 0.6. IR (KBr) : 3419, 2934, 1642 (CONH—), 1553, 1454, 1038 cm$^{-1}$. $^1$H NMR (D$_2$O): δ 3.88 (s, 1H), 2.9–3.3 (m, 16H), 1.2–2.4 (m, 42H), 0.88 (d, 3H), 0.78 (s, 3H), 0.55 (m, 3H). Fab MS: 696 (Base.3HCl+Na$^+$). Anal. Calc. for C$_{32}$H$_{61}$N$_5$O$_3$.3HCl.5H$_2$O: C 50.3; H 9.69; N 9.17; Cl 13.95. Found: C 51.5; H 9.04; N 10.1; Cl 10.9.

6.22.2. 3α,12α-Dihydroxy-7-deoxy-5β-cholan-24-oic Acid, N-(3,6,9,12-Tetraaza-14-aminotetradecyl) amide (2)

To a solution of pentaethylenehexamine (0.58 g, 2.5 mmol) and triethylamine (0.3 mL) in DMF (5 mL) is added dropwise over 10 min the N-oxysuccinimidedeoxycholate (1.0 g, 2 mmol) in 5 mL of DMF. The solution is stirred overnight at room temperature, then poured into water (50 mL) to give a precipitate. The liquid phase is decanted. The semi-solid precipitate is washed successively with cold 5% NaOH (10 mL×2) and water (10 mL), dissolved in 10 mL of 10% acetic acid, and purified by flash chromatography through a CHP-20 reverse-phase column using a 40–100%, MeOH in water solvent gradient system. The fractions containing product are combined, evaporated at reduced pressure, dissolved in 2% aqueous HCl solution, and lyophilized to afford 0.75 g (42% yield) of the title compound as a white powder (m.p. 140°–142° C.). TLC (MeOH:i-PrNH$_2$:DCM 2:2:6) Rf 0.65. IR (KBr): 3425, 2932, 1770 (COOH), 1643 (CONH), 1552 (COO$^-$), 1454, 1032 cm$^{-1}$. $^1$H NMR (D$_2$O): δ 3.92 (s, 1H), 2.6–3.6 (m, 20H), 1.0–1.6 (m, 30H ), 0.83 (d, 3H), 0.75 (s, 3H), 0.55 (s, 3H). Fab MS: 863 (M+H$^+$). Anal. Calc. for C$_{34}$H$_{66}$N$_6$O$_3$.2HCl.3AcOH: C 55.8; H 9.28; N 9.70; Cl8.2. Found: C 59.0; H 9.40; N 8.3; Cl 6.6.

6.22.3. 3α,7α-Dihydroxy-12-deoxy-5β-cholan-24-oic Acid, N-(4,9-Diaza-12-aminododecyl) amide (3)

To a solution of spermine (0.8 g, 2 mmol) and triethylamine (0.3 mL) in 5 mL of DMF is added dropwise the N-oxysuccinimidechenodeoxycholate (1.0 g, 2 mmol) in 5 mL of DMF. The mixture is stirred overnight at room temperature, then poured into DCM (100 mL) . The precipitate of the hydroxysuccinimide is filtered, and the filtrate is evaporated to give a liquid phase, which is poured into water (100 mL). The precipitate of the product is obtained. It is dissolved in MeOH (5 mL) and passed through a CHP-20 reverse-phase column. A 30% MeOH in water solvent system is used to elute the product. The solvent is removed by evaporation, and the residue is dissolved in 1 mL of trifluoroacetic acid. The resulting solution is diluted up to 10 mL with water, filtered, and the filtrate subsequently lyophilized to afford 0.9 g (50% yield) of a solid (m.p. 96°–100° C.). The product is soluble in water. A 5% solution of the trifluoroacetate salt of the chenodeoxycholic acid-spermine conjugate is stable at room temperature over about 12–24 h, after which a precipitate of the base separates as a slurry. TLC (MeOH:i-PrNH$_2$:DCM) Rf 0.7. IR (KBr): 3406, 2939, 2869, 1778 (COOH), 1680 (CONH—), 1553, 1458, 1196, 834, 722 cm$^{-1}$. $^1$H NMR (D$_2$O): δ 3.75 (m, 1H), 3.4 (s, 1H) , 2.8–3.15 (m, 12H), 2.2–1.2 (m, 39H), 0.9 (d, 3H), 0.86 (s, 3H) 0.55 (s, 3H). Fab MS: (M+Na$^+$)=598. Anal. Calc. for C$_{34}$H$_{64}$N$_4$O$_3$.3CF$_3$COOH: C52.5; H 7.29; N 6.09. Found: C 53.5; H 7.20; N 4.95.

Figure 11:
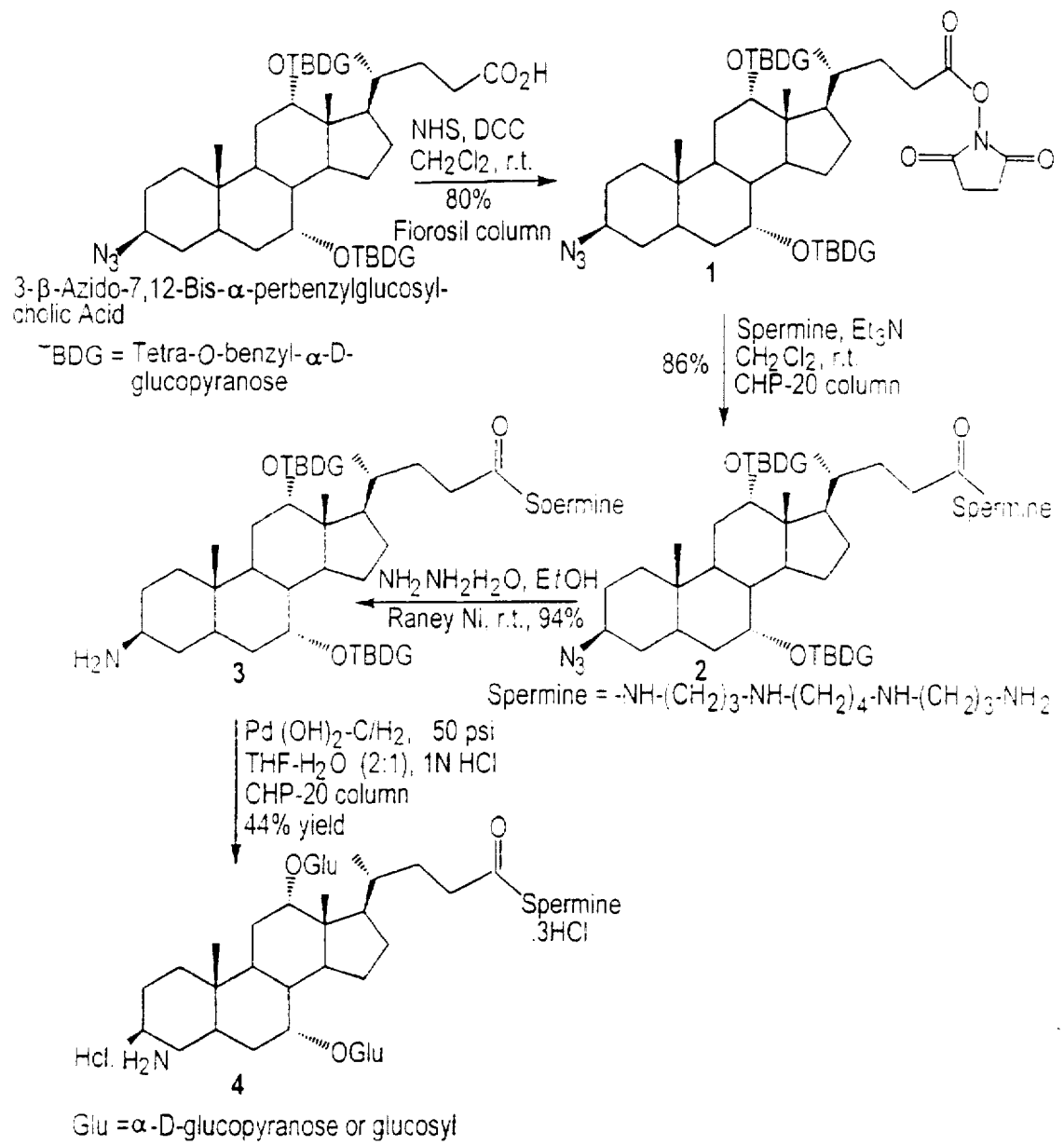
FIG. 11 illustrates the synthetic scheme for the preparation of 3β-amino-7α,12α-di(1'α-glucosyl)-5β-cholan-24-oic acid, N-(4,9-diaza-12-aminododecyl)amide trihydrochloride.

6.23. Preparation of 3β-Amino-7α, 12α-di(1'α-glucosyl)-5β-cholan-24-oic Acid, N-(4,9-Diaza-12-aminododecyl) amide.(HCl) Salt, 4 (See, FIG. 11)

6.23.1. 3αβ-Azido-7α,12α-di(2',3',4',6'-tetra-O-benzyl-1'α-glucosyl)-5β-cholan-24-oic Acid, N-Oxysuccinimide (1)

A solution of dry 3-β-azido-7α,12α-di(2',3',4',6'-tetra-O-benzyl-1'α-glucosyl)-5β-cholan-24-oic acid (4.443 g, 3 mmol), N-hydroxysuccinimide (406 mg, 3.5 mmol) and DCC (722 mg, 3.5 mmol) in dry methylene chloride is stirred at room temperature for 3 h. The reaction mixture is filtered, and the filtrate concentrated. The residue is purified by flash chromatography through a florosil column (EtOAc:Hexane 1:3) to give 4 g (80% yield) of compound 1 as a white foam (m.p. 64°–66° C.). TLC (EtOAc:Hexane 3:7) Rf 0.3. IR (KBr): 3325, 3088, 3062, 3030, 2924, 2867, 2099, 1815, 1785, 1742, 1206, 1070 cm$^{-1}$. $^1$H NMR (CDCl$_3$): δ 7.40–6.90 (m, 40H), 5.02 (q, 2H, J=3.6 Hz), 4.90–3.42 (m, 31H), 2.80 (br s, 4H), 2.62–0.90 (m, 30H ), 0.75 (s, 3H).

6.23.2. 3β-Azido-7α,12α-di(2',3',4',6'-tetra-O-benzyl-1'α-glucosyl)-5β-cholan-24-oic Acid, N-(4,9-Diaza-12-aminododecyl) amide (2)

To a stirred solution of spermine (0.303 g, 1.5 mmol) and triethylamine (3 mL ) in dry methylene chloride (75 mL), compound 1 (1.579 g, 1 mmol) in methylene chloride (75 mL) is added and stirred for 4 h.

The reaction mixture is filtered, and the filtrate is washed with water (2×50 mL), dried (Na$_2$SO$_4$), and concentrated. The residue is purified by flash chromatography through a CHP-20 reverse-phase resin (eluant:water and then methanol) to afford compound 2 (1.46 g, 86% yield) as a white foam (m.p. 60°–62° C.). TLC (MeOH:CH$_2$Cl$_2$: isopropylamine 4.5:4.5:1) Rf 0.5. IR (KBr): 3432 (br), 3087, 3062, 3030, 2925, 2865, 2098, 1670, 1663, 1656, 1640, 1630, 1496, 1452, 1364, 1071, 1028 cm$^{-1}$. $^1$H NMR (CDCl$_3$): δ 7.40–6.90 (m, 40H), 6.30–6.10 (m, 1H), 5.04–3.10 (m, 33H), 2.80–0.83 (m, 55H), 0.73 (s, 3H).

6.23.3. 3β-Amino-7α,12α-di(2',3',4',6'-tetra-O-benzyl-1'α-glucosyl)-5β-cholan-24-oic Acid, N-(4,9-Diaza-12-aminododecyl)amide (3)

To a stirred mixture of 2 (0.999 g, 0.6 mmol) and Raney Ni (500 mg) in ethanol (10 mL) is added dropwise over 10 min a hydrazine hydrate (0.2 mL, 4 mmol) in ethanol (10 mL). The mixture is stirred for 2 h, after which it is filtered. The filtrate is concentrated under vacuum (aspirator pump). The residue is washed with water (3×50 mL) and dried under vacuum to give the 3-amino compound 3 (920 mg, 94%) as a white foam (m.p. 55°–57° C.). TLC (MeOH:CH$_2$Cl$_2$:isopropylamine 4.5:4.5:1) Rf 0.5. IR (KBr): 3415 (br), 3087, 3062, 3029, 2925, 2864, 1669, 1662, 1654, 1647, 1630, 1496, 1453, 1362, 1086, 1070, 1028 cm$^{-1}$. $^1$H NMR (CDCl$_3$): δ 7.40–6.90 (m, 40H), 6.30–6.10 (m, 1H), 5.00–3.00 (m, 33H), 2.80–0.78 (m, 55H), 0.66 (s, 3H).

6.23.4. 3β-Amino-7α,12α-di(1'α-glucosyl)-5β-cholan-24-oic Acid, N-(4,9-Diaza-12-aminododecyl)amide.HCl Salt (4)

To a solution of compound 3 (0.91 g, 0.56 mmol) and 1N aqueous HCl (8 mL, 8 mmol) in THF (25 mL) and water (10 mL) is added 20% palladium hydroxide on carbon (0.9 g, Perlman's catalyst), and the mixture is subjected to hydrogenolysis at 50 psi for 14 h. The reaction mixture is filtered through sand and a membrane filter, then concentrated. The residue is dissolved in water (5 mL) and filtered. The filtrate is purified by flash chromatography through a CHP-20 reverse-phase column (eluant: water, followed by 2% MeOH in water) to give 260 mg (44% yield) of 4 as a white powder (m.p. 125°–127° C.). TLC (trifluoroacetic acid:water 1:9) Rf 0.3. IR (KBr): 3395 (br), 2940, 1640, 1630, 1450, 1150, 1075, 1047, 1023 cm$^{-1}$. $^1$H NMR (D$_2$O): δ 5.09 (br s, 1H), 4.87 (br s, 1H), 3.98 (br s, 1H), 3.78–2.88 (m, 21H), 2.60–1.00 (m, 40H), 0.91 (s, 3H), 0.82 (d, 3H, J=5.1 Hz), 0.66 (s, 3H).

Hence, the present invention also contemplates various compounds selected from non-glycosylated, monoglycosylated, and bis(glycosylated) bile acidpoly (aminoalkylene) or aminoarylene conjugates, including, in particular, 3α,12α-dihydroxy-7-deoxy-5β-cholan-24-oic acid, N-(4,9-diaza-12-aminododecyl)amide (deoxycholic acid-spermine conjugate); 3α-hydroxy-7α,12α-di(1'α-glucosyl)-5β-cholan-24-oic acid, N-(4,9-diaza-12-aminododecyl) amide (bis(glycosylated)cholic acidspermine conjugate); 3α-hydroxy-12α-(1'α-glucosyl)-7-deoxy-5β-cholan-24-oic acid, N-(4,9-diaza-12-aminododecyl) amide (12α-(O-glucosyl)deoxycholic acid-spermine conjugate); 3α-hydroxy-7α-(1'α-glucosyl)-12-deoxy-5β-cholan-24-oic acid, N-(4,9-diaza-12-aminododecyl)amide (7α-(O-glucosyl)chenodeoxycholic acid-spermine conjugate); 3α,7α,12α-trihydroxy-5β-cholan-24-oic acid, N-(4,9-diaza-12-aminododecyl) amide; 3α,7α,12α-dihydroxy-7-deoxy-5β-cholan-24-oic acid, N-(12-aminododecane)amide; 3α-hydroxy-7α,12α-di(2',3',4',6'-tetra-O-benzyl-1'α-glucosyl)-5β-cholan-24-oic acid, N(4,9-diaza-12-aminododecane)amide; 3α-hydroxy-7α,12αdi (1'α-glucosyl)-5β-cholan-24-oic acid, N-(4,9-diaza-12-aminododecyl)amide; 3α,12α-dihydroxy-7-deoxy-5β-cholan-24-oic acid, N-(3,6,9-triaza-11-aminoundecyl) amide; 3α,12α-dihydroxy-7-deoxy-5β-cholan-24-oic acid, N(3,6,9,12-tetraaza-14-aminotetradecyl)amide; 3α,7α-dihydroxy-12-deoxy-5β-cholan-24-oic acid, N-(4,9-diaza12-aminododecyl)amide; 3β- and 3α-amino-7α,12α-di(1'α-glucosyl)-5β-cholan-24-oic acid, N-(4,9-diaza-12-aminododecyl)amide; 3β- and 3α-amino-7α,12αdi(2',3',4',6'-tetra-O-benzyl-1'α-glucosyl)-5β-cholan-24-oic acid, N-(4,9-diaza-12-aminododecyl)amide, intermediates in their syntheses described herein, and their pharmaceutically acceptable salts.

6.24. Preparation of Chenodeoxycholic acid, pentaaminotetraethyleneamide, hydrochloride (H)

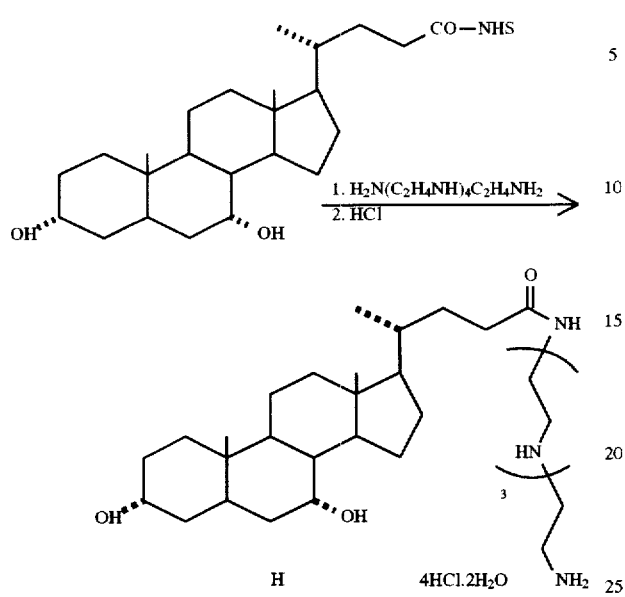

To a solution of the tetraethylenepentaamine base (1.90 g, 10 mmol) and triethylamine (1.0 g, 10 mmol) in 100 ml of DCM, N-(chenodeoxycholoyloxy)succinimide (2.46 g, 5 mmoll) in DCM (dichloromethane, 50 ml) is added and the solution is stirred 48 h at R.T. The reaction mixture is diluted with 100 ml of DCM, washed with water (2×100 ml), dried over sodium sulfate and evaporated to dryness. The residue is dissolved in 25 ml of 10% acetic acid and filtered. The clear filtrate is purified on CHP-20 column in MeOH-water. At 40%–80% of MeOH, the product is eluted. The combined fractions are acidified by 10% HCl (5 ml). The methanol is distilled off under vacuum; the rest of the water solution is lyophilized to give 2.84 g (yield 77%, m.p. 200°–203° C. decomp.) of the pentaaminotetraethyleneamide of the chenodeoxycholic acid. TLC Rf (MeOH:i-PrNH$_2$:DCM) 0.8. IR(KBr): 3350, 2974, 1665, 1635, 1551, 1539, 1460, 1470, 1377, 1077, 978, 766 cm$^{-1}$. $^1$H NMR (D$_2$O): 3.78 (s., 1H), 2.9–3.4 (m, 16H), 1.8–1.2 (m, 39H), 0.85 (d, 3H), 0.76 (s., 3H), 0.55 (s., 3H). Fab MS:(M+H$^+$):564. MS of the chenodeoxycholic acid, pentaaminotetraethylamide is 563. Anal. for C$_{32}$H$_{61}$N$_5$O$_3$·4HCl.2H$_2$O C 51.54; H 9.26; N 9.39; Cl 19.06; Found: C 50.48; H 8.84; N 8.86; Cl 19.7

6.25. Preparation of Chenodeoxycholic acid, hexaaminopentethyleneamide, hydrochloride (I)

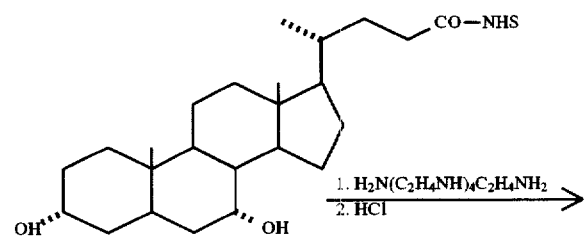

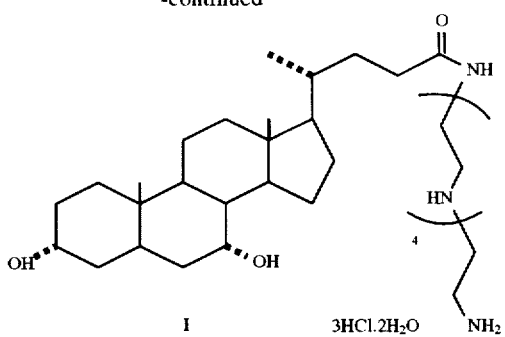

To a solution of the pentaethylenehexamine (2.32 g, 10 mmol) and triethylamine (1.0 g, 10 mmol) in 50 ml of DCM the N-(chenodeoxycholoyloxy)succinimide (2.45 g, 5 mmoll) in DCM (50 ml) is added. A clear solution is stirred at R.T. for 48 h. The reaction mixture is diluted with DCM (150 ml), washed with water (2×100 ml), dried over sodium sulfate, evaporated in vacuum to dryness, the residue is dissolved in 10% acetic acid (25 ml) and is purified on CHP-20 (water-MeOH). At 30%–80% of MeOH the product is run. Combined fractions are acidified by 10% HCl and lyophilized to give 2.1 g, yield 60% of white, hygroscopic powder, m.p. 168°–170° C. TLC, Rf 0.30 (MeOH:i-PrNH$_2$:DCM—1:1:3). IR 3450, 3350, 3267, 2974, 1665, 1649, 1635, 1539, 1460, 1377, 1077, 978 cm$^{-1}$. $^1$H NMR (D$_2$O) 3.78 (s., 1H), 3.2–3.5 (m. 20H), 1.8–1.2 (m., 28H), 0.85 (d., 3H), 0.79 (s. 3H), 0.55 (s., 3H). Fab MS: (M+H$_2$O+ H$^+$) 622. Anal. for C$_{34}$H$_{66}$N$_6$O$_3$ 3HCl.H$_2$O C 55.5; H 9.66; N 11.4; Cl 14.4; Found: C 55.7; H 9.08; N 9.36; Cl 15.6.

6.26. Preparation of Cholic acid, pentaaminotetraethyleneamide, hydrochloride (J)

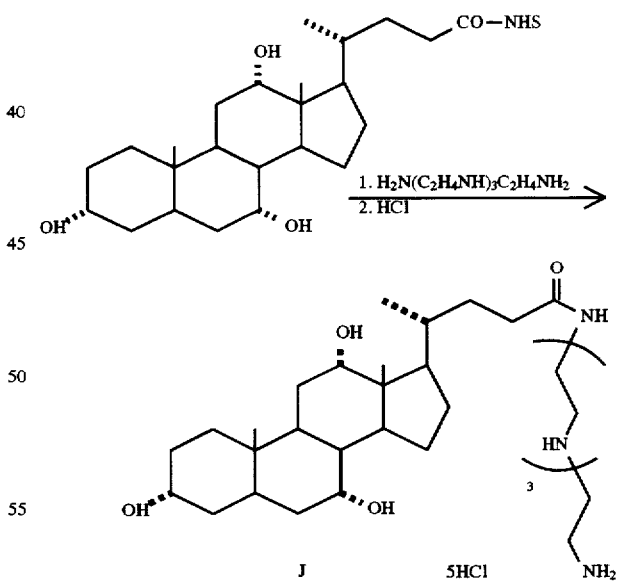

To a solution of the tetraethylenepentamine (0.8 g, 5 mmoll) and TEA (0.3 g, 3 mmol) in DCM (25 ml) the N(Choloyloxy)-succinimide (1.0 g, 2.0 mmol) is added. A clear solution is stirred at R.T. for 48 h, the reaction mixture is diluted with DCM (100 ml), washed with cold water (20 ml), dried over sodium sulfate and evaporated to dryness. The residue is dissolved in 20 ml of 5% AcOH. Purification is carried on CHP-20 reverse phase column in MeOH-water.

The product elutes at 40%–80% of MeOH. The fractions of target compound are combined, methanol is distilled off, and 10 ml of 10% HCl is added. A lyophilization gives 0.70 g (yield 50%) of the pure substance, m.p. 135°–140° C. TLC Rf (MeOH:i-PrNH$_2$:DCM—1:1:3) 0.8. IR(KBr): 3406, 2937, 1640 (C=O), 1556, 1453, 1376, 1023 cm$^{-1}$. NMR $^1$H (D$_2$O): 3.8 (s.1H), 3.65 (s.1H), 3.0–3.3 (m.16H), 2.0–1.1 (m.26H), 0.78 (d.3H), 0.72(s.3H), 0.48 (s.3H). Fab MS: (M+H$^+$) 580. MS is 579. Anal. for C$_{32}$H$_{61}$N$_5$O$_4$.5HCl:Calc. C 50.4; H 8.66; N 9.18; Cl 23.29. Found. C 47.27; H 8.31; N 8.57; Cl 25.63.

6.27. Preparation of Cholic acid, hexaaminopentaethyleneamide, hydrochloride (K)

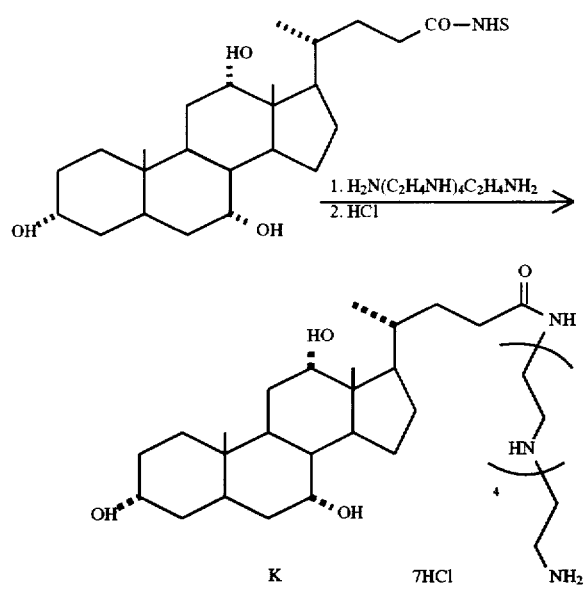

To a solution of the pentaethylenehexamine (0.9 g, 5.5 mmol) and triethylamine (0.3 g, 3 mmol) in DCM (10 ml) the neat N-(Choloyloxy)succinimide (1.0 g, 2.0 mmol) is added at stirring at R.T. The reaction mixture is kept at R.T. for 48 h with stirring. At the end of this period the reaction mixture turns into a semi-solid mixture, which is diluted with 150 ml of DCM, washed with cold water (2×50 ml), dried and distilled to dryness, dissolved in 10 ml of 10% AcOH, filtered from insoluble material, and purified on the reverse-phase column CHP-20 with methanol-water. The product runs at 40–70% of methanol. The combined proper fractions are distilled from methanol, 10 HCl (5 ml) is added. After lyophilization 0.96 g (55% yield) was obtained. M.P. 230° C. (decomp.). TLC, Rf 0.85 (DCM:MeOH:iPrNH$_2$5:1:1). IR: 3393, 2937, 1646 (C=O), 1550, 1483, 1376, 1072, 1028, 774 cm$^{-1}$. $^1$H NMR (D$_2$O) 3.83 (s, 1H), 3.67 (s,1H), 3.1–3.5 (m.21H), 2.0–1.4 (m.26H), 0.78 (d.3H), 0.68 (s.3H), 0.48(s.3H). Fab MS: (M+H$^+$) 623. Anal. Calc. for C$_{32}$H$_{61}$N$_5$O$_4$.5HCl:C 50.4; H 8.66; N 9.18; Cl 23.29. Found:C 47.27; H 8.31; N 8.57; Cl 25.63.

6.28. Preparation of Lithocholic acid, hexaaminopentaethyleneamide, acetate (L)

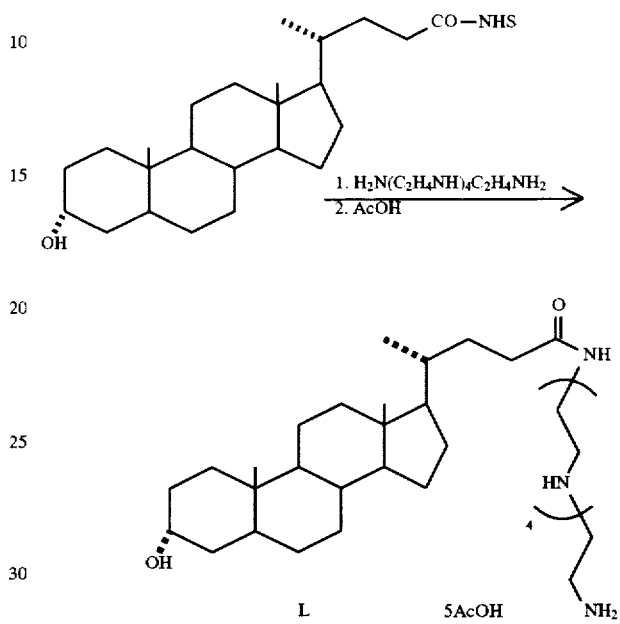

N-(Lithocholoyloxy) succinimide (1.0 g, 2.1 mmol) is added to pentaethylenehexamine (0.73 g, 3.2 mmol) and triethylamine (0.21 g, 2.1 mmol) in DCM (50 ml). The reaction mixture is kept at R.T. with stirring for 48 h., diluted with DCM (100 ml), washed with water (2×100 ml), and dried. The solvent is evaporated. The residue is dissolved in 50 ml of 10% AcOH during 5 h at vigorous stirring. The cloudy solution is set up for purification on reverse phase column in MeOH-water. After a lyophilization 1.1 g (yield 60%) of the product is obtained. M.P. 94° C. TLC, Rf 0.65 (DCM:MeOH:iPrNH$_2$5:1:1). IR (KBr): 3390, 2933, 2862, 1648 (C=O), 1555, 1402, 1075, 656 cm$^{-1}$. NMR $^1$H (D$_2$O) 3.2–2.6 (m. 19H), 1.7–1.0 (m. 29H), 0.70 (s, 6H), 0.42 (s, 3H). Fab MS: (597). Anal. for C$_{34}$H$_{66}$N$_6$O$_2$. 5AcOH Calc. C 59.3; H 9.66; N 9.44. Found. C 58.2; H 9.51; N 10.9.

6.29. Preparation of 3-α-Hydroxy-7α,12α-Di-(2',3',4', 6'-tetra-O-benzyl-1'α-glucosyl)-5β-cholan-24-oic acid-N-[3,6,9,12-tetra-aza-15-amino-pentadecane]-amide (2)

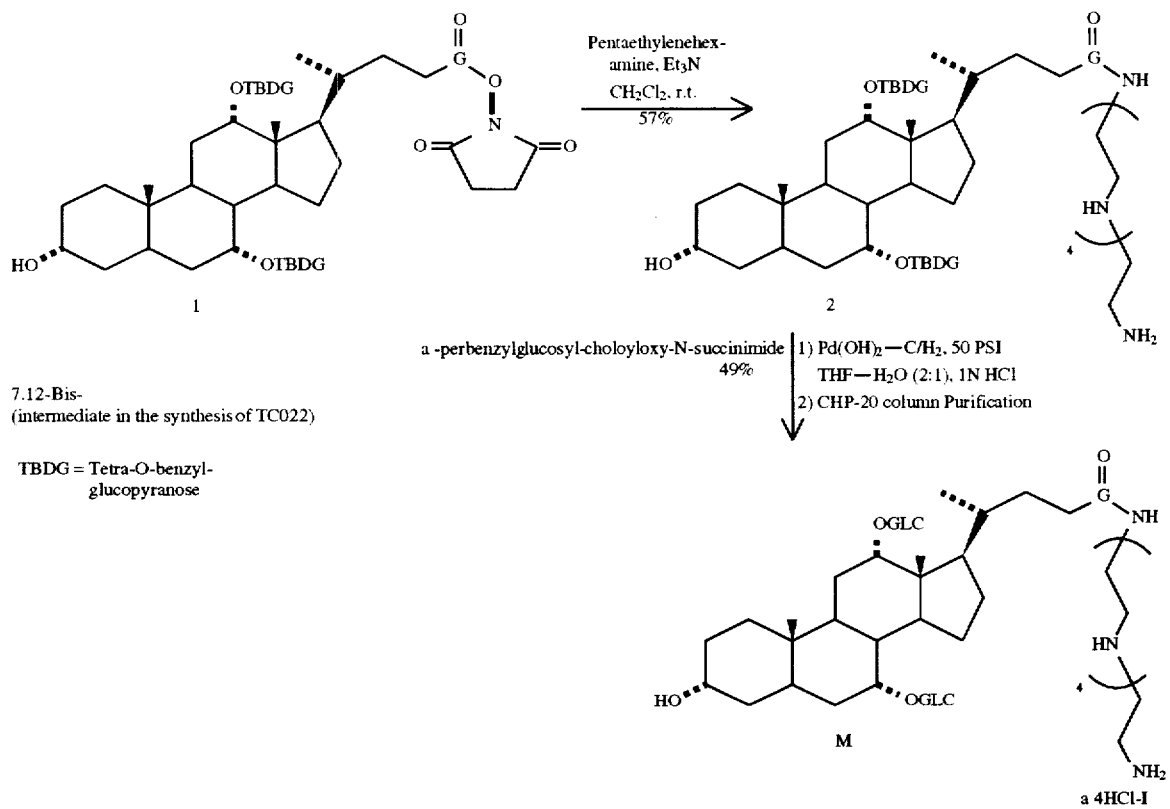

To a stirred solution of pentaethylene-hexamine (367 mg, 1.5 mmol) and triethylamine (2 mL) in dry methylenechloride (50 mL), compound 1 (1.549 g, 1 mmol) in methylenechloride (50 mL) is added dropwise and stirred for 48 h. The reaction mixture is filtered, and the filtrate is concentrated. The residue is purified on flash chromatography over CHP-20 reverse phase resin (eluants, water and then gradually increasing to 90% methanol. Product is obtained from 90% methanol in water fractions, affording compound 2 (950 mg, 57% yield) as white foam (mp 78°–80° C.). TLC Rf (solvent—MeOH:CH$_2$Cl$_2$:isopropylamine=4:4:2) 0.1. IR (KBr): 3500 (br), 3086, 3061, 3030, 2929, 2864, 1699, 1652, 1453, 1363, 1155, 1071, 1028 cm$^{-1}$. $^1$H NMR (CDCl$_3$): δ 7.40–6.90 (m, 40H), 5.03–3.10 (m, 33H), 2.90–0.66 (m, 65H). Fab MS: 1674 (M+Na)$^+$.

6.30. Preparation of 3-α-Hydroxy-7α, 12α, -Di(1'α-glucosyl)-5β-cholan-24-oic acid-N-[3,6,9,12-tetra-aza-15-amino pentadecane]-amide (M, above)

To a solution of compound 2 (333 mg, 0.2 mmol) and 1N aqueous HCl (3 mL, 3 mmol) in THF and water (2:1, 30 mL), 20% palladium hydroxide on carbon (300 mg, Perlman's catalyst) is added and the mixture is subjected to hydrogenalysis at 50 PSI for 15 h. The reaction mixture is filtered through sand and membrane filter and concentrated. The residue is dissolved in water (5 mL) and filtered. The filtrate is purified on flash chromatography over CHP-20 reverse phase column (water, followed by MeOH:Water= 1:19, 1:4 and 2:3; product is found in 20% methanol in water fractions). The procedure provides 110 mg (49% yield) of M as a white foam (mp 180°–82° C.). TLC Rf (solvent—Trifluoroacetic acid: Water 1:9) 0.3. IR (KBr): 3394 (br), 2934, 2867, 1652, 1647, 1636, 1558, 1541, 1027 cm$^{-1}$. $^1$H NMR (D$_2$O): 5.09 (d, 1H, J=3.6 Hz), 4.86 (d, 1H, J=3.6 Hz), 3.95 (brs, 1H), 3.80–2.55 (m, 15H), 2.30–0.65 (m, 56H). Fab MS: 970 (M+Na)$^+$. Anal. Calc. for C$_{46}$H$_{86}$O$_{14}$N$_6$·4HCl: C, 50.55 ; H, 8.30; N, 7.69 ; Cl, 12.97. Found: C, 50.67; H, 8.71; N, 6.70; Cl, 11.65.

6.31. Preparation of 3-α-Hydroxy-7α,12α-Di-(2',3',4',6'-tetra-O-benzyl-1'α-glucosyl)-5β-cholan-24-oic acid-N-[3,6, 9-tri-aza-12-amino-undecane]-amide (4)

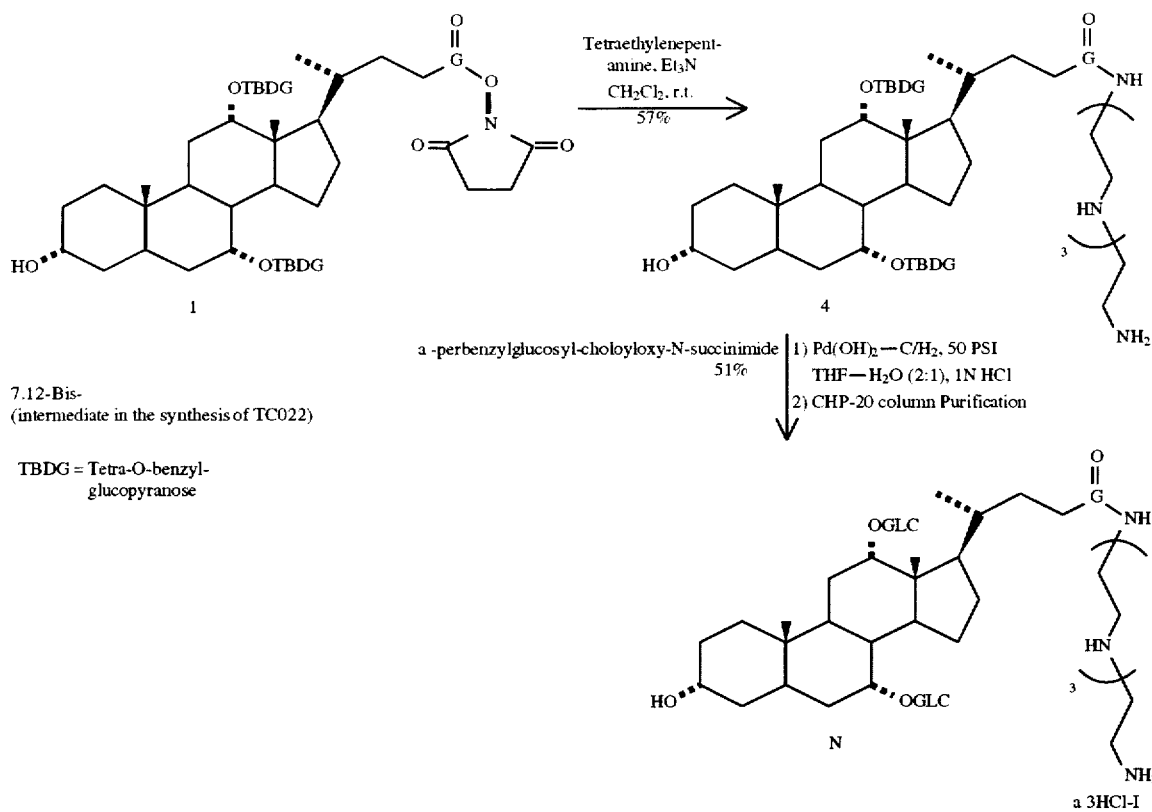

7,12-Bis-
(intermediate in the synthesis of TC022)

TBDG = Tetra-O-benzyl-
glucopyranose

To a stirred solution of tetraethylene-pentamine (285 mg, 1.5 mmol) and triethylamine (2 mL) in dry methylenechloride (50 mL), compound 1 (1.549 g, 1 mmol) in methylenechloride (50 mL) is added dropwise and stirred for 48 h. The reaction mixture is filtered, and the filtrate is concentrated. The residue is purified on flash chromatography over CHP-20 reverse phase resin (eluants: water and then gradually increasing to 90% methanol; product is obtained from 90% methanol in water fractions) affording compound 4 (1 g, 63.8% yield) as white foam (mp 74°–76° C.). TLC Rf (solvent MeOH:CH$_2$Cl$_2$:isopropylamine=4:4:2) 0.1. IR (KBr): 3365 (br), 3086, 3061, 3029, 2925, 2864, 1699, 1653, 1496, 1453, 1155, 1070, 1028 cm$^{-1}$. $^1$H NMR (CDCl$_3$): δ 7.40–6.95 (m, 40H), 5.10–3.20 (m, 33H), 2.82–0.82 (m, 57H), 0.72 (s, 3H). Fab MS: 1651 (M+Na)$^+$.

6.32. Preparation of 3-α-Hydroxy-7α,12α-Di(1'α-glucosyl)-5β-cholan-24-oic acid-N[3,6,9-tri-aza-12-amino-undecane]-amide (N, above)

To a solution of compound 4 (486 mg, 0.3 mmol) and 1N aqueous HCl (4 mL, 3 mmol) in THF and water (2:1, 30 mL), 20% palladium hydroxide on carbon (400 mg, Perlman's catalyst) is added and the mixture is subjected to hydrogenolysis at 50 PSI for 15 h. The reaction mixture is filtered through sand and membrane filter and concentrated. The residue is dissolved in water (5 mL) and filtered. The filtrate is purified on flash chromatography over CHP-20 reverse phase column (water, followed by MeOH:Water= 1:19, 1:4 and 2:3; product is found in 20% methanol in water fractions) gives 160 mg (51% yield) of N as white foam (mp 151°–53° C.). TLC Rf (solvent—Trifluoroacetic acid: Water=1:9) 0.3. IR (KBr): 3390 (br), 2938, 2869, 1652, 1647, 1636, 1541, 1457, 1251, 1150, 1073, 1026 cm$^{-1}$. $^1$H NMR (D$_2$O): 5.09 (br s, 1H), 4.86 (br s, 1H), 4.00 (m, 2H), 3.85–2.60 (m, 16H), 2.30–0.75 (m, 49H) and 0.66 (s, 3H).

Fab MS: 927 (M+Na)$^+$. Anal. Calc. for C$_{44}$H$_{81}$O$_{14}$N$_5$·3HCl: C, 52.14; H, 8.35; N, 6.91; Cl, 10.49. Found: C, 52.41; H, 8.75; N, 5.21; Cl, 9.49.

6.33. Transfection and Assay

CELLS: The day before the transfection assay COS-7 (SV40 transformed African green monkey) cells are plated at 3×10$^4$ cells/well into a 24 well multiwell dish containing DMEM+10% FBS. Just prior to transfection the cells are washed once with serum free Opti-MEM.

TRANSFECTION ASSAY: Test Compound:DOPE (1,2dioleoyl-sn-glycerol-3-phosphethanolamine) complex (1:1) or Lipofectin are mixed together with pSVβ plasmid DNA (5 μg/mL) at appropriate charge ratio to DNA. All solutions are made in serum free Opti-MEM. The mixtures are incubated for 15 minutes at room temperature. The transfection mixtures are diluted to 1 μg/mL DNA with Opti-MEM and added to prewashed COS-7 cells. The COS-7 cells are incubated with the transfection mixtures for 6 hours at 37° C. The transfections mixtures are removed and replaced with DMEM+10% FBS. The cells are incubated for 48 hours at 37° C. then assayed for β-galactosidase activity by either X-GAL or ONPG assays.

ONPG ASSAY: COS-7 cells are washed three times with phosphate buffered saline pH 7.2 (PBS). The cells are lysed in water and frozen and thawed three times. An equal volume of O-nitrophenylpyranogalactoside (ONPG) reagent (1.76 mg/mL ONPG, 2 mM MgCl$_2$, 90 mM β-mercaptoethanol in 100 mM phosphate buffer pH 7.5) is added to either the cell extract or β-galactosidase standards. The mixture is incubated for 30 minutes at 37° C. The absorbance at 410 nm for each mixture is determined and units of β-galactosidase activity determined from a standard curve. Cell extracts are also assayed for protein content by a Bio-Rad protein determination assay. The specific activity of the mU β-galactosidase/mg protein is determined.

X-GAL ASSAY: COS-7 cells are washed three times with PBS then fixed for 15 minutes with 2% formaldehyde+0.2% gluteraldehyde in PBS. The cells are washed three more times with PBS and stained with X-GAL stain (5 mM K$_4$Fe(CN)$_6$, 5 mM K$_3$Fe(CN)$_6$, 2 mM MgCl$_2$, 0.1% X-GAL in PBS). The plates are incubated 24 hours, and the number of stained cells is determined.

6.34 Additional Discussions

Figure 14:
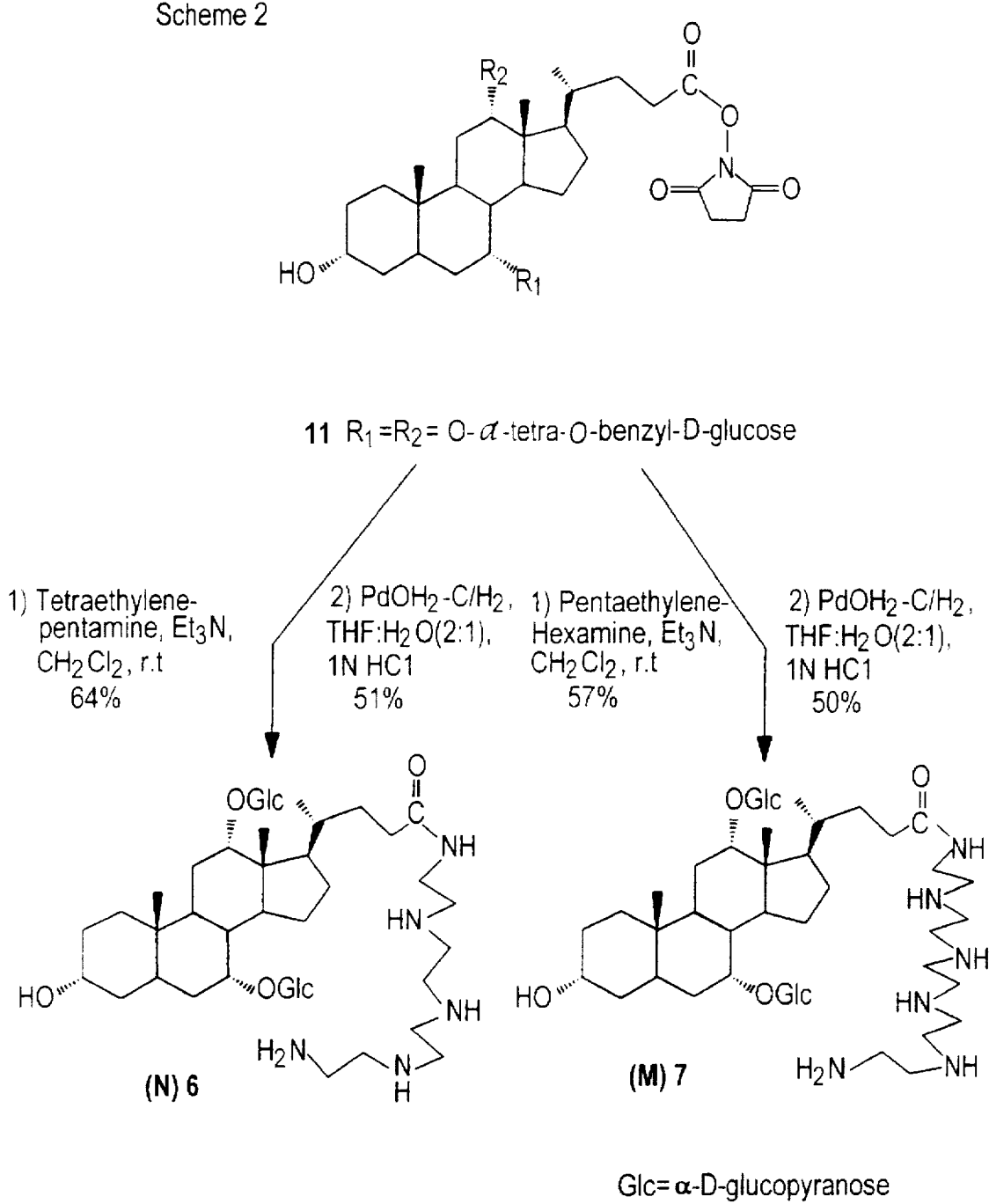
FIG. 14 illustrates the synthetic scheme for the synthesis of compounds 6 and 7 of FIG. 12.
Figure 15:
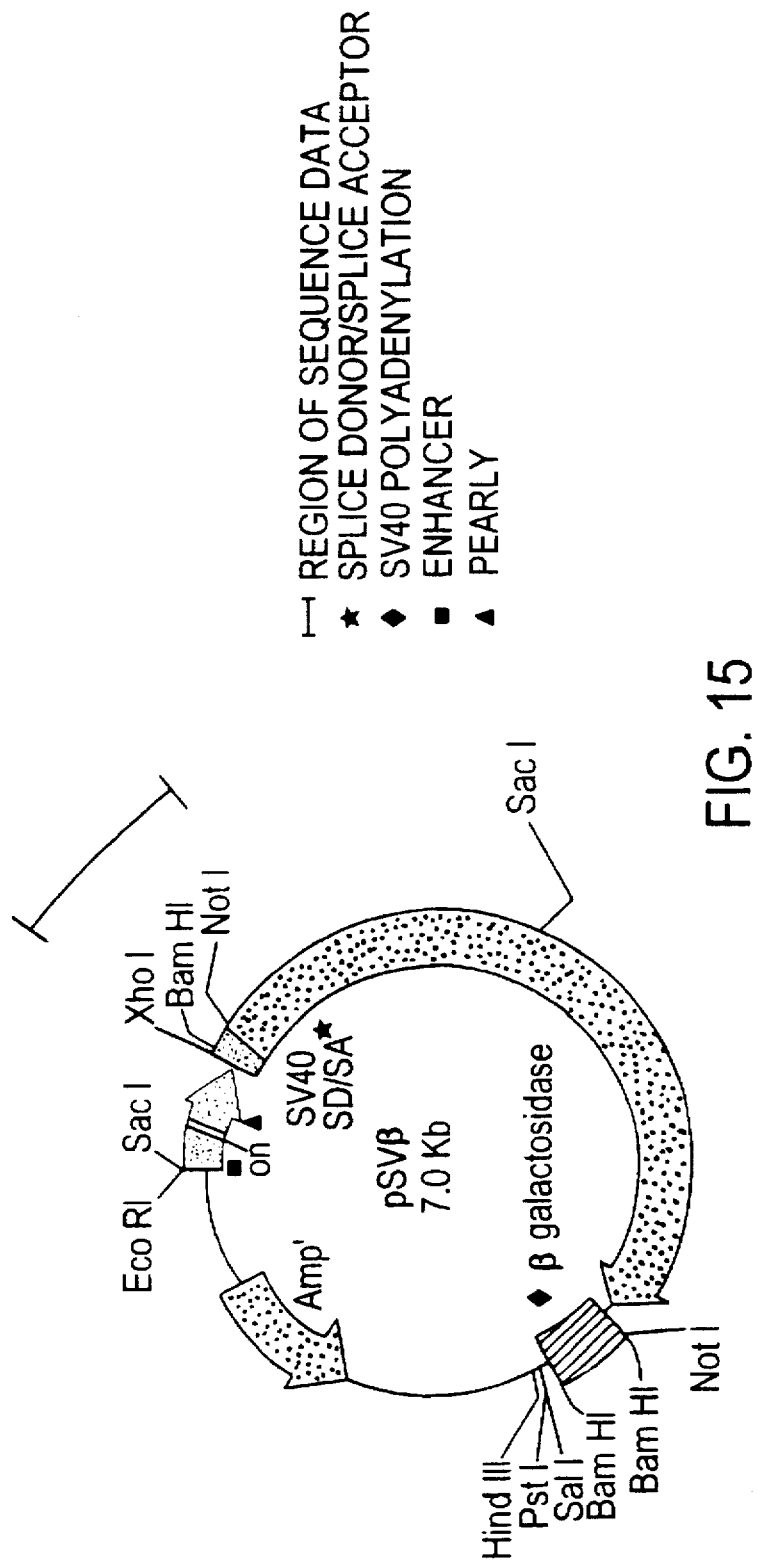
FIG. 15 is a schematic representation of the pSVβ used in the transformation experiments.
Figure 19A:
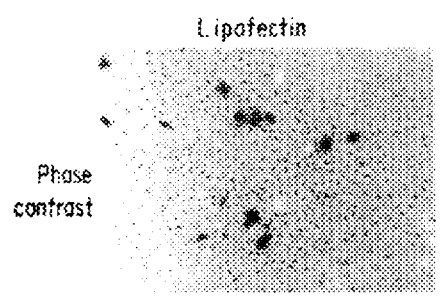
FIGS. 19A–19F illustrate the transfection efficiencies of Lipofectin, compound E, and compound M for the transfection of COS-7 cells with pSVβ plasmid under phase contrast and bright field conditions.
Figure 19B:
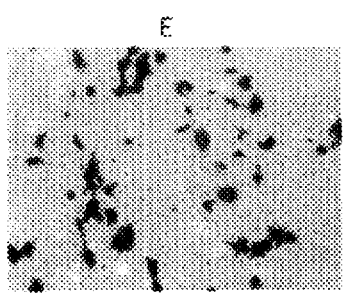
Figure 19C:
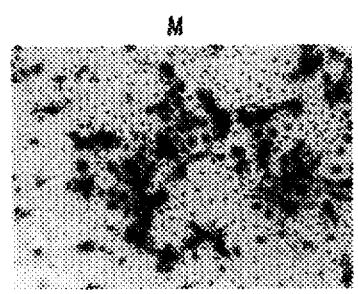
Figure 19D:
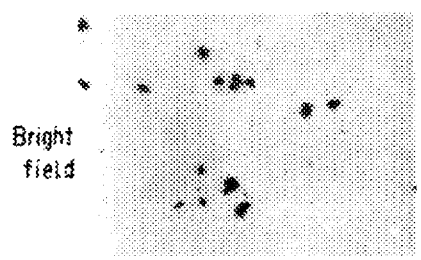
Figure 19E:
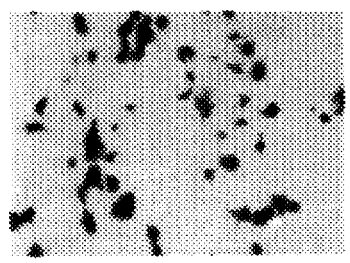
Figure 19F:
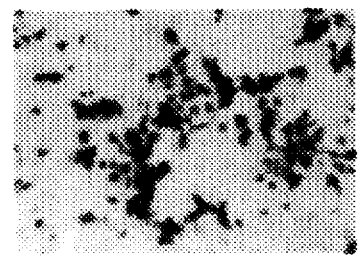
Figure 20:
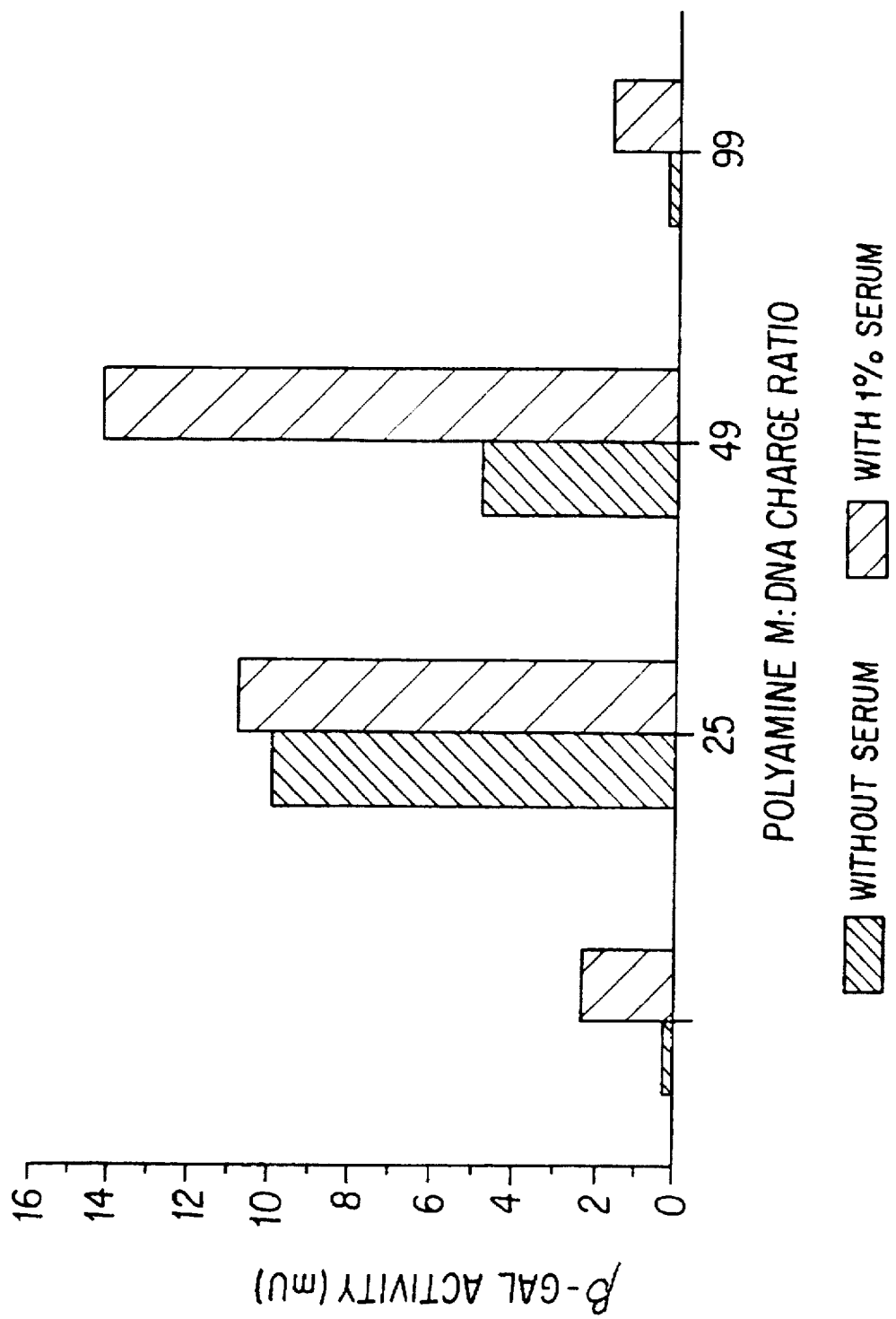
FIG. 20 illustrates the effect of the addition of 1% serum on the transfection of COS-7 cells with pSVβ plasmid in the presence of compound M/DOPE complex at various compound M to DNA charge ratios.

Accordingly, selected polyamine derivatives of cholic acid, deoxycholic acid, chenodeoxycholic acid, litocholic acid, and various mono and bisglycosylated derivatives thereof have been prepared (see, for example, FIGS. 12–14). The ability of these compounds to facilitate the introduction of nucleic acids (see, e.g., FIG. 15) into cells has been explored. The results, as shown in FIG. 16, for example, suggest a direct correlation between the number of amines present in the polyamine side chain of the test compound and the observed transfection efficiency. That is, the present study has shown that transfection efficiencies increase progressively in going from a spermine side chain (four amines including the amide linkage) to a pentaamine side chain to a hexaamine side chain. The results of specific transfection experiments are provided in FIG. 16 and in Tables 6 and 7, below.

proteins. In fact, as shown in FIG. 20, at a compound M to DNA charge ratio of about 49, increased β-galactosidase activity is observed in the presence of 1% serum relative to the β-galactosidase activity measured in the absence of serum. This result is noteworthy because it is known that the transfection efficiency of lipofectin is adversely affected by added serum.

Figure 21:
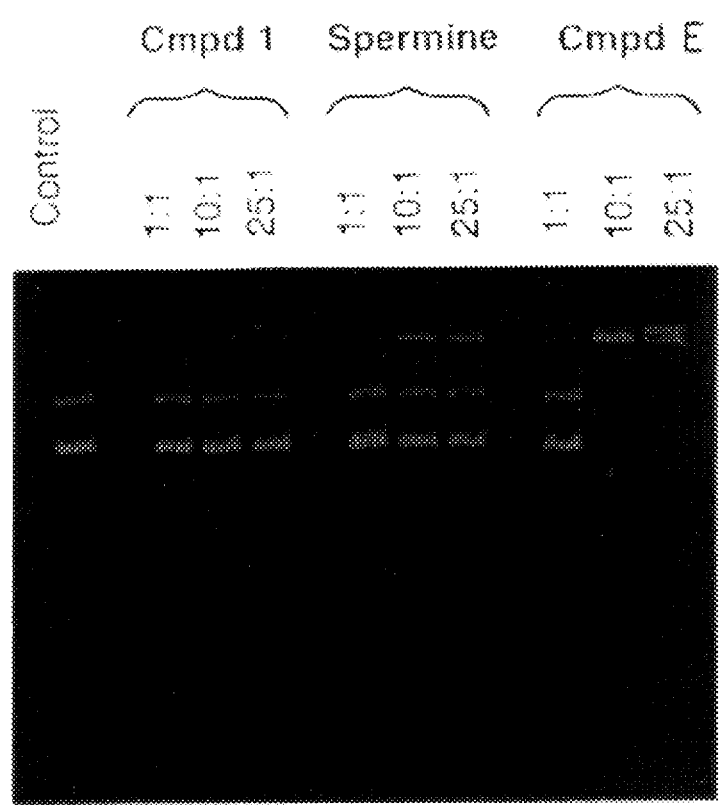
FIG. 21 presents the results of gel shift experiments using DNA alone (control), compound 1, spermine alone, and compound E, which is the spermine derivative of compound 1.

Also, gel shift/DNA binding experiments show that a glycosylated cholic acid methyl ester (compound 1) and spermine alone are unable separately to retard the migration of DNA through a gel (see, FIG. 21). The results of the present invention demonstrate, quite surprisingly, the ability of a compound of the present invention, which incorporates the structural features of the glycosylated compound and spermine to retard completely the migration of DNA substantially or at a compound to DNA ratio of as low as about 10 to 1. Hence, the ability of the compounds of the present invention to bind to DNA and their consequent ability to facilitate the transformation of cells could not have been suggested by the physicochemical behavior of the individual bisglycosylated cholic acid methyl ester and spermine molecules.

6.35 Additional Compounds

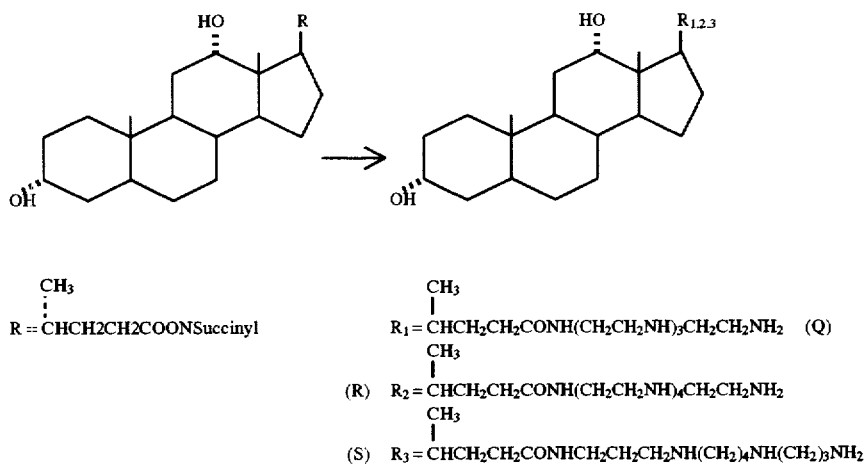

CH$_3$
|
R = CHCH2CH2COONSuccinyl

CH$_3$
|
R$_1$ = CHCH2CH2CONH(CH2CH2NH)$_3$CH2CH2NH$_2$    (Q)
CH$_3$
|
(R)   R$_2$ = CHCH2CH2CONH(CH2CH2NH)$_4$CH2CH2NH$_2$
CH$_3$
|
(S)   R$_3$ = CHCH2CH2CONHCH2CH2CH2NH(CH2)$_4$NH(CH2)$_3$NH$_2$

The results also suggest that each compound exhibits a maximum transfection efficiency that is dependent upon a particular compound to DNA charge ratio. For example, as shown in FIG. 17, compound E exhibits a four-fold advantage over lipofectin at a compound E to DNA charge ratio of approximately 96, whereas compound M facilitates transfection by a factor of about 12 over lipofectin at a compound M to DNA charge ratio of approximately 49.

Both the ONPG and X-GAL assays provide an effective measure of the transformation efficiencies of the compounds of the present invention, as illustrated by the results presented in FIG. 18. As noted elsewhere, the ONPG assay is a direct measure of the protein production of the transformed cells, whereas the X-GAL assay measures the density of stained cells that express heterologous β-galactosidase. A sampling of the X-GAL assay results is provided in FIG. 19.

Quite surprisingly, it has also been discovered that the transfection of COS-7 cells using a complex of compound M/DOPE is largely unaffected by the presence of serum 6.35.1 Deoxycholic acid, tetraethylenepentamide (O)

To a solution of tetraethylenepentamine (0.378 g, 2.5 mmol) and triethylamine (0.3 ml) in DMF (5 ml) the N-oxysuccinimide-deoxycholate (1.0 g, 2 mmol) in 5 ml of DMF is added dropwise during 10 min. The solution is stirred at R.T. overnight, then poured into water (20 ml). A precipitate of the product is washed with cold water (50 ml), and dissolved in 10 ml of 2% HCl, and filtered. The solution is poured onto a CHP-20 reverse phase column, and purified in MeOH-water solvent system. The product elutes in a solvent range of 40–80% of MeOH affording 1.1 g (yield 72%, m.p. 130°–132° C.) of the deoxycholic acid tetraethylenepentamide, trihydrichloride, pentahydrate, compound Q as a white powder (after lyophilization). TLC Rf (MeOH:i-PrNH$_2$; DCM-2:2:6) 0.6 IR (KBr): 3419, 2934, 1642 (CONH—), 1553, 1454, 1038 cm$^{-1}$. $^1$H NMR (D$_2$O): 3.88 (s., 1H), 2.9–3.3 (M, 16H), 1.2–2.4 (m, 42H), 0.88 (d., 3H), 0.78 (s., 3H), 0.55 (s., 3H). Fab MS: 696 (Base 3HCl+Na$^+$). Anal. Calc. for $C_{32}H_{61}N_5O_3 \cdot 3HCl.5H_2O$: C 50.3; H 9.69; N 9.17; Cl 13.95. Found: C 51.5; H 9.04; N 10.1; C 10.9.

6.35.2 Deoxycholic acid, pentaethylenehexamide (R)

To a solution of pentaethylenehexamine (0.58 g, 2.5 mmol) and triethylamine (0.3 ml) in DMF (5 ml) the N-oxysuccinimide-deoxycholate (1.0 g, 2 mmol) in 5 ml of DMF is added dropwise during 10 min. The resulting solution is stirred at R.T. overnight. The solution is poured in water (50 ml) to give a precipitate. The liquid phase is decanted. The semi-solid precipitate is washed with cold 5 NaOH (10 ml×2) and water (10 ml), dissolved in 10 ml of 10% acetic acid and purified by flash chromatography on CHP-20 reverse phase column in MeOH-water solvent system. The product elutes at 40% up to 100% of MeOH. The fractions with product are combined, evaporated at reduced pressure, dissolved in 2% HCl and lyophilized affording 0.75 g (yield 44%, m.p.) of compound R as a white powder, m.p. 140°–142° C. TLC Rf (MeOH:i-PrNH$_2$:DCM-2:2:6) 0.65. IR (KBr): 3425, 2932, 1770 (COOH), 1643 (CONH), 1552 (COO), 1454, 1032 cm$^{-1}$. $^1$H NMR (D$_2$O): 3.92 (s., 1H), 2.6–3.6 (m, 20H), 1.0–1.6 (M, 30H), 0.83 (D., 3H), 0.75 (s., 3H), 0.55 (s., 3H). Fab MS: 863 (M+H$^+$). Anal. Calc. for $C_{34}H_{66}N_6O_3 \cdot 2HCl.3AcOH$: C 55.8; H 9.28; N 9.70; Cl 8.2. Found: C 59.0; H 9.40; N 8.3; Cl 6.6.

6.35.3 Chenodeoxycholic acid, spermide, trifluoroacetate (S)

To a solution of spermine (0.8 g, 2 mmol) and triethylamine (0.3 ml) in 5 ml of DMF, the N-oxysuccinimide-chenodeoxycholate (1.0 g, 2 mmol) in 5 ml of DMF is added dropwise. The mixture is stirred at R.T. overnight. The solution is poured into DCM (100 ml), and the resulting precipitate of the hydroxysuccinimide is filtered; the filtrate is evaporated to give a liquid phase, which is poured into water (100 ml). The precipitate of the product is obtained. It is dissolved in MeOH (5 ml), and placed on CHP-20 reverse phase column. An MeOH-water solvent system is used. At 30% of MeOH the product elutes. The solvent is evaporated, the residue dissolved in 1 ml of trifluoroacetic acid, diluted up to 10 ml by water, filtered, and the filtrate is lyophilized affording 0.9 g (yield 50%), m.p. 96°–100° C. The product is dissolved in water to give a 5% solution of the trifluoroacetate salt of the chenodeoxycholic acid spermide. The solution is stable at R.T. about 12–24 h, then a precipitate of the base separates as a slurry. TLC Rf (MeOH:i-PrNH$_2$:DCM) 0.7. IR (KBr): 3406, 2939, 2869, 1778 (COOH), 1680 (CONH—), 1553, 1458, 1196, 834, 722 cm$^{-1}$. $^1$H NMR (D$_2$O): 3.75 (s., 1H), 3.4 (s., 1H), 2.8–3.15 (m. 12H), 2.2–1.2 (m. 39H), 0.9 (d, 3H), 0.86 (s. 3H), 0.55 (s. 3H). Fab MS: (M+Na$^+$)=598. Anal. Calc. for $C_{34}H_{64}N_4O_3 \cdot 3CF_3COOH$: $C_{52.5}$; H 7.29; N 6.09. Found C 53.5; H 7.20; N 4.95.

Other embodiments should be apparent to one of ordinary skill other than those specifically described above but which may, nonetheless, fall within the scope and spirit of the present invention. Those embodiments, which are specifically described, should not be construed as limiting the present invention in any way, which invention is limited solely by the following claims.

TABLE 6

SUMMARY OF TRANSFECTION RESULTS FOR C-3 OH COMPOUNDS

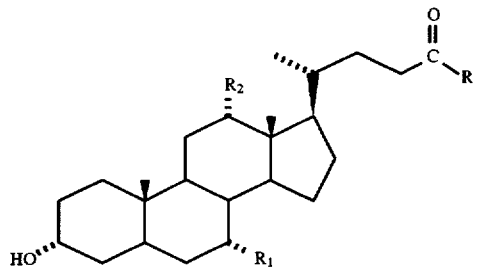

| Comp (R) | R$_1$ | R$_2$ | Ratio (Comp/DNA) Charge | Mole | % Transfection vs. Lipofection |
|---|---|---|---|---|---|
| Lipofectin | — | — | 4(16) | 7 | 100(100) |
| Spermine$^a$ | — | — | 93 | 47 | 30 |
| Spermine$^d$ | OH | OH | 25 | 17 | 27 |
| Spermine 3HCl$^e$ | H | O—Glc$^b$ | 24 | 16 | 20 |
| Spermine$^f$ | O—Glc | H | 24 | 16 | 208 |
| OCH$_3{}^g$ | O—Glc | O—Glc | N/A | 20 | 12 |
| NH(EtNH)$_3$EtNH$_2{}^c$ | O—Glc | O—Glc | 96 | 64 | 127 |
| NH(EtNH)$_3$EtNH$_2$ 2HCl.5H$_2$O$^q$ | H | OH | 29 | 15 | 378 |
| NH(EtNH)$_4$EtNH$_2{}^h$ | O—Glc | O—Glc | 48 | 20 | 1300 |
| NH(EtNH)$_4$EtNH$_2$ HCl.4HOAc$^r$ | H | OH | 15 | 6 | 827 |
| Spermine 3TFA$^i$ | H | OH | 5(13) | 3(9) | 159(460) |
| NH(CH$_2$)$_{12}$NH$_2{}^j$ | H | OH | 7 | 20 | 13 |
| Spermine 3HCl$^k$ | O—Glc | O—Glc | 95 | 64 | 344 |
| Spermine 2TFA$^n$ | OH | H | 9 | 6 | 233 |
| NH(EtNH)$_3$EtNH$_2$ 4HCl.2H$_2$O$^l$ | OH | H | 7 | 4 | 57 |
| NH(EtNH)$_4$EtNH$_2$ 3HCl.2H$_2$O$^m$ | OH | H | 9 | 4 | 38 |
| NH(EtNH)$_3$EtNH$_2$ 5HCl$^p$ | OH | OH | 56 | 28 | 1366 |
| NH(EtNH)$_4$EtNH$_2$ 7HCl$^o$ | OH | OH | 30 | 12 | 1314 |
| NH(EtNH)$_4$EtNH$_2$ 4HCl | O—Glc | O—Glc | 49 | 19 | 1215 |

TABLE 6-continued

SUMMARY OF TRANSFECTION RESULTS FOR C-3 OH COMPOUNDS

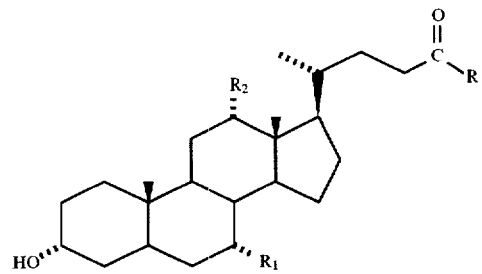

| | | | Ratio (Comp/DNA) | | % Transfection |
|---|---|---|---|---|---|
| Comp (R) | R$_1$ | R$_2$ | Charge | Mole | vs. Lipofection |
| NH(EtNH)$_3$EtNH$_2$ 3HCl | O—Glc | O—Glc | 252 | 126 | 128 |
| NH(EtNH)$_4$EtNH$_2$ 5HOAc$^p$ | H | H | 60 | 28 | 64 |

$^a$Spermine only.
$^b$O—Glc =

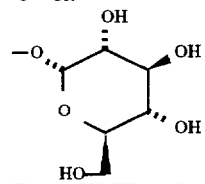

$^c$Et = —CH$_2$CH$_2$—; Comp N
$^d$Comp F
$^e$Comp O
$^f$Comp P
$^g$Comp L
$^h$Comp M
$^i$Comp B
$^j$Comp G
$^k$Comp E
$^l$Comp H
$^m$Comp I
$^n$Comp J
$^o$Comp K
$^p$Comp L
$^q$Comp Q
$^r$Comp R
$^s$Comp S

TABLE 7

SUMMARY OF TRANSFECTION RESULTS FOR C-3 NH$_2$ COMPOUNDS

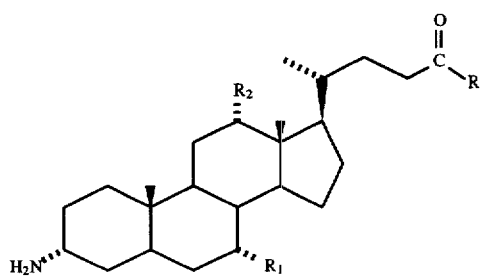

| | | | Ratio (Comp/DNA) | | % Transfection |
|---|---|---|---|---|---|
| Comp (R) | R$_1$ | R$_2$ | Charge | Mole | vs. Lipofection |
| Lipofectin | — | — | 4 | 7 | 100 |

TABLE 7-continued

SUMMARY OF TRANSFECTION RESULTS FOR C-3 NH$_2$ COMPOUNDS

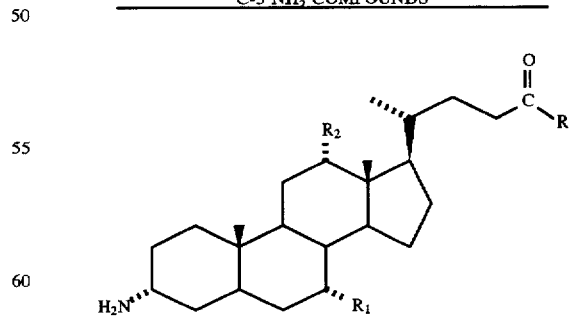

| | | | Ratio (Comp/DNA) | | % Transfection |
|---|---|---|---|---|---|
| Comp (R) | R$_1$ | R$_2$ | Charge | Mole | vs. Lipofection |
| OCH$_3$ | O—Glc$^a$ | O—Glc | 10 | 20 | 2 |

TABLE 7-continued
SUMMARY OF TRANSFECTION RESULTS FOR C-3 NH$_2$ COMPOUNDS

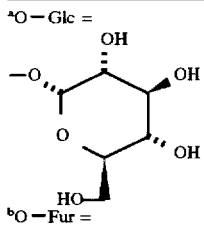

| Comp (R) | R$_1$ | R$_2$ | Ratio (Comp/DNA) Charge | Mole | % Transfection vs. Lipofection |
|---|---|---|---|---|---|
| OCH$_3$ | O—Glc | H | 4 | 9 | 213 |
| OCH$_3$ | H | O—Glc | 32 | 64 | 64 |
| OCH$_3$ | O—Fur$^b$ | O—Fur | 7 | 14 | 459 |
| OCH$_3$$^c$ | O—Glc | O—Glc | 24 | 49 | 39 |
| Spermine | O—Glc | O—Glc | 30 | 20 | 2 |

$^a$O—Glc =

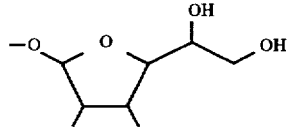

$^b$O—Fur =

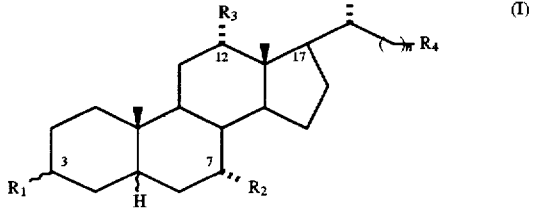

$^c$This compound is the α-C-3-amino isomer.

What is claimed is:

1. A method of introducing nucleic acid to a cell comprising:

(a) contacting a cell with the nucleic acid to be introduced in the presence of a fusogenic lipid and a compound of the formula (I):

(I)

in which

R$_1$ can be an H, OH, OR$_5$, NH$_2$, NHR$_6$ or NR$_6$R$_7$;

R$_2$ and R$_3$ may be the same or different and can be an H, OH or OR$_5$;

R$_4$ can be CONH$_2$, CONHR$_6$, CONR$_6$R$_7$, CH$_2$NH$_2$, CH$_2$NHR$_6$, CH$_2$NR$_6$R$_7$, CO$_2$—Y—NH$_2$, CO$_2$—Y—NHR$_6$, or CO$_2$—Y—NR$_6$R$_7$;

R$_5$ is a protected or unprotected glycosyl moiety comprising 1–10 monosaccharide units in which the glycosidic linkage at the anomeric carbon atom of each monosaccharide unit is independently alpha or beta;

NH$_2$, NHR$_6$, and NR$_6$R$_7$ represent an unsubstituted amino group, a monosubstituted amino group, and a disubstituted amino group, respectively, in which R$_6$ and R$_7$ may be the same or different and represent a hydrocarbon group comprising 1–15 carbon atoms substituted with one or more unsubstituted, monosubstituted or disubstituted amino groups;

Y represents a linear or branched alkylene group comprising 1–10 carbon atoms;

n is an integer from 0–10;

or its acid addition or quaternary ammonium salt; and (b) allowing said nucleic acid to remain in contact with said cell in the presence of said compound for a period of time sufficient to effect the introduction of said nucleic acid to said cell.

2. The method of claim 1 in which said introduction leads to the incorporation of said nucleic acid or at least a portion thereof within the genetic make-up of said cell.

3. The method of claim 2 in which said nucleic acid or at least a portion thereof becomes integrated within a chromosome of said cell.

4. The method of claim 2 in which said nucleic acid or at least a portion thereof is retained by said cell as extrachromosomal material.

5. The method of claim 1 in which said lipid is polar.

6. The method of claim 1 in which said lipid comprises a phospholipid.

7. The method of claim 6 in which said phospholipid contains a phosphatidylethanolamine head group.

8. The method of claim 7 in which said phospholipid is dioleoyl phosphatidylethanolamine.

9. The method of claim 7 in which said phospholipid is selected from the group consisting of palmitoyl oleoyl phosphatidylethanolamine or dimyristoyl phosphatidylethanolamine.

10. The method of claim 6 in which said phospholipid comprises a lysophospholipid.

11. The method of claim 6 in which said phospholipid is lysinyl phosphatidylethanolamine.

12. The method claim 1 in which a second lipid comprising a cationic lipid is also present in said contacting step.

13. The method of claim 12 in which said cationic lipid is selected from the group consisting of N-|1-(2,3-dioleoyloxy)pro-pyl|-N,N,N-trimethyl ammonium chloride (DOTMA), 1,2-dimyristoyl-3-trimethylammonium propane (DOTAP), and 1,2-dimyristoyl-3-dime-thylammonium propane (DODAP).

14. The method of claim 1 in which said contacting step is carried out further in the presence of diethylaminoethyl-dextran (DEAE).

15. The method of claim 1 in which said lipid comprises a fatty acid ester of a sugar, a glycosyl diacylglycerol, a plasmalogen, an aphingomyelin, a ganglioside, a glycerolipid, a sphingolipid or a cardiolipin.

16. The method of claim 1 in which said nucleic acid is pre-mixed with said compound before being allowed to contact said cells.

17. The method of claim 1 in which the group R$_6$ together with the nitrogen atom to which it is attached represents a biogenic polyamine.

18. The method of claim 1 in which said compound can accommodate at least two positive charges.

19. The method of claim 1 in which said compound can accommodate at least three positive charges.

20. The method of claim 1 in which R$_6$ or R$_7$ represents 3-aminopropyl, 4-aminobutyl, 5-aminopentyl, N-(4-aminobutyl)-3-aminopropyl or N-|N-(3-aminopropyl)-4-aminobutyl|-3-aminopropyl.

21. The method of claim 1 in which said nucleic acid is endogenous.

22. The method of claim 1 in which said nucleic acid is exogenous.

23. The method of claim 1 in which said nucleic acid comprises DNA.

24. The method of claim 1 in which said nucleic acid comprises RNA.

25. The method of claim 1 in which said nucleic acid encodes a gene.

26. The method of claim 1 in which said gene is mammalian.

27. A compound of the formula (I):

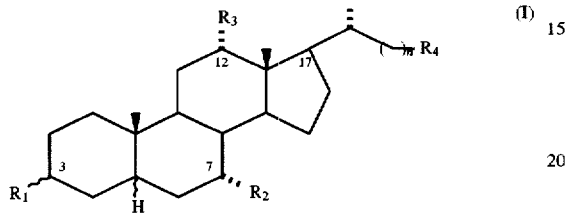

in which $R_1$ can be an H, OH, $OR_5$, $NH_2$, $NHR_6$, or $NR_6R_7$;

$R_2$ and $R_3$ may be the same or different and can be an H, OH or $OR_5$;

$R_4$ can be $CONHR_6$, $CONR_6R_7$, $CH_2NHR_6$, $CH_2NR_6R_7$, $CO_2$—Y—$NH_2$, $CO_2$—Y—$NHR_6$, or $CO_2$—Y—$NR_6R_7$;

$R_5$ is a protected or unprotected glycosyl moiety comprising 1-10 monosaccharide units in which the glycosidic linkage at the anomeric carbon atom of each monosaccharide unit is independently alpha or beta;

$NH_2$, $NHR_6$, and $NR_6R_7$ represent an unsubstituted amino group, a monosubstituted amino group, and a disubstituted amino group, respectively, in which $R_6$ and $R_7$ may be the same or different and represent a hydrocarbon group comprising 1-15 carbon atoms substituted with one or more unsubstituted, monosubstituted or disubstituted amino groups;

Y represents a linear or branched alkylene group comprising 1-10 carbon atoms;

n is an integer from 0-3;

or its acid addition or quaternary ammonium salt; provided that said compound comprises at least one $R_6$ group as defined above substituted with at least one unsubstituted amino group.

28. The compound of claim 27 in which R1 has the configuration beta.

29. The compound of claim 27 in which R1 has the configuration alpha.

30. The compound of claim 27 in which at least one of $R_1$, $R_2$, and $R_3$ represents OH.

31. The compound of claim 27 in which at least two of $R_1$, $R_2$, and $R_3$ represent OH.

32. The compound of claim 27 in which all three of $R_1$, $R_2$, and $R_3$ represent OH.

33. The compound of claim 27 in which $R_1$ and $R_2$ represent $OR_5$, and $R_3$ represents OH.

34. The compound of claim 27 in which $R_1$ and $R_3$ represent $OR_5$, and $R_2$ represents OH.

35. The compound of claim 27 in which $R_2$ and $R_3$ represent $OR_5$, and $R_1$ represents OH.

36. The compound of claim 27 in which the group $R_6$ together with the nitrogen atom to which it is attached represents a biogenic polyamine.

37. The compound of claim 27 which can accommodate at least three positive charges.

38. The compound of claim 27 in which $R_6$ or $R_7$ represents 3-aminopropyl, 4-aminobutyl, 5-aminopentyl, N(4-aminobutyl)-3-aminopropyl or N-|N-(3-aminopropyl)-4-aminobutyl|-3-aminopropyl.

39. A composition for the introduction of nucleic acid to a cell comprising nucleic acid, an effective amount of a fusogenic lipid, and an effective amount of a compound of the formula (I):

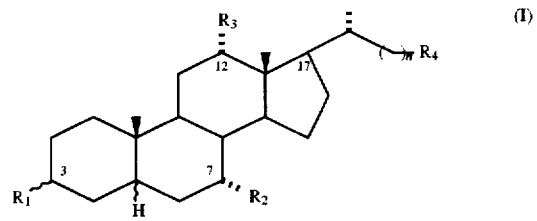

in which $R_1$ can be an H, OH, $OR_5$, $NH_2$, $NHR_6$, or $NR_6R_7$;

$R_2$ and $R_3$ may be the same or different and can be an H, OH or $OR_5$;

$R_4$ can be $CONH_2$, $CONHR_6$, $CONR_6R_7$, $CH_2NH_2$, $CH_2NHR_6$, $CH_2NR_6R_7$, $CO_2$—Y—$NH_2$, $CO_2$—Y—$NHR_6$, or $CO_2$—Y—$NR_6R_7$;

$R_5$ is a protected or unprotected glycosyl moiety comprising 1-10 monosaccharide units in which the glycosidic linkage at the anomeric carbon atom of each monosaccharide unit is independently alpha or beta;

$NH_2$, $NHR_6$, and $NR_6R_7$ represent an unsubstituted amino group, a monosubstituted amino group, and a disubstituted amino group, respectively, in which $R_6$ and $R_7$ may be the same or different and represent a hydrocarbon group comprising 1-15 carbon atoms substituted with one or more unsubstituted, monosubstituted or disubstituted amino groups;

Y represents a linear or branched alkylene group comprising 1-10 carbon atoms;

n is an integer from 0-10;

or its acid addition or quaternary ammonium salt.

40. The composition of claim 39 in which said compound comprises at least one $R_6$ group as defined in claim 39 substituted with at least one unsubstituted amino group.

41. The composition of claim 40 which further comprises a liquid carrier.

42. The composition of claim 40 which further comprises a lipid.

43. The composition of claim 40 which further comprises a fusogenic lipid and a buffer.

44. A pharmaceutical composition comprising a nucleic acid and a compound of the formula (I):

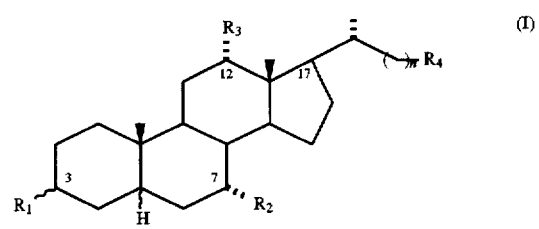

in which $R_1$ can be an H, OH, $OR_5$, $NH_2$, $NHR_6$ or $NR_6R_7$;

$R_2$ and $R_3$ may be the same or different and can be an H, OH or $OR_5$;

R$_4$ can be CONH$_2$, CONHR$_6$, CONR$_6$R$_7$, CH$_2$NH$_2$, CH$_2$NHR$_6$, CH$_2$NR$_6$R$_7$, CO$_2$—Y—NH$_2$, CO$_2$—Y—NHR$_6$, or CO$_2$—Y—NR$_6$R$_7$;

R$_5$ is a protected or unprotected glycosyl moiety comprising 1–10 monosaccharide units in which the glycosidic linkage at the anomeric carbon atom of each monosaccharide unit is independently alpha or beta;

NH$_2$, NHR$_6$, and NR$_6$R$_7$ represent an unsubstituted amino group, a monosubstituted amino group, and a disubstituted amino group, respectively, in which R$_6$ and R$_7$ may be the same or different and represent a hydrocarbon group comprising 1–15 carbon atoms substituted with one or more unsubstituted, monosubstituted or disubstituted amino groups;

Y represents a linear or branched alkylene group comprising 1–10 carbon atoms;

n is an integer from 0–10;

or its acid addition or quaternary ammonium salt in a pharmaceutically acceptable carrier, provided that said compound comprises at least one R$_6$ group as defined above.

45. The pharmaceutical composition of claim 44 in which said compound comprises at least one R$_6$ group substituted with at least one unsubstituted amino group.

46. The pharmaceutical composition of the claim 44 in which said nucleic acid encodes a gene.

47. The pharmaceutical composition of the claim 44 in which said nucleic acid comprises an antisense oligonucleotide sequence.

48. A conjugate comprising a bile acid or its analog selected from the group consisting of cholic acid, 3-amino-5β-cholic acid, lithocholic acid, deoxycholic acid, chenodeoxy cholic acid, 3-deoxycholic acid, its salt, ester, or amide covalently linked directly or indirectly to one or more second compounds attached to C3, the C17 side chain or both, provided that said second compound or compounds do not introduce a second molecule of said bile acid or its analog into said conjugate.

49. The conjugate of claim in which said 3-amino-5β-cholic acid is the 3β-amino isomer.

50. The conjugate of claim in which said 3-amino-5β-cholic acid is the 3α-amino isomer.

51. A conjugate comprising a 3-amino-7α,12α-di(1'α-glucosyl)-5β-cholic acid, its salt, ester or amide covalently linked directly or indirectly to one or more second compounds attached to C3, the C17 side chain or both, provided that said second compound or compounds do not introduce a second molecule of said 3-amino-7α,12αdi (1'α-glucosyl)-5β-cholic acid, its salt, ester or amide into said conjugate.

52. The conjugate of claim 51 in which said 3-amino-7α,12α-di(1'α-glucosyl)-5β-cholic acid is the 3β-amino isomer.

53. The conjugate of claim 51 in which said 3-amino-7α,12α-di(1'α-glucosyl)-5β-cholic acid is the 3α-amino isomer.

54. The conjugate of claim 48 in which said second compound is an amine compound.

55. The conjugate if claim 54 in which said amine compound is a polyamine compound.

56. The conjugate of claim 48 in which said polyamine compound is an alkylene diamine.

57. The conjugate of claim 48 in which said polyamine compound is a spermine.

58. The conjugate of claim 48 in which said polyamine compound is a spermidine.

59. The method of claim 1 in which said hydrocarbon group comprises a linear or branched aliphatic group.

60. The method of claim 1 in which said hydrocarbon group is cyclic.

61. The compound of claim 27 in which said hydrocarbon group comprises a linear or branched aliphatic group.

62. The compound of claim 27 in which said hydrocarbon group is cyclic.

63. The composition of claim 39 in which said hydrocarbon group comprises a linear or branched aliphatic group.

64. The composition of claim 39 in which said hydrocarbon group is cyclic.

65. The pharmaceutical composition of claim 44 in which said hydrocarbon group comprises a linear or branched aliphatic group.

66. The pharmaceutical composition of claim 44 in which said hydrocarbon group is cyclic.

* * * * *